(12) United States Patent
Yoo et al.

(10) Patent No.: US 9,249,219 B2
(45) Date of Patent: Feb. 2, 2016

(54) HUMAN MONOCLONAL ANTIBODY NEUTRALIZING VASCULAR ENDOTHELIAL GROWTH FACTOR RECEPTOR AND USE THEREOF

(71) Applicant: PHARMABCINE INC., Daejeon (KR)

(72) Inventors: Jin-San Yoo, Daejeon (KR); Weon-Sup Lee, Daejeon (KR); Sang-Ryeol Shim, Daejeon (KR); Mi-Hee Park, Daejeon (KR); Jeong-Eun Kang, Daejeon (KR); Do-Yun Kim, Seoul (KR); Joon-Chul Lee, Incheon (KR); Dong-Heon Lee, Daejeon (KR); Too-Hyon Cho, Incheon (KR); Sam-Sook Sul, Incheon (KR); Young-Guen Kwon, Seoul (KR); Bo-Jeong Pyun, Seoul (KR); Kwi-Hwa Kim, Daejeon (KR); Chae-Ok Yun, Seoul (KR); Nahm-Ju Kim, Daejeon (KR); Jae-Won Jeon, Daejeon (KR); Dong-Sup Lee, Seoul (KR); Young-Woo Park, Daejeon (KR); Geun-Bae Rha, Cheongju-si (KR); Hyun-Sook Jang, Daejeon (KR); Hyeon-Mi Yoo, Daejeon (KR); Sung-Woo Kim, Daejeon (KR); Semi Kim, Daejeon (KR); Sang-Seok Koh, Daejeon (KR)

(73) Assignee: PHARMABCINE INC., Daejeon (KR)

( * ) Notice: Subject to any disclaimer, the term of this patent is extended or adjusted under 35 U.S.C. 154(b) by 87 days.

(21) Appl. No.: 14/204,295

(22) Filed: Mar. 11, 2014

(65) Prior Publication Data
US 2014/0275488 A1      Sep. 18, 2014

Related U.S. Application Data

(62) Division of application No. 12/664,226, filed as application No. PCT/KR2007/003077 on Jun. 26, 2007, now Pat. No. 9,150,650.

(30) Foreign Application Priority Data

Jun. 13, 2007   (KR) ................. 10-2007-0057719

(51) Int. Cl.
| | | |
|---|---|---|
| *C07K 16/00* | (2006.01) | |
| *C07K 16/28* | (2006.01) | |
| *C07K 16/30* | (2006.01) | |
| *G01N 33/574* | (2006.01) | |
| *A61K 39/00* | (2006.01) | |

(52) U.S. Cl.
CPC ............. *C07K 16/2863* (2013.01); *C07K 16/30* (2013.01); *C07K 16/3023* (2013.01); *C07K 16/3046* (2013.01); *G01N 33/574* (2013.01); *A61K 2039/505* (2013.01); *C07K 2316/96* (2013.01); *C07K 2317/21* (2013.01); *C07K 2317/565* (2013.01); *C07K 2317/622* (2013.01); *C07K 2317/73* (2013.01); *C07K 2317/76* (2013.01); *C07K 2317/92* (2013.01); *C07K 2319/00* (2013.01)

(58) Field of Classification Search
None
See application file for complete search history.

*Primary Examiner* — Brad Duffy
(74) *Attorney, Agent, or Firm* — Kile Park Reed & Houtteman PLLC

(57) ABSTRACT

The present invention relates to human monoclonal antibodies neutralizing vascular endothelial growth factor receptor and the use thereof. More specifically, relates to human ScFv molecules neutralizing vascular endothelial growth factor receptor, and a composition for inhibiting angiogenesis and a composition for treating cancer, which contain the human ScFv molecules. The disclosed monoclonal antibody neutralizing vascular endothelial growth factor receptor shows excellent neutralizing ability in living cells, compared to that of a commercially available antibody against vascular endothelial growth factor receptor, and shows the ability to neutralize vascular endothelial growth factor receptor not only in humans, but also in mice and rats. Thus, the monoclonal antibody will be useful in anticancer studies and will be highly effective in cancer treatment.

6 Claims, 25 Drawing Sheets

FIG. 1

MESKVLLAVA LWLCVETRAA SVGLPSVSLD LPRLSIQKDI LTIKANTTLQ
    Signal                    ECD 1
ITCRGQRDLD WLWPNNQSGS EQRVEVTECS DGLFCKTLTI PKVIGNDTGA
YKCFYRETDL ASVIYVYVQD YRSPFIASVS DQHGVVYITE NKNKTVVIPC
                       ECD 2
LGSISNLNVS LCARYPEKRF VPDGNRISWD SKKGFTIPSY MISYAGMVFC
EAKINDESYQ SIMYIVVVG YRIYDVVLSP SHGIELSVGE KLVLNCTART
                      ECD 3
ELNVGIDFNW EYPSSKHQHK KLVNRDLKTQ SGSEMKKFLS TLTIDGVTRS
DQGLYTCAAS SGLMTKKNST FVRVHEKASS GLVPRGSDKT HTCPPCPAPE
                                 thrombin site    Fc
LLGGPSVFLF PPKPKDTLMI SRTPEVTCVV VDVSHEDPEV KFNWYVDGVE
VHNAKTKPRE EQYNSTYRVV SVLTVLHQDW LNGKEYKCKV SNKALPAPIE
KTISKAKGQP REPQVYTLPP SRDELTKNQV SLTCLVKGFY PSDIAVEWES
NGQPENNYKT TPPVLDSDGS FFLYSKLTVD KSRWQQGNVF SCSVMHEALH
NHYTQKSLSL SPGKEQKLIS EEDL
                   Myc tag

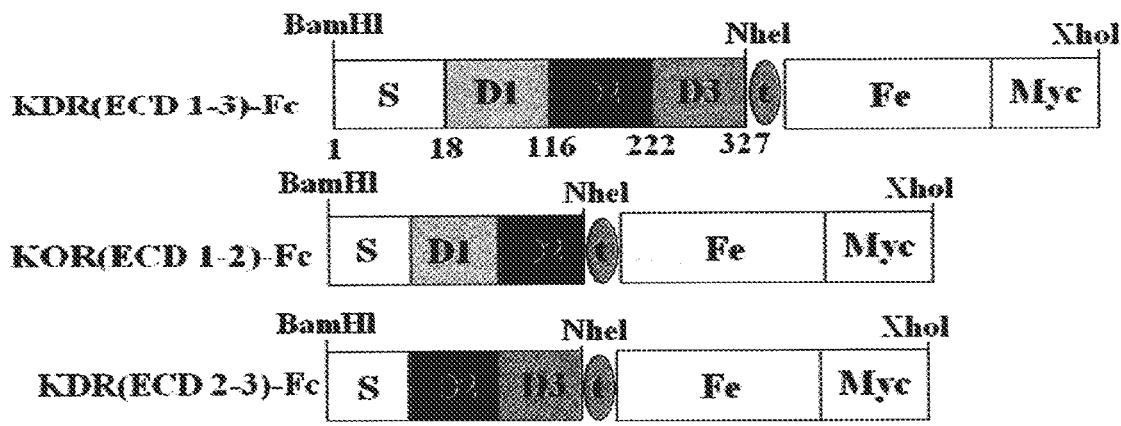

```
1    atg aaa tac cta ttg cct acg gca gcc gct gga ttg tta tta ctc    45
1    Met Lys Tyr Leu Leu Pro Thr Ala Ala Ala Gly Leu Leu Leu Leu    15
       Leader       SfiI
46   gcg gcc cag ccg gcc atg gcc cag cag ctg gtg cag tct ggg         90
16   Ala Ala Gln Pro Ala Met Ala Gln Gln Leu Val Gln Ser Gly         30
                                      VH
91   gct gaa gtg aag aag cct ggg gct tca gtg aag ctg tcc tgc aag    135
31   Ala Glu Val Lys Lys Pro Gly Ala Ser Val Lys Leu Ser Cys Lys    45

136  gct tct ggc tac acc ttc agc agc tac tgg atg cac tgg gtg cgc    180
46   Ala Ser Gly Tyr Thr Phe Ser Ser Tyr Trp Met His Trp Val Arg    60
                                     CDR1
181  cag gcc cct gga caa cgc ctt gag tgg atg gga gag att aat cct    225
61   Gln Ala Pro Gly Gln Arg Leu Glu Trp Met Gly Glu Ile Asn Pro    75

226  ggc aac ggt cat act aac tac aac gag aag ttc aag tca cgc gtg    270
76   Gly Asn Gly His Thr Asn Tyr Asn Glu Lys Phe Lys Ser Arg Val    90
                             CDR2
271  aca atc act gta gac aaa tcc gcg agc aca gcc tac atg gag ctc    315
91   Thr Ile Thr Val Asp Lys Ser Ala Ser Thr Ala Tyr Met Glu Leu    105

316  agc agc ctg aga tct gag gac acg gcc gtg tat tac tgt gcg aaa    360
106  Ser Ser Leu Arg Ser Glu Asp Thr Ala Val Tyr Tyr Cys Ala Lys    120

361  att tgg ggc ccg agt ctt act tct ccc ttt gac tac tgg ggc cag    405
121  Ile Trp Gly Pro Ser Leu Thr Ser Pro Phe Asp Tyr Trp Gly Gln    135
                          CDR3                    SfiI
406  gga acc ctg gtc acc gtc tcc tca ggc ctc ggg ggc ctc gga gga    450
136  Gly Thr Leu Val Thr Val Ser Ser Gly Leu Gly Gly Leu Gly Gly    150
                                                        BstXI
451  gga ggt agt ggc gga gga ggc tcc ggt gga tcc agc ggt gtg ggt    495
151  Gly Gly Ser Gly Gly Gly Gly Ser Gly Gly Ser Ser Gly Val Gly    165

496  tcc aat ttt atg ctg act cag ccc ccc tca gtg tca gtg tcc cca    540
166  Ser Asn Phe Met Leu Thr Gln Pro Pro Ser Val Ser Val Ser Pro    180
             VL
541  gga aag acg gcc agg atc acc tgt agg gga gat aac ctt gga gat    585
181  Gly Lys Thr Ala Arg Ile Thr Cys Arg Gly Asp Asn Leu Gly Asp    195

586  gta aat gtt cac tgg tac cag cag cgg cca ggc cag gcc cct gta    630
196  Val Asn Val His Trp Tyr Gln Gln Arg Pro Gly Gln Ala Pro Val    210
                CDR1
631  ttg gtc atg tat tat gat gcc gac cgg ccc tca ggg atc cct gag    675
211  Leu Val Met Tyr Tyr Asp Ala Asp Arg Pro Ser Gly Ile Pro Glu    225
                              CDR2
676  cga ttc tct ggc tcc aac tct ggg aac acg gcc aca ctg acc atc    720
226  Arg Phe Ser Gly Ser Asn Ser Gly Asn Thr Ala Thr Leu Thr Ile    240

721  agc gga gtc gaa gcc ggg gat gag gcc gac tac tat tgt cag gtg    765
241  Ser Gly Val Glu Ala Gly Asp Glu Ala Asp Tyr Tyr Cys Gln Val    255

766  tgg gat agg act agt gag tat gtc ttc gga act ggg acc aag gtc    810
256  Trp Asp Arg Thr Ser Glu Tyr Val Phe Gly Thr Gly Thr Lys Val    270
                           CDR3              BstXI
811  acc gtc cta ggt gga gga gcc agc ctc gtg gaa ttc gag cag aag    855
271  Thr Val Leu Gly Gly Gly Ala Ser Leu Val Glu Phe Glu Gln Lys    285
                                                      Myc tag
856  ctg atc tct gag gaa gac ctg tga    879
286  Leu Ile Ser Glu Glu Asp Leu  *      292
                             Amber
```

HUVEC-proliferation inhibition

FIG. 21
A
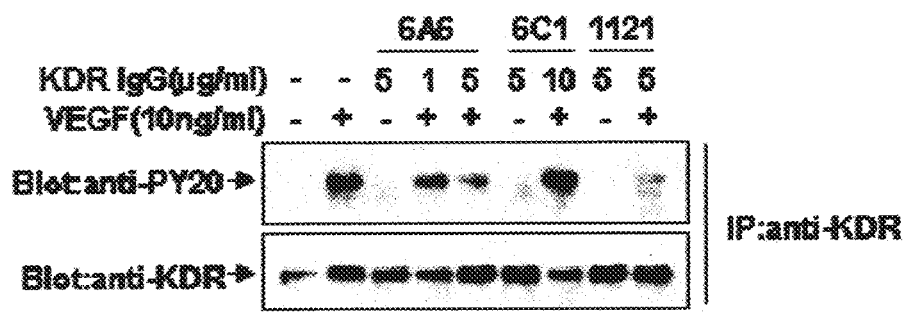
B
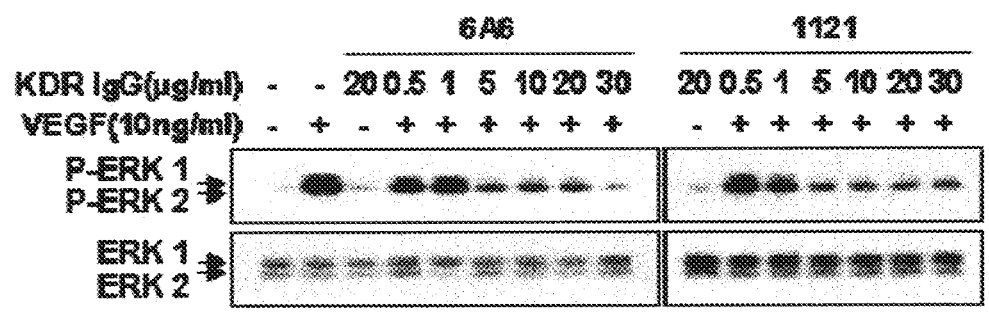
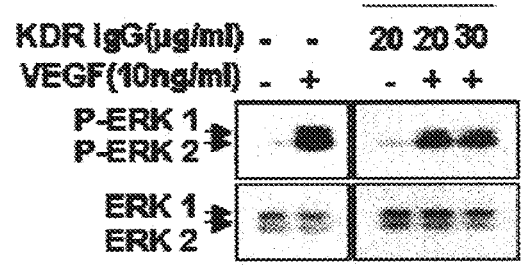

FIG. 23
A
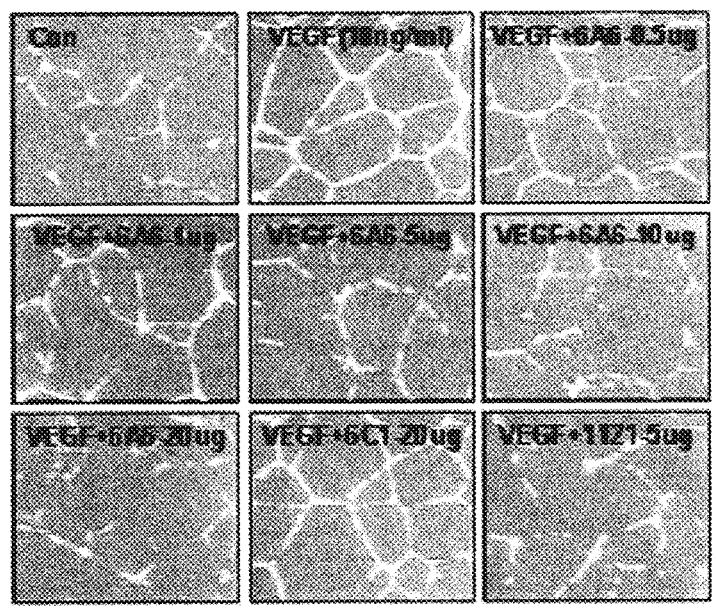
B
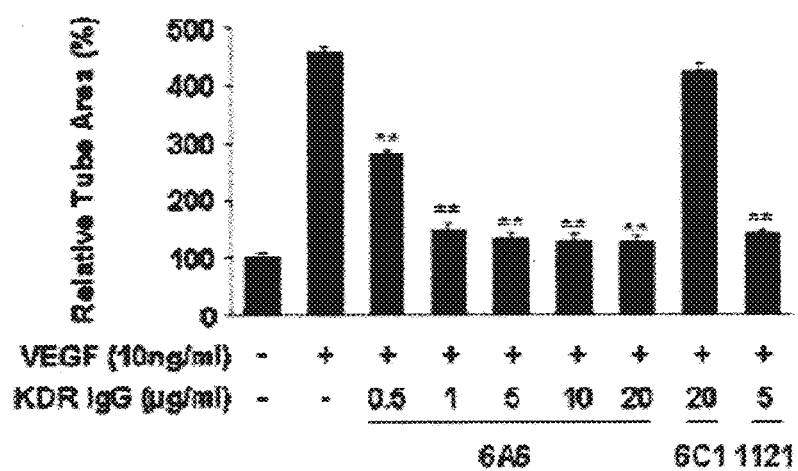

a; CON, b; VEGF, c; 6A6,
d; VEGF+6A6, e; 6G1, f; VEGF+6G1
g; 1C11, h; VEGF+1C11

FIG. 25
A
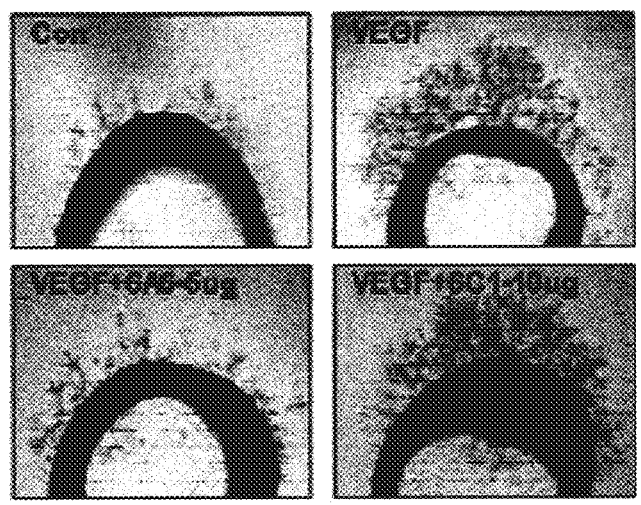
B
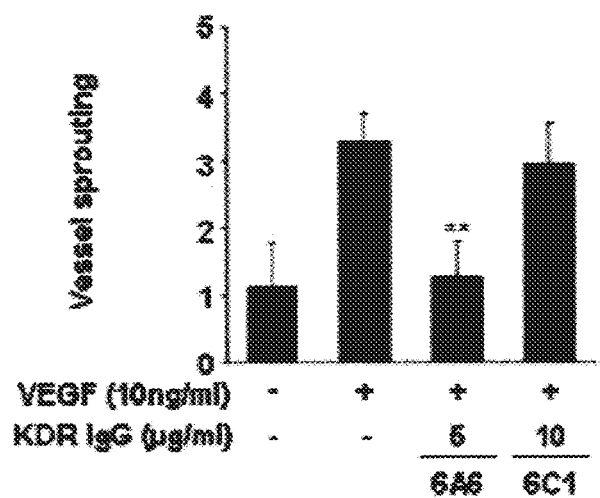

FIG. 26
A
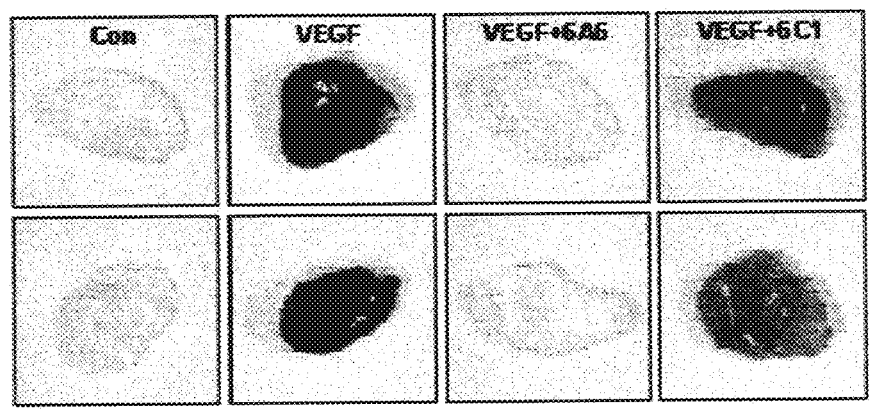
B
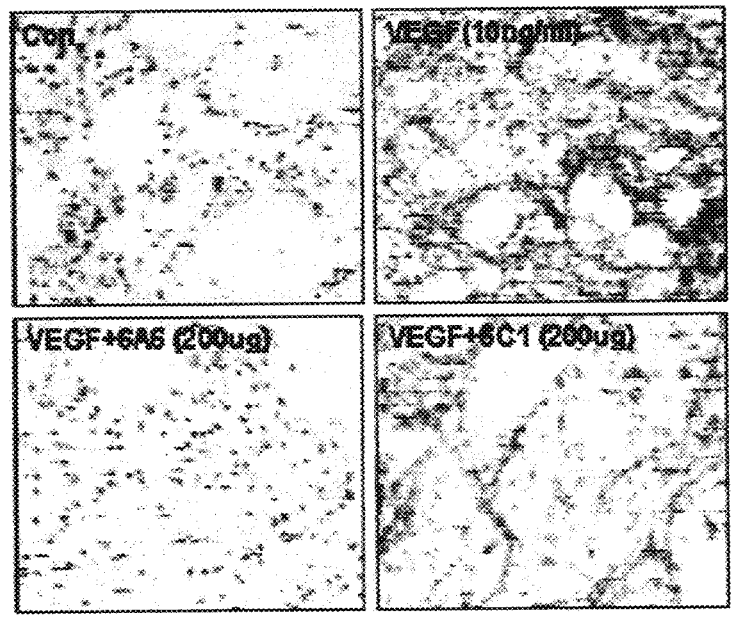

FIG. 31
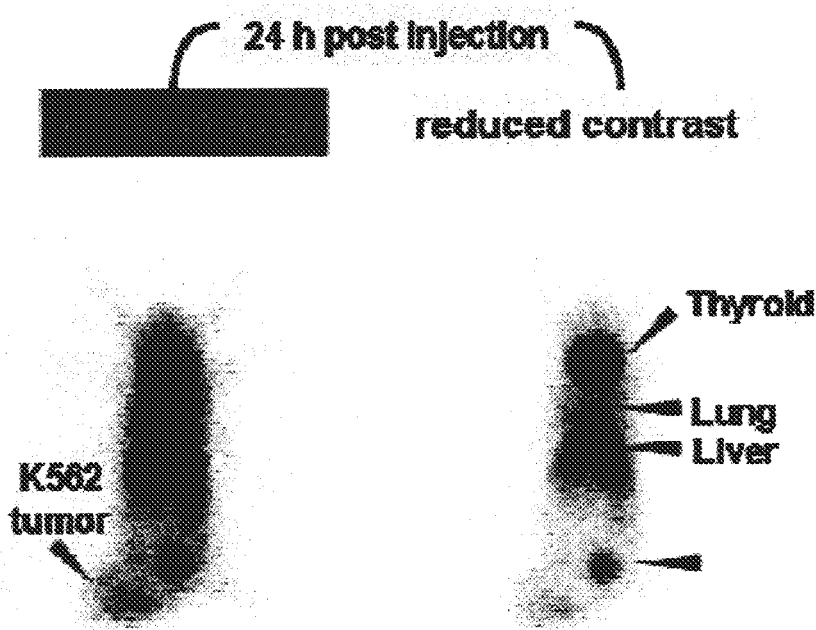

FIG. 35
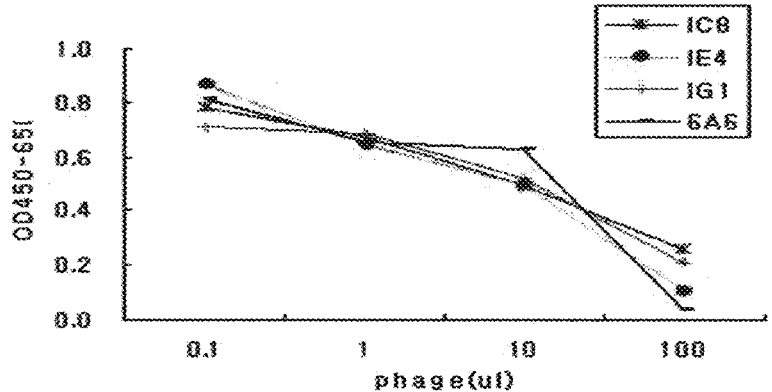
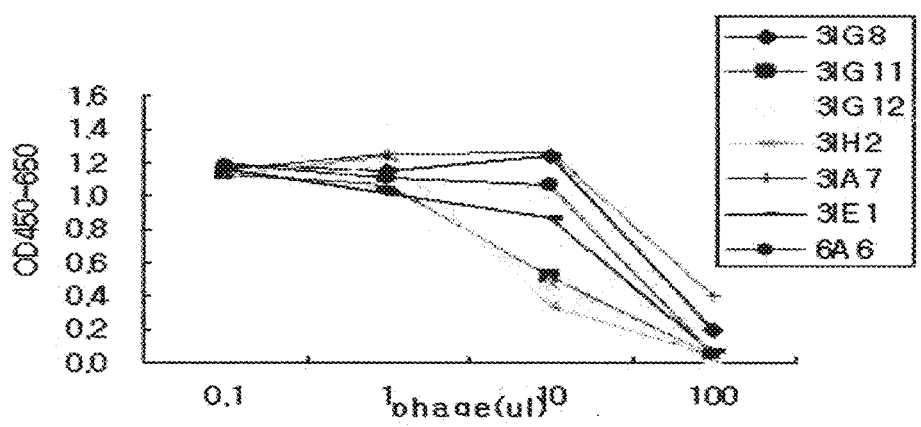
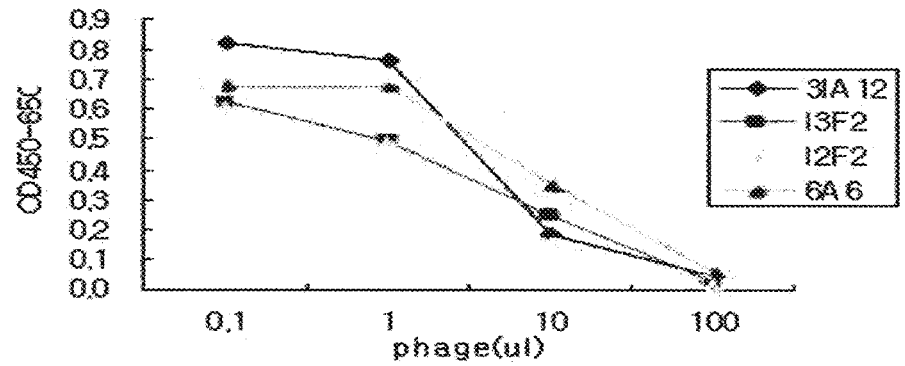

SEQUENCE LISTING

<160> NUMBER OF SEQ ID NOS: 181

<210> SEQ ID NO 1
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 1

Asn Phe Met Leu Thr Gln Pro Pro Ser Val Ser Val Ser Pro Gly Lys
1               5                   10                  15

Thr Ala Arg Ile Thr Cys Arg Gly Asp Asn Leu Gly Asp Val Asn Val
            20                  25                  30

His Trp Tyr Gln Gln Arg Pro Gly Gln Ala Pro Val Leu Val Met Tyr
        35                  40                  45

Tyr Asp Ala Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

```
Asp Glu Ala Asp Tyr Tyr Cys Gln Val Trp Asp Arg Thr Ser Glu Tyr
                85                  90                  95

Val Phe Gly Thr Gly Thr Lys Val Thr Val Leu Gly
            100                 105
```

<210> SEQ ID NO 2
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 2

```
Asn Phe Met Leu Thr Gln Pro Pro Ser Val Ser Val Ala Pro Gly Lys
1               5                   10                  15

Thr Ala Arg Ile Thr Cys Gly Gly Asp Asn Ile Gly Ser Gln Ser Val
            20                  25                  30

His Trp Tyr Gln Gln Arg Pro Gly Gln Ala Pro Val Leu Val Met Tyr
        35                  40                  45

Tyr Asp Ala Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Arg Thr Ser Glu Tyr
                85                  90                  95

Val Phe Gly Thr Gly Thr Lys Val Thr Val Leu Gly
            100                 105
```

<210> SEQ ID NO 3
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 3

```
Asn Phe Met Leu Thr Gln Pro Pro Ser Val Ser Val Ala Pro Gly Lys
1               5                   10                  15

Thr Ala Gly Ile Thr Cys Gly Gly Asp Asp Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Arg Thr Ser Glu Tyr
                85                  90                  95

Val Phe Gly Thr Gly Thr Lys Val Thr Val Leu Gly
            100                 105
```

<210> SEQ ID NO 4
<211> LENGTH: 107
<212> TYPE: PRT
<213> ORGANISM: Artificial Sequence
<220> FEATURE:
<223> OTHER INFORMATION: Antibody light chain variable region

<400> SEQUENCE: 4

```
Ser Tyr Glu Leu Thr Gln Pro Pro Ser Val Ser Ser Ala Pro Gly Lys
```

```
                1               5                  10                 15
                Thr Ala Thr Ile Thr Cys Glu Gly Lys Asn Ile Gly Ser Lys Ser Val
                                20                 25                 30

His Trp Tyr Gln Gln Lys Pro Gly Gln Ala Pro Val Leu Leu Ile Tyr
                            35                 40                 45

Tyr Asp Gln Asp Arg Pro Ser Ala Ile Pro Glu Arg Phe Ser Gly Ser
                        50                 55                 60

Asn Ser Asp Asn Met Ala Thr Leu Thr Ile Ser Arg Val Ala Ala Gly
                65                  70                 75                 80

Asp Glu Ala Asp Tyr Tyr Cys Gln Val Trp Gly Asn Gly Lys Val Val
                                85                 90                 95

Phe Gly Gly Gly Thr Lys Leu Thr Val Leu Gly
                            100                105

<210> SEQ ID NO 5
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 5

Asn Phe Met Leu Thr Gln Pro Pro Ser Val Ser Val Ala Pro Gly Lys
                1               5                  10                 15

Thr Ala Arg Ile Thr Cys Arg Gly Asp Asn Leu Gly Asp Val Asn Val
                                20                 25                 30

His Trp Tyr Gln Gln Arg Pro Gly Gln Ala Pro Val Leu Val Met Tyr
                            35                 40                 45

Tyr Asp Ala Asp Arg Pro Ser Gly Ile Pro Glu Arg Phe Ser Gly Ser
                        50                 55                 60

Asn Ser Gly Asn Thr Ala Thr Leu Thr Ile Ser Gly Val Glu Ala Gly
                65                  70                 75                 80

Asp Glu Ala Asp Tyr Tyr Cys Gln Val Trp Asp Arg Thr Ser Glu Tyr
                                85                 90                 95

Val Phe Gly Ala Gly Thr Lys Val Thr Val Leu Gly
                            100                105

<210> SEQ ID NO 6
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 6

Asn Phe Met Leu Thr Gln Pro Pro Ser Val Ser Val Ala Pro Gly Lys
                1               5                  10                 15

Thr Ala Arg Ile Thr Cys Arg Gly Asp Asn Leu Gly Asp Val Asn Val
                                20                 25                 30

His Trp Tyr Gln Gln Arg Pro Gly Gln Ala Pro Val Leu Val Met Tyr
                            35                 40                 45

Tyr Asp Ala Asp Arg Pro Ser Gly Ile Pro Glu Arg Phe Ser Gly Ser
                        50                 55                 60

Asn Ser Gly Asn Thr Ala Thr Leu Thr Ile Ser Gly Val Glu Ala Gly
                65                  70                 75                 80

Asp Glu Ala Asp Tyr Tyr Cys Gln Val Trp Asp Arg Thr Ser Glu Tyr
                                85                 90                 95
```

Val Phe Gly Ala Gly Thr Lys Val Thr Val Leu Gly
            100                 105

<210> SEQ ID NO 7
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 7

Asn Phe Met Leu Thr Gln Pro Pro Ser Val Ser Val Ser Pro Gly Lys
1               5                   10                  15

Thr Ala Arg Ile Thr Cys Arg Gly Asp Asn Leu Gly Asp Val Asn Val
            20                  25                  30

His Trp Tyr Gln Gln Arg Pro Gly Gln Ala Pro Val Leu Val Met Tyr
        35                  40                  45

Tyr Asp Ala Asp Arg Pro Ser Gly Ile Pro Glu Arg Phe Ser Gly Ser
    50                  55                  60

Asn Ser Gly Asn Thr Ala Ile Leu Thr Ile Ser Gly Val Glu Ala Gly
65                  70                  75                  80

Asp Glu Ala Asp Tyr Tyr Cys Gln Val Trp Asp Arg Thr Ser Glu Tyr
                85                  90                  95

Val Phe Gly Thr Gly Thr Lys Val Thr Val Leu Gly
            100                 105

<210> SEQ ID NO 8
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 8

Asn Phe Met Leu Thr Gln Pro Ser Ser Val Ser Val Ser Pro Gly Lys
1               5                   10                  15

Thr Ala Arg Ile Thr Cys Arg Gly Asp Asn Leu Gly Asp Val Asn Val
            20                  25                  30

His Trp Tyr Gln Gln Arg Pro Gly Gln Ala Pro Val Leu Val Met Tyr
        35                  40                  45

Tyr Asp Ala Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Arg Thr Ser Glu Tyr
                85                  90                  95

Val Phe Gly Thr Gly Thr Lys Val Thr Val Leu Gly
            100                 105

<210> SEQ ID NO 9
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 9

Asn Phe Met Leu Thr Gln Pro His Ser Val Ser Val Ser Pro Gly Lys
1               5                   10                  15

Thr Ala Arg Ile Thr Cys Arg Gly Asp Asn Leu Gly Asp Val Asn Val

```
            20                  25                  30
His Trp Tyr Gln Gln Arg Pro Gly Gln Ala Pro Val Leu Val Met Tyr
            35                  40                  45

Tyr Asp Ala Asp Arg Pro Ser Gly Ile Pro Glu Arg Phe Ser Gly Ser
        50                  55                  60

Asn Ser Gly Asn Thr Ala Thr Leu Thr Ile Ser Gly Val Glu Ala Gly
 65                  70                  75                  80

Asp Glu Ala Asp Tyr Tyr Cys Gln Val Trp Asp Arg Thr Ser Glu Tyr
                85                  90                  95

Val Phe Gly Thr Gly Thr Lys Val Thr Val Leu Gly
            100                 105

<210> SEQ ID NO 10
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 10

Asn Phe Met Leu Thr Gln Pro Pro Ser Val Ser Val Ser Pro Gly Lys
 1               5                  10                  15

Thr Ala Arg Ile Thr Cys Arg Gly Asp Asn Leu Gly Asp Val Asn Val
            20                  25                  30

His Trp Tyr Gln Gln Arg Pro Gly Gln Ala Pro Val Leu Ile Met Tyr
            35                  40                  45

Tyr Asp Ala Asp Arg Pro Ser Gly Ile Pro Glu Arg Phe Ser Gly Ser
        50                  55                  60

Asn Ser Gly Asn Thr Ala Thr Leu Thr Ile Ser Gly Val Glu Ala Gly
 65                  70                  75                  80

Asp Glu Ala Asp Tyr Tyr Cys Gln Val Trp Asp Arg Thr Ser Glu Tyr
                85                  90                  95

Val Phe Gly Thr Gly Thr Lys Val Thr Val Leu Gly
            100                 105

<210> SEQ ID NO 11
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 11

Asn Phe Met Leu Thr Gln Pro Pro Ser Val Ser Val Ser Pro Gly Lys
 1               5                  10                  15

Thr Ala Arg Ile Thr Cys Met Gly Asp Asn Leu Gly Asp Val Asn Val
            20                  25                  30

His Trp Tyr Gln Gln Arg Pro Gly Gln Ala Pro Val Leu Val Met Tyr
            35                  40                  45

Tyr Asp Ala Asp Arg Pro Ser Gly Ile Pro Glu Arg Phe Ser Gly Ser
        50                  55                  60

Asn Ser Gly Asn Thr Ala Thr Leu Thr Ile Ser Gly Val Glu Ala Gly
 65                  70                  75                  80

Asp Glu Ala Asp Tyr Tyr Cys Gln Val Trp Asp Arg Thr Ser Glu Tyr
                85                  90                  95

Val Phe Gly Thr Gly Thr Lys Val Thr Val Leu Gly
            100                 105
```

<210> SEQ ID NO 12
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 12

Asn Phe Met Leu Thr Gln Pro Ser Ser Val Ser Val Pro Pro Gly Lys
1               5                   10                  15

Thr Ala Arg Ile Thr Cys Arg Gly Asp Asn Leu Gly Asp Val Asn Val
            20                  25                  30

His Trp Tyr Gln Gln Arg Gly Gln Ala Pro Val Leu Val Met Tyr
        35                  40                  45

Tyr Asp Ala Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Arg Thr Ser Glu Phe
                85                  90                  95

Val Phe Gly Thr Gly Thr Lys Val Thr Val Leu Gly
            100                 105

<210> SEQ ID NO 13
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 13

Asn Phe Met Leu Thr Gln Pro Pro Ser Leu Ser Val Ser Pro Gly Gln
1               5                   10                  15

Thr Ala Arg Ile Thr Cys Arg Gly Asp Asn Leu Gly Asp Val Asn Val
            20                  25                  30

His Trp Tyr Gln Gln Arg Pro Gly Gln Ala Pro Val Leu Val Met Tyr
        35                  40                  45

Tyr Asp Ala Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Arg Thr Ser Glu Tyr
                85                  90                  95

Val Phe Gly Thr Gly Thr Lys Val Thr Val Leu Gly
            100                 105

<210> SEQ ID NO 14
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 14

Asn Phe Met Leu Thr Gln Pro Pro Ser Val Ser Val Ala Pro Gly Gln
1               5                   10                  15

Thr Ala Arg Ile Thr Cys Arg Gly Asp Asn Leu Gly Asp Val Asn Val
            20                  25                  30

His Trp Tyr Gln Gln Arg Pro Gly Gln Ala Pro Val Leu Val Met Tyr

```
                35                  40                  45
Tyr Asp Ala Asp Arg Pro Ser Gly Ile Pro Glu Arg Phe Ser Gly Ser
         50                  55                  60
Asn Ser Gly Asn Thr Ala Thr Leu Thr Ile Ser Gly Val Glu Ala Gly
 65                  70                  75                  80
Asp Glu Ala Asp Tyr Tyr Cys Gln Val Trp Asp Arg Thr Ser Glu Tyr
                 85                  90                  95
Val Phe Gly Thr Gly Thr Lys Val Thr Val Leu Gly
            100                 105
```

<210> SEQ ID NO 15
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 15

```
Asn Phe Met Leu Thr Gln Pro Pro Ala Val Ser Val Ser Pro Gly Lys
  1               5                  10                  15
Thr Ala Arg Ile Thr Cys Arg Gly Asp Asn Leu Gly Asp Val Asn Val
             20                  25                  30
His Trp Tyr Gln Gln Arg Pro Gly Gln Ala Pro Val Leu Val Met Tyr
         35                  40                  45
Tyr Asp Ala Asp Arg Pro Ser Gly Ile Pro Glu Arg Phe Ser Gly Ser
     50                  55                  60
Asn Ser Gly Asn Thr Ala Thr Leu Thr Ile Ser Gly Val Glu Ala Gly
 65                  70                  75                  80
Asp Glu Ala Asp Tyr Tyr Cys Gln Val Trp Asp Arg Thr Ser Glu Tyr
                 85                  90                  95
Val Phe Gly Thr Gly Thr Lys Val Thr Val Leu Gly
            100                 105
```

<210> SEQ ID NO 16
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 16

```
Asn Phe Met Leu Thr Gln Pro Pro Ser Val Ser Val Ser Pro Gly Lys
  1               5                  10                  15
Thr Ala Arg Ile Thr Cys Arg Gly Asp Asn Leu Gly Asp Val Asn Val
             20                  25                  30
His Trp Tyr Gln Gln Arg Pro Gly Gln Ala Pro Val Leu Val Met Tyr
         35                  40                  45
Tyr Asp Ala Asp Arg Pro Ser Gly Ile Pro Lys Arg Phe Ser Gly Ser
     50                  55                  60
Asn Ser Gly Asn Thr Ala Thr Leu Thr Ile Ser Gly Val Glu Ala Gly
 65                  70                  75                  80
Asp Glu Ala Asp Tyr Tyr Cys Gln Val Trp Asp Arg Thr Ser Glu Tyr
                 85                  90                  95
Val Phe Gly Thr Gly Thr Lys Val Thr Val Leu Gly
            100                 105
```

<210> SEQ ID NO 17
<211> LENGTH: 108

```
<212> TYPE: PRT
<213> ORGANISM: Artificial Sequence
<220> FEATURE:
<223> OTHER INFORMATION: Antibody light chain variable region

<400> SEQUENCE: 17

Asn Phe Met Leu Thr Gln Pro Pro Ser Val Ser Val Ser Pro Gly Lys
1               5                   10                  15

Thr Ala Arg Ile Thr Cys Arg Gly Asp Asn Leu Gly Asp Val Asn Val
            20                  25                  30

His Trp Tyr Gln Gln Arg Pro Gly Gln Ala Pro Val Leu Val Ile Tyr
        35                  40                  45

Tyr Asp Ala Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Arg Thr Ser Glu Tyr
                85                  90                  95

Val Phe Gly Thr Gly Thr Lys Val Thr Val Leu Gly
            100                 105

<210> SEQ ID NO 18
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 18

Asn Phe Met Leu Thr Gln Pro Pro Ser Val Ser Val Ser Pro Gly Lys
1               5                   10                  15

Thr Ala Arg Ile Thr Cys Arg Gly Asp Asn Leu Gly Asp Val Asn Val
            20                  25                  30

His Trp Tyr Gln Gln Arg Pro Gly Gln Ala Pro Val Leu Val Met Tyr
        35                  40                  45

Tyr Asp Ala Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Arg Thr Asn Glu Tyr
                85                  90                  95

Val Phe Gly Thr Gly Thr Lys Val Thr Val Leu Gly
            100                 105

<210> SEQ ID NO 19
<211> LENGTH: 108
<212> TYPE: PRT
<213> ORGANISM: Artificial Sequence
<220> FEATURE:
<223> OTHER INFORMATION: Antibody light chain variable region

<400> SEQUENCE: 19

Gln Phe Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
```

```
                    50                  55                  60
Asn Phe Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Arg Asp Tyr
                 85                  90                  95

Val Phe Gly Thr Gly Thr Lys Val Thr Val Leu Gly
            100                 105
```

<210> SEQ ID NO 20
<211> LENGTH: 121
<212> TYPE: PRT
<213> ORGANISM: Artificial Sequence
<220> FEATURE:
<223> OTHER INFORMATION: Antibody heavy chain variable region

<400> SEQUENCE: 20

```
Gln Met Gln Leu Val Gln Ser Gly Ala Glu Val Lys Lys Pro Gly Ala
  1               5                  10                  15

Ser Val Lys Leu Ser Cys Lys Ala Ser Gly Tyr Thr Phe Ser Ser Tyr
             20                  25                  30

Trp Met His Trp Val Arg Gln Ala Pro Gly Gln Arg Leu Glu Trp Met
         35                  40                  45

Gly Glu Ile Asn Pro Gly Asn Gly His Thr Asn Tyr Asn Glu Lys Phe
     50                  55                  60

Lys Ser Arg Val Thr Ile Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Ile Trp Gly Pro Ser Leu Thr Ser Pro Phe Asp Tyr Trp Gly
            100                 105                 110

Gln Gly Thr Leu Val Thr Val Ser Ser
        115                 120
```

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
cgcggatcca tggagagcaa                                            20

<210> SEQ ID NO 22
<211> LENGTH: 27
<212> TYPE: DNA
<213> ORGANISM: Artificial Sequence
<220> FEATURE:
<223> OTHER INFORMATION: primer

<400> SEQUENCE: 22
ccgctagctt tttcatggac cctgaca                                    27

<210> SEQ ID NO 23
<211> LENGTH: 44
<212> TYPE: DNA
<213> ORGANISM: Artificial Sequence
<220> FEATURE:
<223> OTHER INFORMATION: primer

<400> SEQUENCE: 23
ccgctagcag cggcctggtg ccgcgcggca gcgacaaaac tcac    44

<210> SEQ ID NO 24
<211> LENGTH: 53
<212> TYPE: DNA
<213> ORGANISM: Artificial Sequence
<220> FEATURE:
<223> OTHER INFORMATION: primer

<400> SEQUENCE: 24
ggctcgagtc acaggtcttc ctcagagatc agcttctgct cttacccgga gac    53

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cgcggatcca tggagagcaa    20

<210> SEQ ID NO 26
<211> LENGTH: 28
<212> TYPE: DNA
<213> ORGANISM: Artificial Sequence
<220> FEATURE:
<223> OTHER INFORMATION: primer

<400> SEQUENCE: 26
ctagctagcc ctatacccta caacgaca    28

<210> SEQ ID NO 27
<211> LENGTH: 40
<212> TYPE: DNA
<213> ORGANISM: Artificial Sequence
<220> FEATURE:
<223> OTHER INFORMATION: primer

<400> SEQUENCE: 27
gacccgggcc gcctctgtgg gttatgttca agattacaga    40

<210> SEQ ID NO 28
<211> LENGTH: 28
<212> TYPE: DNA
<213> ORGANISM: Artificial Sequence
<220> FEATURE:
<223> OTHER INFORMATION: primer

<400> SEQUENCE: 28
ctagctagct ttttcatgga ccctgaca    28

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
gargtgcagc tggtggagtc    20

<210> SEQ ID NO 30
<211> LENGTH: 20
<212> TYPE: DNA
<213> ORGANISM: Artificial Sequence

```
<220> FEATURE:
<223> OTHER INFORMATION: primer

<400> SEQUENCE: 30
cagstgcagc tgcaggagtc                                               20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
caggtacagc tgcagcagtc                                               20

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
cagrtgcagc tggtgcagtc tgggg                                         25

<210> SEQ ID NO 33
<211> LENGTH: 27
<212> TYPE: DNA
<213> ORGANISM: Artificial Sequence
<220> FEATURE:
<223> OTHER INFORMATION: primer

<400> SEQUENCE: 33
gaggtgcagc tggtgcagtc tggagca                                       27

<210> SEQ ID NO 34
<211> LENGTH: 25
<212> TYPE: DNA
<213> ORGANISM: Artificial Sequence
<220> FEATURE:
<223> OTHER INFORMATION: primer

<400> SEQUENCE: 34
caggttcagc tggtgcagtc tggag                                         25

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
caggttcagc tggtgcagtc tgggg                                         25

<210> SEQ ID NO 36
<211> LENGTH: 25
<212> TYPE: DNA
<213> ORGANISM: Artificial Sequence
<220> FEATURE:
<223> OTHER INFORMATION: primer

<400> SEQUENCE: 36
caggtccagc tggtacagtc tgggg                                         25
```

```
<210> SEQ ID NO 37
<211> LENGTH: 29
<212> TYPE: DNA
<213> ORGANISM: Artificial Sequence
<220> FEATURE:
<223> OTHER INFORMATION: primer

<400> SEQUENCE: 37
caggtcacct tgaaggagtc tggtcctgt                                29

<210> SEQ ID NO 38
<211> LENGTH: 29
<212> TYPE: DNA
<213> ORGANISM: Artificial Sequence
<220> FEATURE:
<223> OTHER INFORMATION: primer

<400> SEQUENCE: 38
cagatcacct tgaaggagtc tggtcctac                                29

<210> SEQ ID NO 39
<211> LENGTH: 29
<212> TYPE: DNA
<213> ORGANISM: Artificial Sequence
<220> FEATURE:
<223> OTHER INFORMATION: primer

<400> SEQUENCE: 39
caggtcacct tgagggagtc tggtcctgc                                29

<210> SEQ ID NO 40
<211> LENGTH: 31
<212> TYPE: DNA
<213> ORGANISM: Artificial Sequence
<220> FEATURE:
<223> OTHER INFORMATION: primer

<400> SEQUENCE: 40
gaggtgcagc tggtggagtc tgggggaggt g                             31

<210> SEQ ID NO 41
<211> LENGTH: 25
<212> TYPE: DNA
<213> ORGANISM: Artificial Sequence
<220> FEATURE:
<223> OTHER INFORMATION: primer

<400> SEQUENCE: 41
caggtgcagc tacagcagtg gggcg                                    25

<210> SEQ ID NO 42
<211> LENGTH: 24
<212> TYPE: DNA
<213> ORGANISM: Artificial Sequence
<220> FEATURE:
<223> OTHER INFORMATION: primer

<400> SEQUENCE: 42
aatacacggc cgtgtcctca gatc                                     24

<210> SEQ ID NO 43
<211> LENGTH: 53
<212> TYPE: DNA
<213> ORGANISM: Artificial Sequence
<220> FEATURE:
<223> OTHER INFORMATION: primer
```

<400> SEQUENCE: 43
aatacacggc cgtgtcctca gatctcaggc tgctcagctc catgtaggct gag  53

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
agctccatgt aggctgtgtc t  21

<210> SEQ ID NO 45
<211> LENGTH: 28
<212> TYPE: DNA
<213> ORGANISM: Artificial Sequence
<220> FEATURE:
<223> OTHER INFORMATION: primer

<400> SEQUENCE: 45
agctccatgt aggctgtgct catagacc  28

<210> SEQ ID NO 46
<211> LENGTH: 28
<212> TYPE: DNA
<213> ORGANISM: Artificial Sequence
<220> FEATURE:
<223> OTHER INFORMATION: primer

<400> SEQUENCE: 46
agctccatgt aggctgtgct tgtggaca  28

<210> SEQ ID NO 47
<211> LENGTH: 27
<212> TYPE: DNA
<213> ORGANISM: Artificial Sequence
<220> FEATURE:
<223> OTHER INFORMATION: primer

<400> SEQUENCE: 47
agctccatgt aggctgtgct tatggag  27

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
aaggaccacc tgcttttgga gg  22

<210> SEQ ID NO 49
<211> LENGTH: 38
<212> TYPE: DNA
<213> ORGANISM: Artificial Sequence
<220> FEATURE:
<223> OTHER INFORMATION: primer

<400> SEQUENCE: 49
aatacacggc cgtgtcctcg gctctcagac tgttcatt  38

<210> SEQ ID NO 50

```
<211> LENGTH: 23
<212> TYPE: DNA
<213> ORGANISM: Artificial Sequence
<220> FEATURE:
<223> OTHER INFORMATION: primer

<400> SEQUENCE: 50
aatacacggc ctgtccacgg cgg                                           23

<210> SEQ ID NO 51
<211> LENGTH: 24
<212> TYPE: DNA
<213> ORGANISM: Artificial Sequence
<220> FEATURE:
<223> OTHER INFORMATION: primer

<400> SEQUENCE: 51
aatacatggc ggtgtccgag gcct                                          24

<210> SEQ ID NO 52
<211> LENGTH: 29
<212> TYPE: DNA
<213> ORGANISM: Artificial Sequence
<220> FEATURE:
<223> OTHER INFORMATION: primer

<400> SEQUENCE: 52
gatctgagga cacggccgtg tattactgt                                     29

<210> SEQ ID NO 53
<211> LENGTH: 23
<212> TYPE: DNA
<213> ORGANISM: Artificial Sequence
<220> FEATURE:
<223> OTHER INFORMATION: primer

<400> SEQUENCE: 53
cctccaaaag ccaggtggtc ctt                                           23

<210> SEQ ID NO 54
<211> LENGTH: 29
<212> TYPE: DNA
<213> ORGANISM: Artificial Sequence
<220> FEATURE:
<223> OTHER INFORMATION: primer

<400> SEQUENCE: 54
gagccgagga cacggccgtg tattactgt                                     29

<210> SEQ ID NO 55
<211> LENGTH: 29
<212> TYPE: DNA
<213> ORGANISM: Artificial Sequence
<220> FEATURE:
<223> OTHER INFORMATION: primer

<400> SEQUENCE: 55
ccgccgtgga cacggccgtg tattactgt                                     29

<210> SEQ ID NO 56
<211> LENGTH: 29
<212> TYPE: DNA
<213> ORGANISM: Artificial Sequence
<220> FEATURE:
<223> OTHER INFORMATION: primer

<400> SEQUENCE: 56
```

```
aggcctcgga caccgccatg tattactgt                                     29

<210> SEQ ID NO 57
<211> LENGTH: 17
<212> TYPE: DNA
<213> ORGANISM: Artificial Sequence
<220> FEATURE:
<223> OTHER INFORMATION: primer

<400> SEQUENCE: 57
ctgaggagac ggtgacc                                                  17

<210> SEQ ID NO 58
<211> LENGTH: 44
<212> TYPE: DNA
<213> ORGANISM: Artificial Sequence
<220> FEATURE:
<223> OTHER INFORMATION: primer

<400> SEQUENCE: 58
gcgatggccc agccggccat ggcccagrtg cagctggtrs agtc                    44

<210> SEQ ID NO 59
<211> LENGTH: 44
<212> TYPE: DNA
<213> ORGANISM: Artificial Sequence
<220> FEATURE:
<223> OTHER INFORMATION: primer

<400> SEQUENCE: 59
gcgatggccc agccggccat ggcccagrtc accttgargg agtc                    44

<210> SEQ ID NO 60
<211> LENGTH: 43
<212> TYPE: DNA
<213> ORGANISM: Artificial Sequence
<220> FEATURE:
<223> OTHER INFORMATION: primer

<400> SEQUENCE: 60
gcgatggccc agccggccat ggcccaggtr cagctrcags agt                     43

<210> SEQ ID NO 61
<211> LENGTH: 36
<212> TYPE: DNA
<213> ORGANISM: Artificial Sequence
<220> FEATURE:
<223> OTHER INFORMATION: primer

<400> SEQUENCE: 61
ggaattcggc cccgaggcc tgargagacr gtgacc                              36

<210> SEQ ID NO 62
<211> LENGTH: 18
<212> TYPE: DNA
<213> ORGANISM: Artificial Sequence
<220> FEATURE:
<223> OTHER INFORMATION: primer

<400> SEQUENCE: 62
cagyctgtgc tgactcag                                                 18

<210> SEQ ID NO 63
<211> LENGTH: 19
<212> TYPE: DNA
```

<213> ORGANISM: Artificial Sequence
<220> FEATURE:
<223> OTHER INFORMATION: primer

<400> SEQUENCE: 63
cagcctgtgc tgactcaat                                            19

<210> SEQ ID NO 64
<211> LENGTH: 18
<212> TYPE: DNA
<213> ORGANISM: Artificial Sequence
<220> FEATURE:
<223> OTHER INFORMATION: primer

<400> SEQUENCE: 64
tcctatgagc tgacwcag                                             18

<210> SEQ ID NO 65
<211> LENGTH: 22
<212> TYPE: DNA
<213> ORGANISM: Artificial Sequence
<220> FEATURE:
<223> OTHER INFORMATION: primer

<400> SEQUENCE: 65
cagyctgtgc tgactcagcc gt                                        22

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
cagtctgtgc tgacgcagcc g                                         21

<210> SEQ ID NO 67
<211> LENGTH: 22
<212> TYPE: DNA
<213> ORGANISM: Artificial Sequence
<220> FEATURE:
<223> OTHER INFORMATION: primer

<400> SEQUENCE: 67
cagtctgccc tgactcagcc tc                                        22

<210> SEQ ID NO 68
<211> LENGTH: 22
<212> TYPE: DNA
<213> ORGANISM: Artificial Sequence
<220> FEATURE:
<223> OTHER INFORMATION: primer

<400> SEQUENCE: 68
cagtctgccc tgactcagcc tg                                        22

<210> SEQ ID NO 69
<211> LENGTH: 28
<212> TYPE: DNA
<213> ORGANISM: Artificial Sequence
<220> FEATURE:
<223> OTHER INFORMATION: primer

<400> SEQUENCE: 69
cagrctgtgg tgacycagga gccctcac                                  28

<210> SEQ ID NO 70
<211> LENGTH: 28
<212> TYPE: DNA
<213> ORGANISM: Artificial Sequence
<220> FEATURE:
<223> OTHER INFORMATION: primer

<400> SEQUENCE: 70
cagrctgtgg tgacycagga gccatcgt                                    28

<210> SEQ ID NO 71
<211> LENGTH: 23
<212> TYPE: DNA
<213> ORGANISM: Artificial Sequence
<220> FEATURE:
<223> OTHER INFORMATION: primer

<400> SEQUENCE: 71
tcctatgagc tgacwcagcc act                                         23

<210> SEQ ID NO 72
<211> LENGTH: 21
<212> TYPE: DNA
<213> ORGANISM: Artificial Sequence
<220> FEATURE:
<223> OTHER INFORMATION: primer

<400> SEQUENCE: 72
aattttatgc tgactcagcc c                                           21

<210> SEQ ID NO 73
<211> LENGTH: 36
<212> TYPE: DNA
<213> ORGANISM: Artificial Sequence
<220> FEATURE:
<223> OTHER INFORMATION: primer

<400> SEQUENCE: 73
cctcctccac ctaggacggt gaccttggtc ccagtt                           36

<210> SEQ ID NO 74
<211> LENGTH: 36
<212> TYPE: DNA
<213> ORGANISM: Artificial Sequence
<220> FEATURE:
<223> OTHER INFORMATION: primer

<400> SEQUENCE: 74
cctcctccac ctaggacggt cagcttggtc cctccg                           36

<210> SEQ ID NO 75
<211> LENGTH: 36
<212> TYPE: DNA
<213> ORGANISM: Artificial Sequence
<220> FEATURE:
<223> OTHER INFORMATION: primer

<400> SEQUENCE: 75
cctcctccac cgagggcggt cagctgggtg cctcct                           36

<210> SEQ ID NO 76
<211> LENGTH: 45
<212> TYPE: DNA
<213> ORGANISM: Artificial Sequence
<220> FEATURE:

<223> OTHER INFORMATION: primer

<400> SEQUENCE: 76
ggtggatcca gcggtgtggg ttccaatttt atgctgactc agccc     45

<210> SEQ ID NO 77
<211> LENGTH: 44
<212> TYPE: DNA
<213> ORGANISM: Artificial Sequence
<220> FEATURE:
<223> OTHER INFORMATION: primer

<400> SEQUENCE: 77
ggtggatcca gcggtgtggg ttcccagyct gtgctgactc agcc     44

<210> SEQ ID NO 78
<211> LENGTH: 44
<212> TYPE: DNA
<213> ORGANISM: Artificial Sequence
<220> FEATURE:
<223> OTHER INFORMATION: primer

<400> SEQUENCE: 78
ggtggatcca gcggtgtggg ttcccagcct gtgctgactc aatc     44

<210> SEQ ID NO 79
<211> LENGTH: 44
<212> TYPE: DNA
<213> ORGANISM: Artificial Sequence
<220> FEATURE:
<223> OTHER INFORMATION: primer

<400> SEQUENCE: 79
ggtggatcca gcggtgtggg ttcccagtct gccctgactc agcc     44

<210> SEQ ID NO 80
<211> LENGTH: 44
<212> TYPE: DNA
<213> ORGANISM: Artificial Sequence
<220> FEATURE:
<223> OTHER INFORMATION: primer

<400> SEQUENCE: 80
ggtggatcca gcggtgtggg ttcccagrct gtggtgacyc agga     44

<210> SEQ ID NO 81
<211> LENGTH: 42
<212> TYPE: DNA
<213> ORGANISM: Artificial Sequence
<220> FEATURE:
<223> OTHER INFORMATION: primer

<400> SEQUENCE: 81
ggtggatcca gcggtgtggg ttcctcctat gagctgacwc ag     42

<210> SEQ ID NO 82
<211> LENGTH: 36
<212> TYPE: DNA
<213> ORGANISM: Artificial Sequence
<220> FEATURE:
<223> OTHER INFORMATION: primer

<400> SEQUENCE: 82
gaattccacg aggctggctc ctccacckag grcggt     36

```
<210> SEQ ID NO 83
<211> LENGTH: 31
<212> TYPE: DNA
<213> ORGANISM: Artificial Sequence
<220> FEATURE:
<223> OTHER INFORMATION: primer

<400> SEQUENCE: 83
gacatccaga tgacccagtc tccatcctcc c                           31

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84
gacatccaga tgacccagtc tccatcctca                             30

<210> SEQ ID NO 85
<211> LENGTH: 31
<212> TYPE: DNA
<213> ORGANISM: Artificial Sequence
<220> FEATURE:
<223> OTHER INFORMATION: primer

<400> SEQUENCE: 85
gacatccaga tgacccagtc tccatcttcy g                           31

<210> SEQ ID NO 86
<211> LENGTH: 28
<212> TYPE: DNA
<213> ORGANISM: Artificial Sequence
<220> FEATURE:
<223> OTHER INFORMATION: primer

<400> SEQUENCE: 86
gacatccaga tgacccagtc tccttcca                               28

<210> SEQ ID NO 87
<211> LENGTH: 31
<212> TYPE: DNA
<213> ORGANISM: Artificial Sequence
<220> FEATURE:
<223> OTHER INFORMATION: primer

<400> SEQUENCE: 87
aacatccaga tgacccagtc tccatctgcc a                           31

<210> SEQ ID NO 88
<211> LENGTH: 29
<212> TYPE: DNA
<213> ORGANISM: Artificial Sequence
<220> FEATURE:
<223> OTHER INFORMATION: primer

<400> SEQUENCE: 88
aacatccaga tgacccagtc tccatcctt                              29

<210> SEQ ID NO 89
<211> LENGTH: 25
<212> TYPE: DNA
<213> ORGANISM: Artificial Sequence
<220> FEATURE:
<223> OTHER INFORMATION: primer
```

-continued

<400> SEQUENCE: 89
gccatccagt tgacccagtc tccat                                          25

<210> SEQ ID NO 90
<211> LENGTH: 30
<212> TYPE: DNA
<213> ORGANISM: Artificial Sequence
<220> FEATURE:
<223> OTHER INFORMATION: primer

<400> SEQUENCE: 90
gccatccgga tgacccagtc tccattctcc                                     30

<210> SEQ ID NO 91
<211> LENGTH: 30
<212> TYPE: DNA
<213> ORGANISM: Artificial Sequence
<220> FEATURE:
<223> OTHER INFORMATION: primer

<400> SEQUENCE: 91
gtcatctgga tgacccagtc tccatccttα                                     30

<210> SEQ ID NO 92
<211> LENGTH: 34
<212> TYPE: DNA
<213> ORGANISM: Artificial Sequence
<220> FEATURE:
<223> OTHER INFORMATION: primer

<400> SEQUENCE: 92
gatattgtga tgacccagac tccactctct ctgt                                34

<210> SEQ ID NO 93
<211> LENGTH: 34
<212> TYPE: DNA
<213> ORGANISM: Artificial Sequence
<220> FEATURE:
<223> OTHER INFORMATION: primer

<400> SEQUENCE: 93
gatattgtga tgacccagac tccactctcc ctgc                                34

<210> SEQ ID NO 94
<211> LENGTH: 33
<212> TYPE: DNA
<213> ORGANISM: Artificial Sequence
<220> FEATURE:
<223> OTHER INFORMATION: primer

<400> SEQUENCE: 94
gatattgtga tgacccagac tccactctcc tca                                 33

<210> SEQ ID NO 95
<211> LENGTH: 29
<212> TYPE: DNA
<213> ORGANISM: Artificial Sequence
<220> FEATURE:
<223> OTHER INFORMATION: primer

<400> SEQUENCE: 95
gatrttgtga tgactcagtc tccactctc                                      29

<210> SEQ ID NO 96
<211> LENGTH: 25

<212> TYPE: DNA
<213> ORGANISM: Artificial Sequence
<220> FEATURE:
<223> OTHER INFORMATION: primer

<400> SEQUENCE: 96
gaaattgtgt tgacrcagtc tccag                                          25

<210> SEQ ID NO 97
<211> LENGTH: 25
<212> TYPE: DNA
<213> ORGANISM: Artificial Sequence
<220> FEATURE:
<223> OTHER INFORMATION: primer

<400> SEQUENCE: 97
gacatcgtga tgacccagtc tccag                                          25

<210> SEQ ID NO 98
<211> LENGTH: 49
<212> TYPE: DNA
<213> ORGANISM: Artificial Sequence
<220> FEATURE:
<223> OTHER INFORMATION: primer

<400> SEQUENCE: 98
gatgttgtga tgactcagtc tccactctcc ctgcccgtca cccttggac                49

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
gaaattgtgc tgactcagtc tccagacttt                                     30

<210> SEQ ID NO 100
<211> LENGTH: 49
<212> TYPE: DNA
<213> ORGANISM: Artificial Sequence
<220> FEATURE:
<223> OTHER INFORMATION: primer

<400> SEQUENCE: 100
gacatccaga tgacccagtc tccatcctcc ctgtctgcat ctgtaggag                49

<210> SEQ ID NO 101
<211> LENGTH: 33
<212> TYPE: DNA
<213> ORGANISM: Artificial Sequence
<220> FEATURE:
<223> OTHER INFORMATION: primer

<400> SEQUENCE: 101
tcctccacgt ttgatttcca ccttggtccc ttg                                 33

<210> SEQ ID NO 102
<211> LENGTH: 31
<212> TYPE: DNA
<213> ORGANISM: Artificial Sequence
<220> FEATURE:
<223> OTHER INFORMATION: primer

<400> SEQUENCE: 102

```
tcctccacgt ttgatctcca gcttggtccc c                                    31
```

<210> SEQ ID NO 103
<211> LENGTH: 32
<212> TYPE: DNA
<213> ORGANISM: Artificial Sequence
<220> FEATURE:
<223> OTHER INFORMATION: primer

<400> SEQUENCE: 103

```
tcctccacgt ttgatatcca ctttggtccc ag                                   32
```

<210> SEQ ID NO 104
<211> LENGTH: 33
<212> TYPE: DNA
<213> ORGANISM: Artificial Sequence
<220> FEATURE:
<223> OTHER INFORMATION: primer

<400> SEQUENCE: 104

```
tcctccacgt ttgatctcca ccttggtccc tcc                                  33
```

<210> SEQ ID NO 105
<211> LENGTH: 31
<212> TYPE: DNA
<213> ORGANISM: Artificial Sequence
<220> FEATURE:
<223> OTHER INFORMATION: primer

<400> SEQUENCE: 105

```
tcctccacgt ttaatctcca gtcgtgtccc t                                    31
```

<210> SEQ ID NO 106
<211> LENGTH: 47
<212> TYPE: DNA
<213> ORGANISM: Artificial Sequence
<220> FEATURE:
<223> OTHER INFORMATION: primer

<400> SEQUENCE: 106

```
ggtggatcca gcggtgtggg ttccgacatc cagatgaccc agtctcc                   47
```

<210> SEQ ID NO 107
<211> LENGTH: 47
<212> TYPE: DNA
<213> ORGANISM: Artificial Sequence
<220> FEATURE:
<223> OTHER INFORMATION: primer

<400> SEQUENCE: 107

```
ggtggatcca gcggtgtggg ttccgatatt gtgatgaccc agwctcc                   47
```

<210> SEQ ID NO 108
<211> LENGTH: 38
<212> TYPE: DNA
<213> ORGANISM: Artificial Sequence
<220> FEATURE:
<223> OTHER INFORMATION: primer

<400> SEQUENCE: 108

```
gaattccacg aggctggctc ctccacgttt gathtcca                             38
```

<210> SEQ ID NO 109
<211> LENGTH: 18
<212> TYPE: DNA
<213> ORGANISM: Artificial Sequence

```
<220> FEATURE:
<223> OTHER INFORMATION: primer

<400> SEQUENCE: 109
cgaatttcta gataacga                                               18

<210> SEQ ID NO 110
<211> LENGTH: 41
<212> TYPE: DNA
<213> ORGANISM: Artificial Sequence
<220> FEATURE:
<223> OTHER INFORMATION: primer

<400> SEQUENCE: 110
cctccgccac tacctcctcc tccgaggccc ccgaggcctg a                     41

<210> SEQ ID NO 111
<211> LENGTH: 54
<212> TYPE: DNA
<213> ORGANISM: Artificial Sequence
<220> FEATURE:
<223> OTHER INFORMATION: primer

<400> SEQUENCE: 111
ggtagtggcg gaggaggctc cggtggatcc agcggtgtgg gttccgatat tgtg       54

<210> SEQ ID NO 112
<211> LENGTH: 40
<212> TYPE: DNA
<213> ORGANISM: Artificial Sequence
<220> FEATURE:
<223> OTHER INFORMATION: primer

<400> SEQUENCE: 112
ctcgaattcc cacgaggctg gctcctccac gtttgatttc                       40

<210> SEQ ID NO 113
<211> LENGTH: 15
<212> TYPE: DNA
<213> ORGANISM: Artificial Sequence
<220> FEATURE:
<223> OTHER INFORMATION: antibody heavy chain complementarity
      determining region

<400> SEQUENCE: 113
agctactgga tgcac                                                  15

<210> SEQ ID NO 114
<211> LENGTH: 5
<212> TYPE: PRT
<213> ORGANISM: Artificial Sequence
<220> FEATURE:
<223> OTHER INFORMATION: antibody heavy chain complementarity
      determining region

<400> SEQUENCE: 114

Ser Tyr Trp Met His
1               5

<210> SEQ ID NO 115
<211> LENGTH: 48
<212> TYPE: DNA
<213> ORGANISM: Artificial Sequence
<220> FEATURE:
<223> OTHER INFORMATION: antibody heavy chain complementarity
      determining region
```

<400> SEQUENCE: 115
gagattaatc ctggcaacgg tcataactac aacgagaagt tcaagtca         48

<210> SEQ ID NO 116
<211> LENGTH: 17
<212> TYPE: PRT
<213> ORGANISM: Artificial Sequence
<220> FEATURE:
<223> OTHER INFORMATION: antibody heavy chain complementarity
      determining region

<400> SEQUENCE: 116

Glu Ile Asn Pro Gly Asn Gly His Thr Asn Tyr Asn Glu Lys Phe Lys
1               5                   10                  15

Ser

<210> SEQ ID NO 117
<211> LENGTH: 36
<212> TYPE: DNA
<213> ORGANISM: Artificial Sequence
<220> FEATURE:
<223> OTHER INFORMATION: antibody heavy chain complementarity
      determining region

<400> SEQUENCE: 117
atttggggcc cgagtcttac ttctcccttt gactac                     36

<210> SEQ ID NO 118
<211> LENGTH: 12
<212> TYPE: PRT
<213> ORGANISM: Artificial Sequence
<220> FEATURE:
<223> OTHER INFORMATION: antibody heavy chain complementarity
      determining region

<400> SEQUENCE: 118

Ile Trp Gly Pro Ser Leu Thr Ser Pro Phe Asp Tyr
1               5                   10

<210> SEQ ID NO 119
<211> LENGTH: 33
<212> TYPE: DNA
<213> ORGANISM: Artificial Sequence
<220> FEATURE:
<223> OTHER INFORMATION: antibody light chain complementarity
      determining region

<400> SEQUENCE: 119
aggggagata accttggaga tgtaaatgtt cac                        33

<210> SEQ ID NO 120
<211> LENGTH: 11
<212> TYPE: PRT
<213> ORGANISM: Artificial Sequence
<220> FEATURE:
<223> OTHER INFORMATION: antibody light chain complementarity
      determining region

<400> SEQUENCE: 120

Arg Gly Asp Asn Leu Gly Asp Val Asn Val His
1               5                   10

<210> SEQ ID NO 121
<211> LENGTH: 21
<212> TYPE: DNA
<213> ORGANISM: Artificial Sequence

```
<220> FEATURE:
<223> OTHER INFORMATION: antibody light chain complementarity
      determining region

<400> SEQUENCE: 121
tatgatgccg accggccctc a                                              21

<210> SEQ ID NO 122
<211> LENGTH: 7
<212> TYPE: PRT
<213> ORGANISM: Artificial Sequence
<220> FEATURE:
<223> OTHER INFORMATION: antibody light chain complementarity
      determining region

<400> SEQUENCE: 122

Tyr Asp Ala Asp Arg Pro Ser
1               5

<210> SEQ ID NO 123
<211> LENGTH: 27
<212> TYPE: DNA
<213> ORGANISM: Artificial Sequence
<220> FEATURE:
<223> OTHER INFORMATION: antibody light chain complementarity
      determining region

<400> SEQUENCE: 123
caggtgtggg ataggactag tgagtat                                        27

<210> SEQ ID NO 124
<211> LENGTH: 10
<212> TYPE: PRT
<213> ORGANISM: Artificial Sequence
<220> FEATURE:
<223> OTHER INFORMATION: antibody light chain complementarity
      determining region

<400> SEQUENCE: 124

Gln Val Trp Asp Arg Thr Ser Glu Tyr Val
1               5                   10

<210> SEQ ID NO 125
<211> LENGTH: 363
<212> TYPE: DNA
<213> ORGANISM: Artificial Sequence
<220> FEATURE:
<223> OTHER INFORMATION: antibody heavy chain variable region

<400> SEQUENCE: 125
cagatgcagc tggtgcagtc tggggctgaa gtgaagaagc ctggggcttc agtgaagctg    60
tcctgcaagg cttctggcta caccttcagc agctactgga tgcactgggt gcgccaggcc   120
cctggacaac gccttgagtg gatgggagag attaatcctg caacggtca tactaactac    180 aacgagaagt tcaagtcacg cgtgacaatc actgtagaca atccgcgag cacagcctac    240 atggagctca gcagcctgag atctgaggac acggccgtgt attactgtgc gaaaatttgg   300
ggcccgagtc ttacttctcc ctttgactac tggggccagg gaaccctggt caccgtctcc   360
tca                                                                 363

<210> SEQ ID NO 126
<211> LENGTH: 121
<212> TYPE: PRT
<213> ORGANISM: Artificial Sequence
<220> FEATURE:
```

<223> OTHER INFORMATION: antibody light chain variable region

<400> SEQUENCE: 126

```
Gln Met Gln Leu Val Gln Ser Gly Ala Glu Val Lys Lys Pro Gly Ala
 1               5                  10                  15
Ser Val Lys Leu Ser Cys Lys Ala Ser Gly Tyr Thr Phe Ser Ser Tyr
            20                  25                  30
Trp Met His Trp Val Arg Gln Ala Pro Gly Gln Arg Leu Glu Trp Met
        35                  40                  45
Gly Glu Ile Asn Pro Gly Asn Gly His Thr Asn Tyr Asn Glu Lys Phe
    50                  55                  60
Lys Ser Arg Val Thr Ile Thr Val Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Lys Ile Trp Gly Pro Ser Leu Thr Ser Pro Phe Asp Tyr Trp Gly
            100                 105                 110
Gln Gly Thr Leu Val Thr Val Ser Ser
        115                 120
```

<210> SEQ ID NO 127
<211> LENGTH: 1443
<212> TYPE: DNA
<213> ORGANISM: Artificial Sequence
<220> FEATURE:
<223> OTHER INFORMATION: IgG antibody heavy chain variable region

<400> SEQUENCE: 127

```
atgggatgga gctatatcat cctcttttg gtagcaacag ctacagatgt ccactcggcc      60
cagccggcca tggcccagat gcagctggtg cagtctgggg ctgaagtgaa gaagcctggg    120
gcttcagtga agctgtcctg caaggcttct ggctacacct tcagcagcta ctggatgcac    180
tgggtgcgcc aggcccctgg acaacgcctt gagtggatgg gagagattaa tcctggcaac    240
ggtcatacta actacaacga gaagttcaag tcacgcgtga caatcactgt agacaaatcc    300
gcgagcacag cctacatgga gctcagcagc ctgagatctg aggacacggc cgtgtattac    360
tgtgcgaaaa tttggggccc gagtcttact tctccctttg actactgggg ccagggaacc    420
ctggtcaccg tctcctcagg cctcggggc ctcgctagca ccaagggccc atcggtcttc    480
cccctggcac cctcctccaa gagcacctct gggggcacag cggccctggg ctgcctggtc    540
aaggactact ccccgaacc ggtgacggtg tcgtggaact caggcgccct gaccagcggc    600
gtgcacacct tcccggctgt cctacagtcc tcaggactct actccctcag cagcgtggtg    660
accgtgccct ccagcagctt gggcacccag acctacatct gcaacgtgaa tcacaagccc    720
agcaacacca aggtggacaa gagagttgag cccaaatctt gtgacaaaac tcacacatgc    780
ccaccgtgcc cagcacctga actcctgggg ggaccgtcag tcttcctctt ccccccaaaa    840
cccaaggaca cctcatgat ctcccggacc cctgaggtca catgcgtggt ggtggacgtg    900
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggagtaca agtgcaaggt ctccaacaaa   1080
gccctcccag cccccatcga gaaaaccatc tccaaagcca aagggcagcc ccgagaacca   1140
caggtgtaca ccctgccccc atcccgggat gagctgacca agaaccaggt cagcctgacc   1200
tgcctggtca aaggcttcta tcccagcgac atcgccgtgg agtgggagag caatgggcag   1260
```

```
ccggagaaca actacaagac cacgcctccc gtgctggact ccgacggctc cttcttcctc      1320
tacagcaagc tcaccgtgga caagagcagg tggcagcagg ggaacgtctt ctcatgctcc      1380
gtgatgcatg aggctctgca caaccactac acgcagaaga gcctctccct gtctccgggt      1440
aaa                                                                   1443
```

<210> SEQ ID NO 128
<211> LENGTH: 481
<212> TYPE: PRT
<213> ORGANISM: Artificial Sequence
<220> FEATURE:
<223> OTHER INFORMATION: IgG antibody heavy chain variable region

<400> SEQUENCE: 128

```
Met Gly Trp Ser Tyr Ile Ile Leu Phe Leu Val Ala Thr Ala Thr Asp
 1               5                  10                  15

Val His Ser Ala Gln Pro Ala Met Ala Gln Met Gln Leu Val Gln Ser
            20                  25                  30

Gly Ala Glu Val Lys Lys Pro Gly Ala Ser Val Lys Leu Ser Cys Lys
        35                  40                  45

Ala Ser Gly Tyr Thr Phe Ser Ser Tyr Trp Met His Trp Val Arg Gln
    50                  55                  60

Ala Pro Gly Gln Arg Leu Glu Trp Met Gly Glu Ile Asn Pro Gly Asn
65                  70                  75                  80

Gly His Thr Asn Tyr Asn Glu Lys Phe Lys Ser Arg Val Thr Ile Thr
                85                  90                  95

Val Asp Lys Ser Ala Ser Thr Ala Tyr Met Glu Leu Ser Ser Leu Arg
           100                 105                 110

Ser Glu Asp Thr Ala Val Tyr Tyr Cys Ala Lys Ile Trp Gly Pro Ser
       115                 120                 125

Leu Thr Ser Pro Phe Asp Tyr Trp Gly Gln Gly Thr Leu Val Thr Val
   130                 135                 140

Ser Ser Gly Leu Gly Gly Leu Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Arg Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320
```

| | | | | | | | | | | | | | | | |
|---|---|---|---|---|---|---|---|---|---|---|---|---|---|---|---|
|Ala|Lys|Thr|Lys|Pro|Arg|Glu|Glu|Gln|Tyr|Asn|Ser|Thr|Tyr|Arg|Val|
| | | | |325| | | |330| | | |335| | | |

| | | | | | | | | | | | | | | | |
|---|---|---|---|---|---|---|---|---|---|---|---|---|---|---|---|
|Val|Ser|Val|Leu|Thr|Val|Leu|His|Gln|Asp|Trp|Leu|Asn|Gly|Lys|Glu|
| | | |340| | | |345| | | |350| | | | |

| | | | | | | | | | | | | | | | |
|---|---|---|---|---|---|---|---|---|---|---|---|---|---|---|---|
|Tyr|Lys|Cys|Lys|Val|Ser|Asn|Lys|Ala|Leu|Pro|Ala|Pro|Ile|Glu|Lys|
| | |355| | | |360| | | |365| | | | | |

| | | | | | | | | | | | | | | | |
|---|---|---|---|---|---|---|---|---|---|---|---|---|---|---|---|
|Thr|Ile|Ser|Lys|Ala|Lys|Gly|Gln|Pro|Arg|Glu|Pro|Gln|Val|Tyr|Thr|
| |370| | | |375| | | |380| | | | | | |

| | | | | | | | | | | | | | | | |
|---|---|---|---|---|---|---|---|---|---|---|---|---|---|---|---|
|Leu|Pro|Pro|Ser|Arg|Asp|Glu|Leu|Thr|Lys|Asn|Gln|Val|Ser|Leu|Thr|
|385| | | |390| | | |395| | | |400| | | |

| | | | | | | | | | | | | | | | |
|---|---|---|---|---|---|---|---|---|---|---|---|---|---|---|---|
|Cys|Leu|Val|Lys|Gly|Phe|Tyr|Pro|Ser|Asp|Ile|Ala|Val|Glu|Trp|Glu|
| | | |405| | | |410| | | |415| | | | |

| | | | | | | | | | | | | | | | |
|---|---|---|---|---|---|---|---|---|---|---|---|---|---|---|---|
|Ser|Asn|Gly|Gln|Pro|Glu|Asn|Asn|Tyr|Lys|Thr|Thr|Pro|Pro|Val|Leu|
| | |420| | | |425| | | |430| | | | | |

| | | | | | | | | | | | | | | | |
|---|---|---|---|---|---|---|---|---|---|---|---|---|---|---|---|
|Asp|Ser|Asp|Gly|Ser|Phe|Phe|Leu|Tyr|Ser|Lys|Leu|Thr|Val|Asp|Lys|
| |435| | | |440| | | |445| | | | | | |

| | | | | | | | | | | | | | | | |
|---|---|---|---|---|---|---|---|---|---|---|---|---|---|---|---|
|Ser|Arg|Trp|Gln|Gln|Gly|Asn|Val|Phe|Ser|Cys|Ser|Val|Met|His|Glu|
|450| | | |455| | | |460| | | | | | | |

| | | | | | | | | | | | | | | | |
|---|---|---|---|---|---|---|---|---|---|---|---|---|---|---|---|
|Ala|Leu|His|Asn|His|Tyr|Thr|Gln|Lys|Ser|Leu|Ser|Leu|Ser|Pro|Gly|
|465| | | |470| | | |475| | | |480| | | |

Lys

```
<210> SEQ ID NO 129
<211> LENGTH: 738
<212> TYPE: DNA
<213> ORGANISM: Artificial Sequence
<220> FEATURE:
<223> OTHER INFORMATION: IgG antibody light chain variable region

<400> SEQUENCE: 129
atgggatgga gctatatcat cctcttttg gtagcaacag ctacagatgt ccactccagc      60
ggtgtgggtt ccaattttat gctgactcag ccccccctcag tgtcagtgtc cccaggaaag    120
acggccagga tcacttgtag gggagataac cttggagatg taaatgttca ctggtaccag    180
cagcggccag gccaggcccc tgtattggtc atgtattatg atgccgaccg gccctcaggg    240
atccctgagc gattctctgg ctccaactct gggaacacgg ccacactgac catcagcgga    300
gtcgaagccg gggatgaggc cgactactat tgtcaggtgt gggataggac tagtgagtat    360
gtcttcggaa ctgggaccaa ggtcaccgtc ctaggtggag gagccagcct cgtggaaaga    420
tctgtggctg caccatctgt cttcatcttc ccgccatctg atgagcagtt gaaatctgga    480
actgcctctg ttgtgtgcct gctgaataac ttctatccca gagaggccaa agtacagtgg    540
aaggtggata acgccctcca atcgggtaac tcccaggaga gtgtcacaga gcaggacagc    600
aaggacagca cctacagcct cagcagcacc ctgacgctga gcaaagcaga ctacgagaaa    660
cacaaagtct acgcctgcga agtcacccat caggggctga gctcgcccgt cacaaagagc    720
ttcaacaggg gagagtgt                                                   738

<210> SEQ ID NO 130
<211> LENGTH: 246
<212> TYPE: PRT
<213> ORGANISM: Artificial Sequence
<220> FEATURE:
<223> OTHER INFORMATION: IgG antibody light chain variable region

<400> SEQUENCE: 130
```

| | | | | | | | | | | | | | | | |
|---|---|---|---|---|---|---|---|---|---|---|---|---|---|---|---|
|Met|Gly|Trp|Ser|Tyr|Ile|Ile|Leu|Phe|Leu|Val|Ala|Thr|Ala|Thr|Asp|

```
              1               5              10              15
            Val His Ser Ser Gly Val Gly Ser Asn Phe Met Leu Thr Gln Pro Pro
                           20                  25                  30
            Ser Val Ser Val Ser Pro Gly Lys Thr Ala Arg Ile Thr Cys Arg Gly
                           35                  40                  45
            Asp Asn Leu Gly Asp Val Asn Val His Trp Tyr Gln Gln Arg Pro Gly
                           50                  55                  60
            Gln Ala Pro Val Leu Val Met Tyr Tyr Asp Ala Asp Arg Pro Ser Gly
             65                  70                  75                  80
            Ile Pro Glu Arg Phe Ser Gly Ser Asn Ser Gly Asn Thr Ala Thr Leu
                               85                  90                  95
            Thr Ile Ser Gly Val Glu Ala Gly Asp Glu Ala Asp Tyr Tyr Cys Gln
                          100                 105                 110
            Val Trp Asp Arg Thr Ser Glu Tyr Val Phe Gly Thr Gly Thr Lys Val
                          115                 120                 125
            Thr Val Leu Gly Gly Gly Ala Ser Leu Val Glu Arg Ser Val Ala Ala
                          130                 135                 140
            Pro Ser Val Phe Ile Phe Pro Pro Ser Asp Glu Gln Leu Lys Ser Gly
            145                 150                 155                 160
            Thr Ala Ser Val Val Cys Leu Leu Asn Asn Phe Tyr Pro Arg Glu Ala
                              165                 170                 175
            Lys Val Gln Trp Lys Val Asp Asn Ala Leu Gln Ser Gly Asn Ser Gln
                              180                 185                 190
            Glu Ser Val Thr Glu Gln Asp Ser Lys Asp Ser Thr Tyr Ser Leu Ser
                          195                 200                 205
            Ser Thr Leu Thr Leu Ser Lys Ala Asp Tyr Glu Lys His Lys Val Tyr
                          210                 215                 220
            Ala Cys Glu Val Thr His Gln Gly Leu Ser Ser Pro Val Thr Lys Ser
            225                 230                 235                 240
            Phe Asn Arg Gly Glu Cys
                              245

<210> SEQ ID NO 131
<211> LENGTH: 318
<212> TYPE: DNA
<213> ORGANISM: Artificial Sequence
<220> FEATURE:
<223> OTHER INFORMATION: primer

<400> SEQUENCE: 131
gacattgttc tcatccagtc tccagcaatc atgtctgcat ctccagggga gaaggtcacc      60
ataacctgca gtgccagctc aagtgtaagt tacatgcact ggttccagca gaagccaggc     120
acttctccca aactctggat ttatagcaca tccaacctgg cttctggagt ccctgctcgc     180
ttcagtggca gtggatctgg gacctcttac tctctcacaa tcagccgaat ggaggctgaa     240
gatgctgcca cttattactg ccagcaaagg agtagttacc cattcacgtt cggctcgggg     300
acaaagttgg aaataaaa                                                   318

<210> SEQ ID NO 132
<211> LENGTH: 345
<212> TYPE: DNA
<213> ORGANISM: Artificial Sequence
<220> FEATURE:
<223> OTHER INFORMATION: primer

<400> SEQUENCE: 132
```

```
caggttcagc tccagcagtc tggggcagag cttgtgaggt caggggcctc agtcaagttg      60
tcctgcacag cttctggctt caacattaaa gactactata tgcactgggt gaagcagagg     120
cctgaacagg gcctggagtg gattggatgg attgatcctg cgaatggtaa tactaaatat     180
gacccgaagt tccagggcaa ggccactata acagcagaca catcctccaa cacagcctac     240
ctgcagctca gcagcctgac atctgaggac actgccgtct attactgtgc tagatgggac     300
tggtacttcg atgtctgggg cgcagggacc acggtcaccg tttcc                     345
```

```
<210> SEQ ID NO 133
<211> LENGTH: 51
<212> TYPE: DNA
<213> ORGANISM: Artificial Sequence
<220> FEATURE:
<223> OTHER INFORMATION: primer

<400> SEQUENCE: 133
ctgcagaacc agcggtgtgg gttccgacat cgagctcact cagtctccat g              51
```

```
<210> SEQ ID NO 134
<211> LENGTH: 53
<212> TYPE: DNA
<213> ORGANISM: Artificial Sequence
<220> FEATURE:
<223> OTHER INFORMATION: primer

<400> SEQUENCE: 134
ctgcagaacc acgaggctgg ctcctccacg ttttatttcc agcttggtcc ccg             53
```

```
<210> SEQ ID NO 135
<211> LENGTH: 68
<212> TYPE: DNA
<213> ORGANISM: Artificial Sequence
<220> FEATURE:
<223> OTHER INFORMATION: primer

<400> SEQUENCE: 135
cggcccagcc ggccatggcc caggtcaagc tgcagcagtc tggggcagag cttgtggggt      60
caggggcc                                                              68
```

```
<210> SEQ ID NO 136
<211> LENGTH: 29
<212> TYPE: DNA
<213> ORGANISM: Artificial Sequence
<220> FEATURE:
<223> OTHER INFORMATION: primer

<400> SEQUENCE: 136
ggcttcaaca ttaaagactt ctatatgca                                       29
```

```
<210> SEQ ID NO 137
<211> LENGTH: 55
<212> TYPE: DNA
<213> ORGANISM: Artificial Sequence
<220> FEATURE:
<223> OTHER INFORMATION: primer

<400> SEQUENCE: 137
gattatgccc cgaagttcca gggcaaggcc accatgactg cagactcatc ctcca          55
```

```
<210> SEQ ID NO 138
<211> LENGTH: 45
<212> TYPE: DNA
<213> ORGANISM: Artificial Sequence
```

-continued

```
<220> FEATURE:
<223> OTHER INFORMATION: primer

<400> SEQUENCE: 138
tactgtaatg catactatgg tgactacgaa ggctactggg gccaa            45

<210> SEQ ID NO 139
<211> LENGTH: 31
<212> TYPE: DNA
<213> ORGANISM: Artificial Sequence
<220> FEATURE:
<223> OTHER INFORMATION: primer

<400> SEQUENCE: 139
gtctttaatg ttgaagccag aagttgtgca g                           31

<210> SEQ ID NO 140
<211> LENGTH: 50
<212> TYPE: DNA
<213> ORGANISM: Artificial Sequence
<220> FEATURE:
<223> OTHER INFORMATION: primer

<400> SEQUENCE: 140
acttcggggc ataatcagaa tcaccattct caggatcaat ccatccaatc       50

<210> SEQ ID NO 141
<211> LENGTH: 19
<212> TYPE: DNA
<213> ORGANISM: Artificial Sequence
<220> FEATURE:
<223> OTHER INFORMATION: primer

<400> SEQUENCE: 141
gtatgcatta cagtaatag                                         19

<210> SEQ ID NO 142
<211> LENGTH: 62
<212> TYPE: DNA
<213> ORGANISM: Artificial Sequence
<220> FEATURE:
<223> OTHER INFORMATION: primer

<400> SEQUENCE: 142
ccgaggcccc cgaggcctga ggagacggtg accgtggtcc cttggcccca gtagccttcg    60
ta                                                                   62

<210> SEQ ID NO 143
<211> LENGTH: 864
<212> TYPE: DNA
<213> ORGANISM: Artificial Sequence
<220> FEATURE:
<223> OTHER INFORMATION: phage vector DNA r1C11-ScFv region

<400> SEQUENCE: 143
atgaaatacc tattgcctac ggcagccgct ggattgttat tactcgcggc ccagccggcc    60
atggcccagg tcaagctgca gcagtctggg gcagagcttg tggggtcagg ggcctcagtc   120
aaattgtcct gcacaacttc tggcttcaac attaaagact ctatatgca ctgggtgaag    180 cagaggcctg aacagggcct ggagtggatt ggatggattg atcctgagaa tggtgattct   240
gattatgccc gaagttcca gggcaaggcc accatgactg cagactcatc ctccaacaca    300
gcctacctgc agctcagcag cctgacatct gaggacactg ccgtctatta ctgtaatgca   360
```

```
tactatggtg actacgaagg ctactggggc caagggacca cggtcaccgt ctcctcaggc    420
ctcgggggcc tcggaggagg aggtagtggc ggaggaggct ccgtggatc cagcggtgtg     480 ggttccgaca tcgagctcac tcagtctcca gcaatcatgt ctgcatctcc aggggagaag    540
gtcaccataa cctgcagtgc cagctcaagt gtaagttaca tgcactggtt ccagcagaag    600
ccaggcactt ctcccaaact ctggatttat agcacatcca acctggatta tggagtccct    660
gctcgcttca gtggcagtgg atctgggacc tcttactctc tcacaatcag ccgaatggag    720
gctgaagatg ctgccactta ttactgccag caaaggagta gttacccatt cacgttcggc    780
tcggggacca agctggaaat aaaacgtgga ggagccagcc tcgtggaatt cgagcagaag    840
ctgatctctg aggaagacct gtag                                          864
```

<210> SEQ ID NO 144
<211> LENGTH: 348
<212> TYPE: DNA
<213> ORGANISM: Artificial Sequence
<220> FEATURE:
<223> OTHER INFORMATION: primer template for heavy chain region

<400> SEQUENCE: 144

```
gaggtgcagc tggtggagtc tgggggaggc ctggtcaagc ctgggggtc cctgagactc      60 tcctgtgcag cctctggatt caccttcagt agctatagca tgaactgggt ccgccaggct    120
ccagggaagg ggctggagtg gtctcatcc attagtagta gtagtagtta catacactac    180
gcagactcag tgaagggccg attcaccatc tccagagaca acgccaagaa ctcactgtat    240
ctgcaaatga acagtctgag agccgaggac acggccgtgt attactgtgc gagagtcaca    300
gatgcttttg atatctgggg ccccggaacc ctggtcaccg tctcctca               348
```

<210> SEQ ID NO 145
<211> LENGTH: 328
<212> TYPE: DNA
<213> ORGANISM: Artificial Sequence
<220> FEATURE:
<223> OTHER INFORMATION: primer template for light chain region

<400> SEQUENCE: 145

```
gacatccaga tgacccagtc tccatcttcc gtgtctgcat ctgtaggaga cagagtcacc      60
atcacttgtc gggcgagtca gggtattagc agctatttag gctggtatca gcagaaacca    120
gggaaagccc ctaagctcct gatctatgct gcatccaatt tgcaaacagg gtcccgcca    180 aggttcagcg gcagtggatc cgggacaagt ttcactctca ccctcaataa tgtgcagcct    240
gaagattctg caacttacta ttgtcaacag gctgacagtt ccctctttc ggcggaggga    300 ccaaagtgga aatcaaacgt gaggagcc                                      328
```

<210> SEQ ID NO 146
<211> LENGTH: 23
<212> TYPE: DNA
<213> ORGANISM: Artificial Sequence
<220> FEATURE:
<223> OTHER INFORMATION: primer

<400> SEQUENCE: 146

```
ccccagcggt gtgggttccg aca                                           23
```

<210> SEQ ID NO 147
<211> LENGTH: 38
<212> TYPE: DNA
<213> ORGANISM: Artificial Sequence

```
<220> FEATURE:
<223> OTHER INFORMATION: primer

<400> SEQUENCE: 147
tggtgactct gtctcctata gatgcagaca cggatgat                              38

<210> SEQ ID NO 148
<211> LENGTH: 22
<212> TYPE: DNA
<213> ORGANISM: Artificial Sequence
<220> FEATURE:
<223> OTHER INFORMATION: primer

<400> SEQUENCE: 148
tctataggag acagagtcac ca                                              22

<210> SEQ ID NO 149
<211> LENGTH: 38
<212> TYPE: DNA
<213> ORGANISM: Artificial Sequence
<220> FEATURE:
<223> OTHER INFORMATION: primer

<400> SEQUENCE: 149
taccagccta accagttgtc aatacccctga ctcgcccg                             38

<210> SEQ ID NO 150
<211> LENGTH: 41
<212> TYPE: DNA
<213> ORGANISM: Artificial Sequence
<220> FEATURE:
<223> OTHER INFORMATION: primer

<400> SEQUENCE: 150
ttgacaactg gttaggctgg tatcagcaga aaccagggaa a                          41

<210> SEQ ID NO 151
<211> LENGTH: 52
<212> TYPE: DNA
<213> ORGANISM: Artificial Sequence
<220> FEATURE:
<223> OTHER INFORMATION: primer

<400> SEQUENCE: 151
accttgatgg gaccctgtg tccaaattgg atgcatcata gatcaggagc tt               52

<210> SEQ ID NO 152
<211> LENGTH: 22
<212> TYPE: DNA
<213> ORGANISM: Artificial Sequence
<220> FEATURE:
<223> OTHER INFORMATION: primer

<400> SEQUENCE: 152
ccccacgagg ctggctcctc ca                                              22

<210> SEQ ID NO 153
<211> LENGTH: 58
<212> TYPE: DNA
<213> ORGANISM: Artificial Sequence
<220> FEATURE:
<223> OTHER INFORMATION: primer

<400> SEQUENCE: 153
ccggcccagc cggccatggc cgaggtgcag ctggtgcagt ctgggggagg cctggtca        58
```

<210> SEQ ID NO 154
<211> LENGTH: 39
<212> TYPE: DNA
<213> ORGANISM: Artificial Sequence
<220> FEATURE:
<223> OTHER INFORMATION: primer

<400> SEQUENCE: 154
gtagtagtag tagttacata tactacgcag actcagtga                     39

<210> SEQ ID NO 155
<211> LENGTH: 50
<212> TYPE: DNA
<213> ORGANISM: Artificial Sequence
<220> FEATURE:
<223> OTHER INFORMATION: primer

<400> SEQUENCE: 155
ttactgtgcg agagtcacag atgcttttga tatctggggc caagggacaa         50

<210> SEQ ID NO 156
<211> LENGTH: 37
<212> TYPE: DNA
<213> ORGANISM: Artificial Sequence
<220> FEATURE:
<223> OTHER INFORMATION: primer

<400> SEQUENCE: 156
tcactgagtc tgcgtagtat atgtaactac tactact                       37

<210> SEQ ID NO 157
<211> LENGTH: 24
<212> TYPE: DNA
<213> ORGANISM: Artificial Sequence
<220> FEATURE:
<223> OTHER INFORMATION: primer

<400> SEQUENCE: 157
ctgtgactct cgcacagtaa taca                                     24

<210> SEQ ID NO 158
<211> LENGTH: 49
<212> TYPE: DNA
<213> ORGANISM: Artificial Sequence
<220> FEATURE:
<223> OTHER INFORMATION: primer

<400> SEQUENCE: 158
ccggcccccg aggcctgagg agacggtgac cattgtccct tggccccag          49

<210> SEQ ID NO 159
<211> LENGTH: 864
<212> TYPE: DNA
<213> ORGANISM: Artificial Sequence
<220> FEATURE:
<223> OTHER INFORMATION: phage vector insert r1121-ScFv DNA region

<400> SEQUENCE: 159
atgaaatacc tattgcctac ggcagccgct ggattgttat tactcgcggc ccagccggcc   60
atggccgagg tgcagctggt gcagtctggg ggaggcctgg tcaagcctgg ggggtccctg  120
agactctcct gtgcagcctc tggattcacc ttcagtagct atagcatgaa ctgggtccgc  180
caggctccag ggaaggggct ggagtgggtc tcatccatta gtagtagtag tagttacata  240
tactacgcag actcagtgaa gggccgattc accatctcca gagacaacgc caagaactca  300

```
ctgtatctgc aaatgaacag tctgagagcc gaggacacgg ccgtgtatta ctgtgcgaga      360
gtcacagatg cttttgatat ctggggccaa gggacaatgg tcaccgtctc ctcaggcctc      420
gggggcctcg gaggaggagg tagtggcgga ggaggctccg gtggatccag cggtgtgggt      480
tccgacatcc agatgaccca gtctccatct tccgtgtctg catctatagg agacagagtc      540
accatcactt gtcgggcgag tcagggtatt gacaactggt taggctggta tcagcagaaa      600
cctgggaaag cccctaaact cctgatctac gatgcatcca atttggacac aggggtccca      660
tcaaggttca gtggaagtgg atctgggaca tattttactc tcaccatcag tagcctgcaa      720
gctgaagatt ttgcagttta tttctgtcaa caggctaaag cttttcctcc cactttcggc      780
ggagggacca aggtggacat caaacgtgga ggagccagcc tcgtggaatt cgagcagaag      840
ctgatctctg aggaagacct gtga                                            864

<210> SEQ ID NO 160
<211> LENGTH: 29
<212> TYPE: DNA
<213> ORGANISM: Artificial Sequence
<220> FEATURE:
<223> OTHER INFORMATION: primer

<400> SEQUENCE: 160
gagccagcct cgtggaattc gaacaaaaa                                        29

<210> SEQ ID NO 161
<211> LENGTH: 55
<212> TYPE: DNA
<213> ORGANISM: Artificial Sequence
<220> FEATURE:
<223> OTHER INFORMATION: primer

<400> SEQUENCE: 161
tgctcgagat tcagatcctc ttctgagatg agttttttgtt gaattccacg aggct           55

<210> SEQ ID NO 162
<211> LENGTH: 21
<212> TYPE: DNA
<213> ORGANISM: Artificial Sequence
<220> FEATURE:
<223> OTHER INFORMATION: primer

<400> SEQUENCE: 162
ccagcctcgt ggaattcgaa c                                                21

<210> SEQ ID NO 163
<211> LENGTH: 69
<212> TYPE: DNA
<213> ORGANISM: Artificial Sequence
<220> FEATURE:
<223> OTHER INFORMATION: primer

<400> SEQUENCE: 163
ccgctcgagg gtggagtcca gacctaatag agggtttggg atcggctttc cattcagatc      60
ctcttctga                                                              69

<210> SEQ ID NO 164
<211> LENGTH: 324
<212> TYPE: DNA
<213> ORGANISM: Artificial Sequence
<220> FEATURE:
<223> OTHER INFORMATION: antibody light chain sequence TTAC-0002 (KE3)
```

<400> SEQUENCE: 164

```
aattttatgc tgactcagcc ccctcagtg tcagtggccc ccggaaagac ggccaggatc    60
acctgtgggg agacaacat tggaagtcaa agtgtgcact ggtaccagca gcggccaggc   120
caggcccctg tattggtcat gtattatgat gccgaccggc cctcagggat ccctgagcga   180
ttctctggct ccaactctgg gaacacggcc acactgacca tcagcggagt cgaagccggg   240
gatgaggccg actactattg tcaggtgtgg gataggacta gtgagtatgt cttcggaact   300
gggaccaagg tcaccgtcct aggt                                         324
```

<210> SEQ ID NO 165
<211> LENGTH: 324
<212> TYPE: DNA
<213> ORGANISM: Artificial Sequence
<220> FEATURE:
<223> OTHER INFORMATION: antibody light chain sequence TTAC-0003 (KE6)

<400> SEQUENCE: 165

```
aattttatgc tgactcagcc ccctcagtg tcagtggccc caggaaagac ggccgggatt    60
acctgtgggg agacgacat tggaagtaaa agtgtgcact ggtaccagca gaagccaggc   120
caggcccctg tgttggtcat ctattatgat agcgaccggc cctcagggat ccctgagcga   180
ttctctggct ccaactctgg gaacacggcc acactgacca tcagcggagt cgaagccggg   240
gatgaggccg actactattg tcaggtgtgg gataggacta gtgagtatgt cttcggaact   300
gggaccaagg tcaccgtcct aggt                                         324
```

<210> SEQ ID NO 166
<211> LENGTH: 321
<212> TYPE: DNA
<213> ORGANISM: Artificial Sequence
<220> FEATURE:
<223> OTHER INFORMATION: antibody light chain sequence TTAC-0004 (IE4)

<400> SEQUENCE: 166

```
tcctatgagc tgactcagcc accctcagtg tcatcggccc caggaaagac ggccaccatt    60
acctgtgagg gaaagaacat tggcagtaaa agtgtgcact ggtaccagca gaagccaggc   120
caggcccctg tgctgctcat ttattatgat caagaccggc cctcagcgat ccctgagcga   180
ttctctggct ccaactctga caacatggcc accctgacca tcagccgggt cgcagccggg   240
gatgaggctg actattactg tcaggtgtgg ggcaacggca aagtggtgtt cggcggaggg   300
accaagctga ccgtcctagg t                                            321
```

<210> SEQ ID NO 167
<211> LENGTH: 324
<212> TYPE: DNA
<213> ORGANISM: Artificial Sequence
<220> FEATURE:
<223> OTHER INFORMATION: antibody light chain sequence TTAC-0005 (SD5)

<400> SEQUENCE: 167

```
aattttatgc tgactcagcc ccctcccgtg tcagtggccc caggaaagac ggccaggatc    60
acttgtaggg gagataacct tggagatgta aatgttcact ggtaccagca gcggccaggc   120
caggcccctg tattggtcat gtattatgat gccgaccggc cctcggggat ccctgagcga   180
ttctctggct ccaactctgg gaacacggcc acactgacca tcagcggagt cgaagccggg   240
gatgaggccg actactattg tcaggtgtgg gataggacta gtgagtatgt cttcggagct   300
gggaccaagg tcaccgtcct aggt                                         324
```

<210> SEQ ID NO 168
<211> LENGTH: 324
<212> TYPE: DNA
<213> ORGANISM: Artificial Sequence
<220> FEATURE:
<223> OTHER INFORMATION: antibody light chain sequence TTAC-0006 (2KG8)

<400> SEQUENCE: 168

```
aattttatgc tgactcagcc ccctccgtg tcagtggccc caggaaagac ggccaggatc      60
acttgtaggg gagataacct tggagatgta aatgttcact ggtaccagca gcggccaggc    120
caggcccctg tattggtcat gtattatgat gccgaccggc cctcgggat ccctgagcga     180
ttctctggct ccaactctgg gaacacggcc acactgacca tcagcggagt cgaagccggg    240
gatgaggccg actactattg tcaggtgtgg gataggacta gtgagtatgt cttcggagct    300
gggaccaagg tcaccgtcct aggt                                           324
```

<210> SEQ ID NO 169
<211> LENGTH: 324
<212> TYPE: DNA
<213> ORGANISM: Artificial Sequence
<220> FEATURE:
<223> OTHER INFORMATION: antibody light chain sequence TAC-0007 (3KE11)

<400> SEQUENCE: 169

```
aattttatgc tgactcagcc ccctcagtg tcagtgtccc caggaaagac ggccaggatc      60
acttgtaggg gagataacct tggagatgta aatgttcact ggtaccagca gcggccaggc    120
caggcccctg tattggtcat gtattatgat gccgaccggc cctcagggat ccctgagcga    180
ttctctggct ccaactctgg gaacacggcc atactgacca tcagcggagt cgaagccggg    240
gatgaggccg actactattg tcaggtgtgg gataggacta gtgagtatgt cttcggaact    300
gggaccaagg tcaccgtcct aggt                                           324
```

<210> SEQ ID NO 170
<211> LENGTH: 324
<212> TYPE: DNA
<213> ORGANISM: Artificial Sequence
<220> FEATURE:
<223> OTHER INFORMATION: antibody light chain sequence TTAC-0008 (3KF11)

<400> SEQUENCE: 170

```
aattttatgc tgactcagcc ctcttcagtg tcagtgtccc caggaaagac ggccaggatc     60
acttgtaggg gagataacct tggagatgta aatgttcact ggtaccagca gcggccaggc   120
caggcccctg tattggtcat gtattatgat gccgaccggc cctcagggat ccctgagcga   180
ttctctggct ccaactctgg gaacacggcc acactgacca tcagcggagt cgaagcaggg   240
gatgaggccg actactattg tcaggtgtgg gataggacta gtgagtatgt cttcggaact   300
gggaccaagg tcaccgtcct aggt                                          324
```

<210> SEQ ID NO 171
<211> LENGTH: 324
<212> TYPE: DNA
<213> ORGANISM: Artificial Sequence
<220> FEATURE:
<223> OTHER INFORMATION: antibody light chain sequence TTAC-0009(3KG3)

<400> SEQUENCE: 171

```
aattttatgc tgactcagcc ccactctgtg tcagtgtccc caggaaagac ggccaggatc     60
```

```
acttgtaggg gagataacct tggagatgta aatgttcact ggtaccagca gcggccaggc    120
caggcccctg tattggtcat gtattatgat gccgaccggc cctcagggat ccctgagcga    180
ttctctggct ccaactctgg gaacacggcc acactgacca tcagcggagt cgaagccggg    240
gatgaggccg actactattg tcaggtgtgg gataggacta gtgagtatgt cttcggaact    300
gggaccaagg tcaccgtcct aggt                                           324

<210> SEQ ID NO 172
<211> LENGTH: 324
<212> TYPE: DNA
<213> ORGANISM: Artificial Sequence
<220> FEATURE:
<223> OTHER INFORMATION: antibody light chain sequence TTAC-0010(3IG11)

<400> SEQUENCE: 172
aattttatgc tgactcagcc cccctcagtg tcagtgtccc caggaaagac ggccaggatc    60
acttgtaggg gagataacct tggagatgta aatgttcact ggtaccagca gcggccaggc    120
caggcccctg tattgatcat gtattatgat gccgaccggc cctcagggat ccctgagcga    180
ttctctggct ccaactctgg gaacacggcc acactgacca tcagcggagt cgaagccggg    240
gatgaggccg actactattg tcaggtgtgg gataggacta gtgagtatgt cttcggaact    300
gggaccaagg tcaccgtcct aggt                                           324

<210> SEQ ID NO 173
<211> LENGTH: 324
<212> TYPE: DNA
<213> ORGANISM: Artificial Sequence
<220> FEATURE:
<223> OTHER INFORMATION: antibody light chain sequence TTAC-0011(3IG12)

<400> SEQUENCE: 173
aattttatgc tgactcagcc ccactctgtg tcagtgtccc caggaaagac ggccaggatc    60
acttgtaggg gagataacct tggagatgta aatgttcact ggtaccagca gcggccaggc    120
caggcccctg tattggtcat gtattatgat gccgaccggc cctcagggat ccctgagcga    180
ttctctggct ccaactctgg gaacacggcc acactgacca tcagcggagt cgaagccggg    240
gatgaggccg actactattg tcaggtgtgg gataggacta gtgagtatgt cttcggaact    300
gggaccaagg tcaccgtcct aggt                                           324

<210> SEQ ID NO 174
<211> LENGTH: 324
<212> TYPE: DNA
<213> ORGANISM: Artificial Sequence
<220> FEATURE:
<223> OTHER INFORMATION: antibody light chain sequence TTAC-0012 (3IE1)

<400> SEQUENCE: 174
aattttatgc tgactcagcc ctcttcagtg tcagtgcccc caggaaagac ggccaggatc    60
acttgtaggg gagataacct tggagatgta aatgttcact ggtaccagca gcggcgaggc    120
caggcccctg tattggtcat gtattatgat gccgaccggc cctcagggat ccctgagcga    180
ttctctggct ccaactctgg gaacacggcc acactgacca tcagcggagt cgaagccggg    240
gatgaggccg actactattg tcaggtgtgg gataggacta gtgagtttgt cttcggaact    300
gggaccaagg tcaccgtcct aggt                                           324

<210> SEQ ID NO 175
<211> LENGTH: 324
```

```
<212> TYPE: DNA
<213> ORGANISM: Artificial Sequence
<220> FEATURE:
<223> OTHER INFORMATION: antibody light chain sequence TTAC-0013 (3IH2)

<400> SEQUENCE: 175
aattttatgc tgactcagcc cccctcactg tccgtgtccc caggacagac ggccaggatc    60
acttgtaggg gagacaacct tggagatgta aatgttcact ggtaccagca gcggccaggc   120
caggcccctg tattggtcat gtattatgat gccgaccggc cctcaggat ccctgagcga    180 ttctctggct ccaactctgg gaacacggcc acactgacca tcagcggagt cgaagccggg   240
gatgaggccg actactattg tcaggtgtgg gataggacta gtgagtatgt cttcggaact   300
gggaccaagg tcaccgtcct aggt                                         324

<210> SEQ ID NO 176
<211> LENGTH: 324
<212> TYPE: DNA
<213> ORGANISM: Artificial Sequence
<220> FEATURE:
<223> OTHER INFORMATION: antibody light chain sequence TTAC-0014 (K3F1)

<400> SEQUENCE: 176
aattttatgc tgactcagcc cccctctgtg tcagtggccc caggacagac ggccaggatc    60
acttgtaggg gagataacct tggagatgta aatgttcact ggtaccagca gcggccaggc   120
caggcccctg tattggtcat gtattatgat gccgaccggc cctcagggat ccctgagcga   180
ttctctggct ccaactctgg gaacacggcc acactgacca tcagcggagt cgaagccggg   240
gatgaggccg actactattg tcaggtgtgg gataggacta gtgagtatgt cttcggaact   300
gggaccaagg tcaccgtcct aggt                                         324

<210> SEQ ID NO 177
<211> LENGTH: 324
<212> TYPE: DNA
<213> ORGANISM: Artificial Sequence
<220> FEATURE:
<223> OTHER INFORMATION: antibody light chain sequence TTAC-0015 (I2F2)

<400> SEQUENCE: 177
aattttatgc tgactcagcc ccccgcagtg tcagtgtccc caggaaagac ggccaggatc    60
acttgtaggg gagataacct tggagatgta aatgttcact ggtaccagca gcggccaggc   120
caggcccctg tattggtcat gtattatgat gccgaccggc cctcagggat ccctgagcga   180
ttctctggct ccaactctgg gaacacggcc acactgacca tcagcggagt cgaagccggg   240
gatgaggccg actactattg tcaggtgtgg gataggacta gtgagtatgt cttcggaact   300
gggaccaagg tcaccgtcct aggt                                         324

<210> SEQ ID NO 178
<211> LENGTH: 324
<212> TYPE: DNA
<213> ORGANISM: Artificial Sequence
<220> FEATURE:
<223> OTHER INFORMATION: antibody light chain sequence TTAC-0016 (I3A12)

<400> SEQUENCE: 178
aattttatgc tgactcagcc ccctcagtg tcagtgtccc caggaaagac ggccaggatc     60
acttgtaggg gagataacct tggagatgta aatgttcact ggtaccagca gcggccaggc   120
caggcccctg tattggtcat gtattatgat gccgaccggc cctcagggat ccctaagcga   180
```

```
ttctctggct ccaactctgg gaacacggcc acactgacca tcagcggagt cgaagccggg    240
gatgaggccg actactattg tcaggtgtgg gataggacta gtgagtatgt cttcggaact    300
gggaccaagg tcaccgtcct aggt                                          324

<210> SEQ ID NO 179
<211> LENGTH: 324
<212> TYPE: DNA
<213> ORGANISM: Artificial Sequence
<220> FEATURE:
<223> OTHER INFORMATION: antibody light chain sequence TTAC-0017 (I3F2)

<400> SEQUENCE: 179
aattttatgc tgactcagcc cccctcagtg tcagtgtccc caggaaagac ggccaggatc    60
acttgtaggg gagataacct tggagatgta aatgttcact ggtaccagca gcggccaggc   120
caggcccctg tattggtcat ttattatgat gccgacaggc cctcagggat ccctgagcga   180
ttctctggct ccaactctgg gaacacggcc acactgacca tcagcggagt cgaagccggg   240
gatgaggccg actactattg tcaggtgtgg gataggacta gtgagtatgt cttcggaact   300
gggaccaagg tcaccgtcct aggt                                          324

<210> SEQ ID NO 180
<211> LENGTH: 324
<212> TYPE: DNA
<213> ORGANISM: Artificial Sequence
<220> FEATURE:
<223> OTHER INFORMATION: antibody light chain sequence TTAC-0018 (4SC3)

<400> SEQUENCE: 180
aattttatgc tgactcagcc cccctcagtg tcagtgtccc caggaaagac ggccaggatc    60
acttgtaggg gagataacct tggagatgta aatgttcact ggtaccagca gcggccaggc   120
caggcccctg tattagtcat gtattatgat gccgaccggc cctcagggat ccctgagcga   180
ttctctggct ccaactctgg gaacacggcc acactgacca tcagcggagt cgaagccggg   240
gatgaggccg actactattg tcaggtgtgg gataggacta atgagtatgt cttcggaact   300
gggaccaagg tcaccgtcct aggt                                          324

<210> SEQ ID NO 181
<211> LENGTH: 324
<212> TYPE: DNA
<213> ORGANISM: Artificial Sequence
<220> FEATURE:
<223> OTHER INFORMATION: antibody light chain sequence TTAC-0019 (4SC5)

<400> SEQUENCE: 181
cagttcgtgc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
ttctctggct ccaactttgg gaacacggcc accctgacca tcagcagggt cgaagccggg   240
gatgaggccg actattattg tcaggtttgg gatagtagtc gtgattatgt cttcggaact   300
gggaccaagg tcaccgtcct aggt                                          324
```

HUMAN MONOCLONAL ANTIBODY NEUTRALIZING VASCULAR ENDOTHELIAL GROWTH FACTOR RECEPTOR AND USE THEREOF

CROSS-REFERENCE TO RELATED APPLICATIONS

This application is a divisional application of U.S. patent application Ser. No. 12/664,226, filed on Nov. 19, 2010 (currently pending), the disclosure of which is herein incorporated by reference in its entirety. The U.S. patent application Ser. No. 12/664,226 is a national entry of International Application No. PCT/KR2007/003077, filed on Jun. 26, 2007, which claims priority to Korean Application No. 10-2007-0057719 filed on Jun. 13, 2007, the entire contents of which are incorporated herein by reference.

TECHNICAL FIELD

The present invention relates to human monoclonal antibodies neutralizing vascular endothelial growth factor receptor and the use thereof, and more particularly to human ScFv molecules neutralizing vascular endothelial growth factor receptor, and a composition for inhibiting angiogenesis and a composition for treating cancer, which contain the human ScFv molecules.

BACKGROUND ART

Angiogenesis means the formation of new blood vessels from pre-existing vessels by the growth, differentiation and migration of endothelial cells and does not occur in healthy adults, except for some special occasions, including wound healing, menstruation, etc. However, the excessive formation of new blood vessels in diseases, such as tumor growth and metastasis, age-related macular degeneration, rheumatoid arthritis, diabetic retinopathy, psoriasis and chronic inflammation, has been reported (Cameliet and Jain, *Nature,* 407: 249, 2000). For this reason, many efforts to treat diseases, particularly tumors, using angiogenesis inhibitors, have been made.

Factors involved in angiogenesis include vascular endothelial growth factor (VEGF), epithelial growth factor (EGF), platelet-derived growth factor (PDGF), transforming growth factor-b (TGFb), fibroblast growth factor (FGF), etc. Among them, the vascular endothelial growth factor is an endothelial cell-specific factor which is involved directly in the growth, differentiation and migration of endothelial cells, and there are four different isoforms (VEGF165, VEGF121, VEGF189 and VEGF206). Among the four isoforms, VEGF165 is the most abundant isoform in all human tissues except placenta (Tisher et al., *J. Biol. Chem.,* 266:11947, 1991).

Vascular endothelial growth factor (VEGF) regulates new blood vessel formation resulting from the differentiation of endothelial precursors (angioblasts) in situ, is expressed in embryonic tissues (Breier et al., *Development (Camb),* 114: 521, 1992), macrophages, and proliferating epithelial keratinocytes during wound healing (Brown et al., *J. Exp. Med.,* 176:1375, 1992), and may be responsible for tissue edema associated with inflammation (Ferrara et al., *Endocr. Rev.,* 13:18, 1992). In situ hybridization studies have demonstrated high VEGF expression in a number of human tumor lines including glioblastoma multiforme, hemangioblastoma, central nervous system neoplasms and AIDS-associated Kaposi's sarcoma (Plate et al., *Nature,* 359:845, 1992; Plate et al., *Cancer Res.,* 53: 5822, 1993; Berkman et al., *J. Clin. Invest.,* 91:153, 1993; Nakamura et al., *AIDS Weekly,* 13(1), 1992). High levels of VEGF were also observed in hypoxia induced angiogenesis (Shweiki et al., *Nature,* 359:843, 1992).

The biological function of VEGF is mediated through its high affinity VEGF receptors which are selectively expressed in endothelial cells during embryogenesis (Millauer et al., *Cell,* 72:835, 1993) and during tumor formation. VEGF receptors (VEGFR) typically are class III receptor-type tyrosine kinases characterized by having several, typically 5 or 7, immunoglobulin-like loops in their amino-terminal extracellular ligand-binding domain of a receptor (Kaipainen et al., *J. Exp. Med.,* 178:2027, 1993). The other two regions include a transmembrane region and a carboxy-terminal intracellular catalytic domain interrupted by an insertion of hydrophilic interkinase sequences of variable lengths, called the kinase insert domain (Terman et al., *Oncogene,* 6:1677, 1991). VEGF receptors include fms-like tyrosine kinase receptor (Flt-1), or VEGFR-1 (Shibuya et al., *Oncogene,* 5:519, 1990; WO 92/14248; Terman et al., *Oncogene,* 6:1677, 1991), kinase insert domain-containing receptor/fetal liver kinase (KDR/Flk-1), or VEGFR-2 (Matthews et al., *PNAS,* 88:9026, 1991), although other receptors such as neuropilin-1 and neuropilin-2 can also bind VEGF. Another tyrosine kinase receptor, VEGFR-3 (Flt-4), binds the VEGF homologues VEGF-C and VEGF-D and is important in the development of lymphatic vessels.

High levels of Flk-1 are expressed by endothelial cells that infiltrate gliomas (Plate et al., *Nature,* 359:845, 1992). Flk-1 levels are specifically upregulated by VEGF produced by human glioblastomas (Plate et al., *Cancer Res.,* 53:5822, 1993).

The finding of high levels of Flk-1 expression in glioblastoma associated endothelial cells (GAEC) indicates that receptor activity is probably induced during tumor formation since Flk-1 transcripts are barely detectable in normal brain endothelial cells. This upregulation is confined to the vascular endothelial cells in close proximity to the tumor. Blocking VEGF activity with neutralizing anti-VEGF monoclonal antibodies (mAbs) resulted in inhibition of the growth of human tumor xenografts in nude mice (Kim, K. et al., *Nature,* 362:841-844, 1993), indicating a direct role for VEGF in tumor-related angiogenesis.

Although VEGF ligands are upregulated in tumor cells, and the receptors thereof are upregulated in tumor infiltrated vascular endothelial cells, the expression levels of VEGF ligands and the receptors thereof are low in normal cells that are not associated with angiogenesis. Therefore, such normal cells would block the interaction between VEGF and the receptors thereof to inhibit angiogenesis, thus inhibiting tumor growth.

High levels of VEGFR-2 are expressed by endothelial cells that infiltrate gliomas, and are specifically upregulated by VEGF produced by human glioblastomas (Plate et al., *Nature,* 359:845, 1992; Plate et al., *Cancer Res.,* 53:5822, 1993). The finding of high levels of VEGR-2 expression in glioblastoma associated endothelial cells (GAEC) suggests that receptor activity is induced during tumor formation, since VEGFR-2 transcripts are barely detectable in normal brain endothelial cells.

Therefore, studies focused on inhibiting the activity of VEGF, which is expressed in tumor growth sites, to inhibit angiogenesis so as to inhibit tumor growth, are being actively conducted. Typically, methods of inhibiting VEGF receptors on the membrane of cancer cells to prevent VEGF from entering cells have been developed. Examples of cell lines producing VEGFR antibodies include a hybridoma cell line producing rat anti-mouse VEGFR-2 monoclonal antibody (DC101; ATCC HB 11534), a hybridoma cell line (M25, 18A1; ATCC HB 12152) producing mouse anti-mouse VEGFR-2 monoclonal antibody mAb 25, and a hybridoma cell line producing mouse anti-mouse VEGFR-2 monoclonal antibody mAb 73 [(M73,24; ATCC HB 12153), KM1730 (FERM BP-5697; WO 98/22616; WO 99/59636), KM1731 (FERM BP-5718), KM1732 (FERM BP-5698), KM1748 (FERM BP-5699), KM1750 (FERM BP-5700)].

There has been a continuous development of humanized antibodies against VEGF receptors. These humanized antibodies against VEGF receptors, developed to date, showed high competition with VEGF in vitro, but had problems in that their ability to neutralize VEGF receptors in cells is reduced and in that the antibodies do not show cross-reactivity in mice or rats, such that animal tests cannot be carried out.

Accordingly, the present inventors have constructed a library of non-immunized fully human antibodies, screened single chain variable fragment (ScFv) antibodies against VEGF receptor (KDR), and found that the antibodies exhibit an excellent KDR-neutralizing effect not only in vitro, but also in cells and in vivo, and show cross-reactivity even in mice and rats, thereby completing the present invention.

SUMMARY OF THE INVENTION

It is an object of the present invention to provide a fully human single chain variable fragment (ScFv) antibodies 6A6-ScFv and 6A6-IgG, which have an excellent ability to neutralize VEGF receptor in cells and in vivo.

Another object of the present invention is to provide a fully human single chain variable fragment (ScFv), which is a light chain variant of 6A6, which shows a more excellent ability to neutralize VEGF receptor compared to that of 6A6-ScFv.

Still another object of the present invention is to provide a composition for inhibiting angiogenesis, which contains a fully human ScFv or IgG having the ability to neutralize VEGF receptor.

Yet another object of the present invention is to provide a composition for treating cancer, which contains a fully human ScFv or IgG having the ability to neutralize VEGF receptor.

To achieve the above objects, in one aspect, the present invention provides a single chain variable fragment (ScFv) molecule, which contains a light chain variable region represented by an amino acid sequence of any one of SEQ ID NOS: 1 to 19 and functions to neutralize vascular endothelial growth factor receptor. In the present invention, the ScFv (single chain variable fragment) molecule and a construct thereof preferably have a heavy chain variable region represented by an amino acid sequence of SEQ ID NO: 20.

In another aspect, the present invention provides a DNA encoding said ScFv (single chain variable fragment) molecule, a vector containing said DNA, and recombinant cells transformed with said vector. In the present invention, the cells are preferably bacterial or animal cells.

In still another aspect, the present invention provides a composition for inhibiting angiogenesis, which contains said ScFv molecule, and a composition for treating cancer, which contains said ScFv molecule.

In still another aspect, the present invention provides an IgG, which contains a light chain variable region represented by an amino acid sequence of any one of SEQ ID NOS: 1 to 19 and functions to neutralize vascular endothelial growth factor receptor. In the present invention, said IgG preferably has a heavy chain variable region represented by an amino acid sequence of SEQ ID NO: 20.

In yet another aspect, the present invention provides a composition for inhibiting angiogenesis, which contains said IgG, and a composition for treating cancer, which contains said IgG.

Other features and aspects of the present invention will be apparent from the following detailed description and the appended claims.

BRIEF DESCRIPTION OF DRAWINGS

FIG. 1 shows the amino acid sequence and function of a gene inserted into a pCDNA3-KDR D123tFcm vector.

FIG. 2 shows a schematic diagram of KDR(ECD1-2) and KDR(ECD2-3)-Fc for epitope mapping according to the present invention.

FIG. 5 shows the nucleic acid sequence, amino acid sequence and CDR sequence of 6A6 ScFv phage according to the present invention.

FIG. 21 shows the results of Western blot analysis for the ability of the inventive anti-KDR antibody to inhibit KDR phosphorylation and ERK phosphorylation, which is induced by VEGF.

FIG. 23 shows that an IgG-type KDR antibody inhibits endothelial cell tube formation induced by VEGF.

FIG. 25 shows the inhibitory effect of the IgG-type KDR antibody on rat aortic ring sprouting induced by VEGF.

FIG. 26 shows analysis results for the inhibitory effect of the IgG-type KDR antibody on angiogenesis induced by VEGF.

FIG. 31 shows color images of the IgG-type 6A6 antibody labeled with iodine-123 in a mouse tumor model of chronic myelogenous leukemia.

FIG. 35 shows the results of VEGF competition assays of anti-KDR antibodies obtained through light chain shuffling.

DETAILED DESCRIPTION OF THE INVENTION, AND PREFERRED EMBODIMENTS

Figure 3:
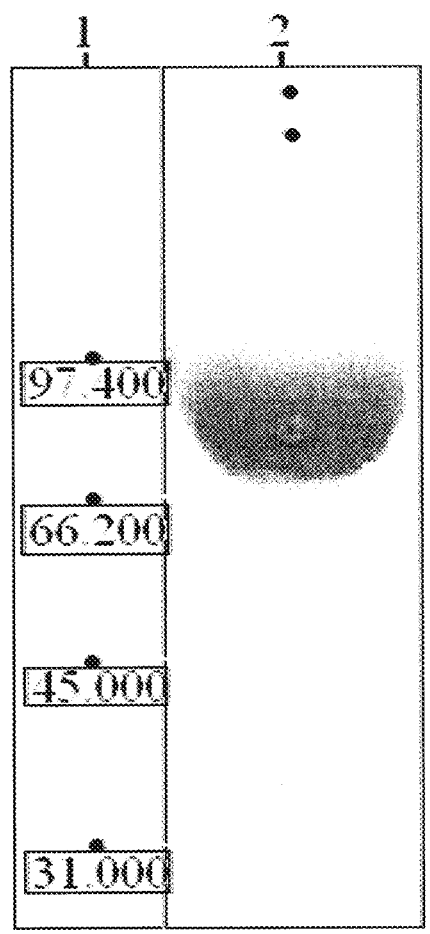
FIG. 3 shows the results of SDS-PAGE of KDR(ECD1-3)-Fc purified in the present invention.

In one aspect, the present invention relates to a fully human ScFv (single chain variable fragment) antibody 6A6 (TTAC-0001)-ScFv, which neutralizes vascular endothelial growth factor.

The 6A6-ScFv was screened in the following manner. First, a library of fully human antibodies was constructed, and a cell line expressing a fusion protein composed of each of extracellular domains 1-3 of KDR(VEGFR-2), fused to Fc, was constructed. Anti-KDR-ScFv antibodies neutralizing KDR were screened from the fully human antibody library in the cell line using purified recombinant KDR D1-D3-Fc fusion proteins.

The screened ScFv antibodies were expressed and purified in bacteria with V5 tagging, and human KDR D1-D3-Fc binding assays and VEGF competition assays were performed in a ScFv-phage particle state. Also, BIAcore analysis was carried out to measure the ScFv-antibody affinity, and 6A6-ScFv having constantly maintained affinity was obtained and converted in the form of IgG.

Also, in the present invention, it was confirmed through Western blotting that 6A6-ScFv inhibited the phosphorylation of an angiogenesis signaling factor ERK in primary cultured HUVEC cells and that this inhibition was dependent on the concentration of 6A6-ScFv.

In another aspect, the present invention relates to a fully human antibody 6A6-IgG neutralizing vascular endothelial growth factor receptor.

FACS analysis revealed that the 6A6-IgG was strongly bound to endogenous human KDR, which was expressed on the surface of living HUVEC cells (ATCC, USA), compared to a commercially available IMC-1C11 IgG chimeric antibody (Imclone, USA), and that, even when the cells were also treated with a competitively binding human $VEGF_{165}$, the 6A6-IgG more effectively neutralized KDR, expressed on the surface of the HUVEC cells, compared to the IMC-1C11 IgG chimeric antibody.

This suggests that the results of the VEGF competition assays in ELISA differ from the results indicating that 6A6-IgG and the IMC-1C11 IgG chimeric antibody neutralized KDR at similar levels. That is, the in vitro assay results and the in vivo assay results can differ from each other and there is a limitation in screening highly efficient antibodies based on the in vitro assay results.

Also, in the present invention, it could be observed that the 6A6-IgG antibody was more strongly bound to KDR, expressed in the human acute myeloid eukemia cell line K562 (ATCC, USA), compared to the IMC-1C11 IgG.

Moreover, in the present invention, it was confirmed through Western blotting that 6A6-IgG inhibited the phosphorylation of the angiogenesis signaling factor ERK in primary cultured HUVEC cells and that this inhibition was increased according t concentration dependent manner of 6A6-IgG.

Also, in the present invention, it was observed that the 6A6-IgG according to the present invention inhibited the chemotactic motility of HUVEC cells moving to an environment having VEGF present therein and that the 6A6-IgG also inhibited the tube formation of HUVEC cells, which is direct angiogenesis action.

Furthermore, in the present invention, in order to confirm that the inhibitory effect of 6A6-IgG on VEGF effects on HUVEC cells is because 6A6-IgG blocks the entrance of VEGF receptors into HUVEC cells, observation with a confocal microscope was performed in an experiment using a KDR antibody labeled with FITC. As a result, it was observed that the VEGF receptor (KDR) could not enter the cells, when cells were treated with 6A6-IgG.

Also, through an ex vivo rat aortic ring assay, it was found that, in rat aortic rings treated with 6A6-IgG, vascular sprouting did not occur. Also, angiogenesis was analyzed through a metrigel plug assay by injecting matrigel subcutaneously into mice.

As a result, in a group treated with VEGF, angiogenesis in plugs was observed, but in a group treated with VEGF along with 6A6-IgG, angiogenesis was not observed, suggesting that 6A6-IgG had an angiogenesis inhibitory effect in vivo.

In still another aspect, the present invention relates to variants obtained by mutating the light chain sequence of 6A6-ScFv through light chain shuffling.

Through the light chain shuffling, 18 light chain variants of 6A6-ScFv were obtained, and the light chain shuffling was performed in the following manner.

(1) In order to prevent 6A6 from being selected again during a biopanning process, DNA of a 6A6 light chain shuffling library was treated with a restriction enzyme SpeI having a recognition site at the CDR3 of 6A6. After the DNA was transfected into ETB cells, a sub-library was constructed, and KDR affinity and VEGF competition assays in ELISA were performed to select clones having excellent KDR neutralizing ability.

(2) In a washing step in the biopanning process, the antibody clones were allowed to compete with soluble KDR to select clones having excellent KDR neutralizing ability.

(3) In a step of allowing phages to bind to the antigen KDR in the biopanning process, IMC-1121B IgG (ImClone, USA) was also added in order to select clones having KDR neutralizing ability which was superior or similar to that of the 1121B IgG.

In still another aspect, the present invention relates to a composition for inhibiting angiogenesis and a composition for treating cancer, which contain said ScFv or IgG.

As used herein, the term "angiogenesis" includes angiogenesis involved in tumor growth and metastasis, age-related macular degeneration, rheumatoid arthritis, diabetic retinopathy, psoriasis and chronic inflammation, but the scope of the present invention is not limited thereto.

In the present invention, said cancer includes, but is not limited to, colon cancer, pancreas cancer, rectal cancer, colorectal cancer, prostate cancer, renal cancer, melanoma, prostate cancer metastasized to bone, ovarian cancer and blood cancer.

The composition of the present invention can be administered by any route suitable for a specific molecule. The composition of the present invention may be provided to animals, including humans, by any suitable means, directly (e.g., locally, such as by injection, subcutaneous injection or topical administration to a tissue locus) or systemically (e.g., parenterally or orally). Where the composition of the present invention is to be provided parenterally, such as by intravenous, subcutaneous, opthalmic, intraperitoneal, intramuscular, buccal, rectal, vaginal, intraorbital, intracerebral, intracranial, intraspinal, intraventricular, intrathecal, intracisternal, intracapsular, intranasal administration or by aerosol administration, the composition preferably comprises part of an aqueous or physiologically compatible fluid suspension or solution. Thus, the carrier or excipient is physiologically acceptable so that in addition to delivery of the desired agent to the subject, the solution does not otherwise adversely affect the subject's electrolyte and/or volume balance. The aqueous medium for the agent thus may comprise normal physiologic saline.

The ScFv or IgG protein of the present invention may be administered for therapeutic treatments to a cancer patient in an amount sufficient to prevent, inhibit, or reduce the progression of the tumor, e.g., the growth, invasiveness, metastases and/or recurrence of the tumor. An amount adequate to accomplish this is defined as a "therapeutically effective dose." Amounts effective for this use will depend upon the severity of the disease and the general state of the patient's own immune system.

The dose of the protein according to the present invention is preferably 0.01-100 mg/kg, and more preferably 0.1-10 mg/m$^2$.

However, the optimal dose will depend upon a disease being treated and the existence of side effects and can be determined using routine experimentation. The administration of the antibody may be by periodic bolus injections, or by continuous intravenous or intraperitoneal administration from an external reservoir (for example, from an intravenous bag) or an internal reservoir (for example, from a bioerodable implant). Furthermore, the antibody proteins of the present invention also may be administered to the intended recipient together with a plurality of different biologically active molecules. However, the optimal combination of fusion protein and other molecules, modes of administration, dosages may be determined by routine experimentation well within the level of skill in the art.

The composition according to the present invention may be used in combination with other therapeutic agents associated with the relevant disease.

There is synergy when tumors, including human tumors, are treated with the VEGF receptor antibody in combination with radiation, chemotherapy, an additional receptor antagonist or a combination thereof. In other words, the inhibition of tumor growth by a VEGF receptor antagonist is enhanced more than expected when combined with chemotherapeutic agents, radiation, or an additional receptor antagonist or combinations thereof. Synergy may be shown, for example, by greater inhibition of tumor growth with combined treatment than it would be expected from the additive effect of treatment with a VEGF receptor antagonist and a chemotherapeutic agent, radiation, or an additional receptor antagonist. Preferably, synergy is demonstrated by remission of the cancer where remission is not expected from treatment with a combination of a VEGF receptor antagonist and a chemotherapeutic agent, radiation, or an additional receptor antagonist.

The VEGF receptor antagonist is administered before, during, or after commencing chemotherapy or radiation therapy, as well as any combination thereof, i.e. before and during, before and after, during and after, or before, during, and after commencing the chemotherapy and/or radiation therapy. For example, when the VEGF receptor antagonist is an antibody, the antibody is typically administered between 1 and 30 days, preferably between 3 and 20 days, more preferably between 5 and 12 days before commencing radiation therapy and/or chemotherapy.

VEGF Receptor Antibody

In one embodiment, the VEGF receptor antibody binds specifically to an epitope on the extracellular domain of a VEGF receptor. The extracellular domain of a VEGF receptor is the ligand-binding domain. The ligand-binding domain may be found at either end of the receptor, but is normally found at the amino-terminal end.

Some examples of VEGF receptors include the protein tyrosine kinase receptors referred to in the literature as Flt-1 (VEGFR-1), KDR and Flk-1 (VEGFR-2). Unless otherwise stated or clearly suggested otherwise by context, this specification will follow the customary literature nomenclature of VEGF receptors. KDR will be referred to as the human form of a VEGF receptor having MW 180 kD (Terman et al., *Oncogene,* 6:1677, 1991). Flk-1 (VEGFR-2) is will be referred to as the murine homolog of KDR (Matthews et al., *PNAS,* 88:9026, 1991). Flt-1 (VEGFR-1) is referred to as a form of VEGF receptor different from, but related to, the KDR/Flk-1 receptor (Shibuya et al., *Oncogene,* 5:519, 1990).

Other VEGF receptors include those that can be cross-link with labeled VEGF, or that can be co-immunoprecipitated with KDR. Some known forms of these VEGF receptors have molecular weights of approximately 170 kD, 150 kD, 130-135 kD, 120-125 kD and 85 kD (Quinn et al., *PNAS,* 90:7533, 1993; Scher et al., *J. Biol. Chem.,* 271:5761, 1996).

The VEGF receptor is usually bound to a cell, such as an endothelial cell. The VEGF receptor may also be bound to a non-endothelial cell, such as a tumor cell. Alternatively, the VEGF receptor may be free from the cell, preferably in soluble form.

The antagonist of the present invention neutralizes VEGF receptors. In this specification, neutralizing a receptor means inactivating the intrinsic kinase activity of the receptor to transduce a signal. A reliable assay for VEGF receptor neutralization is the inhibition of receptor phosphorylation.

The present invention is not limited by any particular mechanism of VEGF receptor neutralization. The mechanism caused by one antagonist is not necessarily the same as that caused by another antagonist. Some possible mechanisms include preventing binding of the VEGF ligand to the extracellular binding domain of the VEGF receptor, and preventing dimerization or oligomerization of receptors. Other mechanisms cannot, however, be ruled out.

A VEGF receptor (or VEGFR) antibody, in the context of the present invention, inhibits activation of the VEGFR subfamily of receptors. By inhibition of activation of the VEGFR subfamily of receptors is meant any decrease in the activation of the VEGFR. That is, the prevention of activation need not completely stop activation of the VEGFR. Moreover, inhibition of VEGFR activation, as defined by the present invention, means inhibition of the VEGFR following interaction of the VEGFR antibody and VEGFR. By association is meant sufficient physical or chemical interaction between the VEGFR and VEGFR antibody which inhibits tyrosine kinase activity of the receptor. One of skill in the art would appreciate those examples of such chemical interactions, which include association or bonding, are known in the art and include covalent bonding, ionic bonding, hydrogen bonding, etc. Accordingly, the VEGFR antagonist of the present invention inhibits the tyrosine kinase activity of the receptor, which prevents autophosphorylation of the receptor and phosphorylation of various other proteins involved in the VEGFR signaling pathways. Such pathways, which are involved in regulation of vasculogenesis and angiogenesis, include any of the following: the phospholipase Cy (PLCy) pathway or the phosphatidylinositol 3' kinase (PI3-K)/Akt and mitogen activated protein kinase (MAPK) pathway (Larrivee et al., *Int. J. Med.*, 5:447, 2000).

The VEGFR subfamily of receptors is characterized by the presence of seven immunoglobulin-like loops in the extracellular domain, a single transmembrane region and a split tyrosine kinase domain in the intracellular region (class III receptor tyrosine kinases). There are several known members of the VEGFR subfamily of receptors, examples of which include VEGFR-1, VEGFR-2, and VEGFR-3.

It is generally believed that KDR (VEGFR-2) is the main VEGF signal transducer that results in endothelial cell proliferation, migration, differentiation, tube formation, increase of vascular permeability, and maintenance of vascular integrity. VEGFR-1 possesses a much weaker kinase activity, and is unable to generate a mitogenic response when stimulated by VEGF, although it binds to VEGF with an affinity that is approximately 10-fold higher than KDR (VEGFR-2). VEGFR-1 has also been implicated in VEGF- and placenta growth factor (P1GF)-induced migration of monocytes and macrophages and production of tissue factor.

As is the case with VEGFR described above, increased VEGFR activation can result from higher levels of ligand, VEGFR gene amplification, increased transcription of the receptor or mutations that cause unregulated receptor signaling.

In one embodiment of the present invention, the VEGFR antibody inhibits binding of VEGFR to its ligand. Binding of a ligand to an external, extracellular domain of VEGFR stimulates receptor dimerization, autophosphorylation of VEGFR, activation of the receptor's internal, cytoplasmic tyrosine kinase domain, and initiation of multiple signal transduction pathways involved in regulation of vasculogenesis and angiogenesis.

Ligands for VEGFR include VEGF and its homologues P1GF, VEGF-B, VEGF-C, VEGF-D, and VEGF-E. For example, P1GF, which is a dimeric secreted factor and only binds VEGFR-1, is produced in large amounts by villous cytotrophoblast, sincytiotrophoblast and extravillous trophoblast and has close amino acid homology to VEGF. Three isoforms exist in humans, P1GF-1, P1GF-2, and P1GF-3. Studies with P1GF-deficient mice demonstrate that this growth factor is not involved in angiogenesis per se, but rather, specifically modulates the angiogenic and permeability effects of VEGF during pathological situations. Also, VEGF-D is closely related to VEGF-C by virtue of the presence of N- and C-terminal extensions that are not found in other VEGF family members. In adult human tissues, VEGF-D mRNA is most abundant in heart, lung, skeletal muscle, colon, and small intestine. Analyses of VEGF-D receptor specificity revealed that VEGF-D is a ligand for both VEGFR-2 (Flk1) and VEGFR-3 (Flt4) and can activate these receptors; however, VEGF-D does not bind to VEGFR-1. In addition, VEGF-D is a mitogen for endothelial cells.

In another embodiment of the present invention, the VEGFR antibody binds specifically to VEGFR. It should be appreciated that the VEGFR antibody can bind externally to the extracellular portion of VEGFR, which may or may not inhibit binding of the ligand, or internally to the tyrosine kinase domain. Preferably, the VEGFR antagonist of the present invention is an antibody, or functional equivalent thereof, specific for VEGFR, details of which are described in more detail below.

In one preferred embodiment, the VEGF receptor antibody binds specifically to KDR. Particularly preferred are antigen-binding proteins that bind to the extracellular domain of KDR and block binding by one or both of its ligands, VEGF and P1GF, and/or neutralize VEGF-induced or P1GF-induced activation of KDR.

There also exist various hybridomas that produce VEGFR-2 antibodies. For example, a hybridoma cell line producing rat anti-mouse VEGFR-2 monoclonal antibody (DC101) was deposited as ATCC HB 11534; a hybridoma cell line (M25. 18A1) producing mouse anti-mouse VEGFR-2 monoclonal antibody mAb 25 was deposited as ATCC HB 12152; and a hybridoma cell line (M73.24) producing mouse anti-mouse VEGFR-2 monoclonal antibody mAb 73 was deposited as ATCC HB 12153.

In addition, various hybridomas that produce anti-VEGFR-1 antibodies exist and include, but are not limited to, hybridomas KM1730 (deposited as FERM BP-5697), KM1731 (deposited as FERM BP-5718), KM1732 (deposited as FERM BP-5698), KM1748 (deposited as FERM BP-5699), KM1750 (deposited as FERM BP-5700) disclosed in WO 98/22616, WO 99/59636, AU 5066698 B2, and CA 2328893.

Many other VEGFR antagonists are known in the art. Some examples of VEGFR antagonists are described in U.S. Pat. Nos. 5,185,438; 5,621,090; 5,283,354; 5,270,458; 5,367,057; 5,548,065; 5,747,651; 5,912,133; 6,677,434; 6,960,446; 5,840,301; 5,861,499; 6,365,157; 5,955,311; 6,365,157; 6,811,779; and WO 2001/66063. U.S. Pat. No. 5,861,301, Terman et al., *Oncogene*, 6:1677, 1991, WO 94/10202, and WO 95/21865, disclose VEGF antagonists and, specifically, anti-VEGFR-2 antibodies. In addition, anti-VEGFR-2 antibodies are disclosed in U.S. Pat. No. 6,177,401 and 5,712, 395. U.S. Pat. No. 5,981,569 discloses VEGFR antagonists that are organic molecules. Also, bi-specific antibodies (BsAbs), which are antibodies that have two different antigen-binding specificities or sites, directed against KDR (VEGFR-2) and VEGFR-1 are known. Also, Hennequin et al., *J. Med. Chem.*, 42:5369, 1999 discloses certain quinazolines, quinolines and cinnolines as being useful as VEGF receptor antagonists (Annie et al., *J. Acqu. Immune Defic. Syn. and Hum. Retrovirol.*, 17: A41, 1998).

Furthermore, assays for the determination of VEGFR antibodies are known in the art. The VEGFR antibodies of the present invention inhibit the tyrosine kinase activity of VEGFR, which generally involves phosphorylation events. Accordingly, phosphorylation assays are useful in determining VEGFR antibodies in the present invention. Some assays for tyrosine kinase activity are described in Panek et al., *J. Pharmacol. Exp. Thera.*, 283:1433, 1997 and Batley et al., *Life Sci.*, 62:143, 1998. In addition, methods specific for detection of VEGFR expression can be utilized.

Antibodies

The antibodies of the present invention may be produced by methods known in the art (Kohler and Milstein, *Nature*, 256:495, 1975; Campbell, Monoclonal Antibody Technology, The Production and Characterization of Rodent and Human Hybridomas; Burdon et al., Eds., Laboratory Techniques in Biochemistry and Molecular Biology, Vol. 13, Elsevier Science Publishers, Amsterdam, 1985; Huse et al., *Science*, 246:1275, 1989). The antibodies of the present invention can be monoclonal or polyclonal antibodies or any other suitable type of an antibody, such as a fragment or a derivative of an antibody, a single chain variable fragmen (ScFv) or a synthetic homolog of the antibody, provided that the antibody has the same binding characteristics as, or that has binding characteristics comparable to, those of the whole antibody. As used herein, unless otherwise indicated or clear from the context, antibody domains, regions and fragments follow standard definitions as are well known in the art (Abbas et al., Cellular and Molecular Immunology, W.B. Saunders Company, Philadelphia, Pa., 1991). Preferably, the antibodies of the present invention are monoclonal antibodies.

Antibody fragments can be produced by cleaving a whole antibody, or by expressing DNA that encodes the fragment. Fragments of antibodies may be prepared by methods described in the published literature (Lamoyi et al., *J. Immunol. Methods*, 56:235, 1983; Parham, *J. Immunol.*, 131:2895, 1983). Such fragments may contain one or both of an Fab fragment and an F(ab')2 fragment. Such fragments may also contain single chain variable fragment antibodies, i.e. scFv, dibodies, or other antibody fragments. Methods of producing such functional equivalents are disclosed in WO 93/21319, EP 239,400, WO 89/09622, EP 338,745 and EP 332,424.

Single chain variable fragments (scFv) are polypeptides that consist of the variable region of a heavy chain of an antibody linked to the variable region of a light chain with a short peptide linker). Thus, the scFv comprises the entire antibody-combining site. These chains may be produced in bacteria, or in eukaryotic cells. A typical example of a single chain antibody in the present invention is 6A6-ScFv (TTAC-0001). 6A6-ScFv was shown to block VEGF-KDR (VEGF-VEGFR-2) interaction and inhibit VEGF-stimulated receptor phosphorylation. This 6A6-ScFv binds both to soluble KDR (VEGFR-2) and cell surface-expressed KDR (VEGFR-2) on HUVEC cells and K562 cells. The 6A6-ScFv has a light chain sequence of SEQ ID NO: 35 and a heavy chain sequence of SEQ ID NO: 36. The 6A6-ScFv antibody is a fully human antibody and can be constructed with Fab', F(ab')2, bivalent ScFv, bivalent recombinant ScFv or human IgG antibodies.

Preferably, although the antibody fragments contain all six complementarity-determining regions (CDRs) of the whole antibody, fragments containing fewer than all of such regions, such as three, four or five CDRs, may also be functional. If the antibody fragment is too short to be immunogenic, it may be conjugated to a carrier molecule. Some suitable carrier molecules include keyhole limpet hemocyanin and bovine serum albumen. Conjugation may be carried out by methods known in the art.

Antibodies of the present invention also include antibodies whose binding characteristics can be improved by direct mutation, methods of affinity maturation, phage display, or chain shuffling. Affinity and specificity may be modified or improved by mutating CDRs and screening for antigen binding sites having the desired characteristics (Yang et al., *J. Mol. Biol.*, 254:392, 1995). CDRs are mutated in a variety of ways. One way is to randomize individual residues or combinations of residues so that in a population of otherwise identical antigen binding sites, all twenty amino acids are found at particular positions. Alternatively, mutations are induced over a range of CDR residues by error prone PCR methods ((Hawkins et al., *J. Mol. Biol.*, 226:889, 1992). Phage display vectors containing heavy and light chain variable region genes are propagated in mutator strains of *E. coli* (Low et al., *J. Mol. Biol.*, 250:359, 1996). These methods of mutagenesis are illustrative of the many methods known to one of skill in the art.

Antibodies, and particularly monoclonal antibodies, can be produced by methods known in the art. Examples for production of antibodies include, but are not limited to, production in hybridoma cells and transformation of mammalian cells with DNA encoding the receptor antagonist. These methods are described in various publications (Kohler and Milstein, *Nature*, 256:495, 1975; Campbell in "Monoclonal Antibody Technology, The Production and Characterization of Rodent and Human Hybridomas" in Burdon et al, Eds., Laboratory Techniques in Biochemistry and Molecular Biology, Vol. 13, Elsevier Science Publishers, Amsterdam, 1985; Huse et al., *Science*, 246:1275, 1989).

Equivalents of antibodies are also prepared by methods known in the art. For example, fragments of antibodies may be prepared enzymatically from whole antibodies. Preferably, equivalents of antibodies are prepared from DNA encoding such equivalents. DNA encoding fragments of antibodies may be prepared by deleting all but the desired portion of the DNA that encodes the full-length antibody. DNA encoding chimerized antibodies may be prepared by recombining DNA encoding human constant regions, derived substantially or exclusively from the corresponding human antibody regions, and DNA encoding variable regions, derived substantially or exclusively from the sequence of the variable region of a mammal other than a human. DNA encoding humanized antibodies may be prepared by recombining DNA encoding constant regions and variable regions other than the complementarity determining regions (CDRs), derived substantially or exclusively from the corresponding human antibody regions, and DNA encoding CDRs, derived substantially or exclusively from a mammal other than a human.

Suitable sources of DNA molecules that encode fragments of antibodies include cells, such as hybridomas, that express the full-length antibody. The fragments may be used by themselves as antibody equivalents, or may be recombined into equivalents, as described above. The DNA deletions and recombinations described in this section may be carried out by known methods, such as those described in the published patent applications listed above in the section entitled "Functional Equivalents of Antibodies" and/or other standard recombinant DNA techniques, such as those described below.

Preferred host cells for transformation of vectors and expression of the antibodies of the present invention are mammalian cells, e.g., COS-7 cells, Chinese hamster ovary (CHO) cells, and cell lines of lymphoid origin such as lymphoma, myeloma, or hybridoma cells. Other eukaryotic host, such as yeasts, can be alternatively used. For example, mouse fetal liver stromal cell line 2018 binds to APtag-Flk 1 and APtag-Flk-2 fusion proteins, i.e., contains ligands of VEGFR-2 and Flk-2 (ATCC, Manassas, Va., CRL 10907), human fetal spleen cell line Fsp 62891 contains Flk-2 ligand (ATCC CRL 10935), and human stromal fetal thymus cell line, F. thy 62891, contains VEGFR-2 ligand (ATCC CRL 10936).

As used herein, the term "vector" means any nucleic acid comprising a competent nucleotide sequence to be incorporated into a host cell and to be recombined with and integrated into the host cell genome, or to replicate autonomously as an episome. Such vectors include linear nucleic acids, plasmids, phagemids, cosmids, RNA vectors, viral vectors and the like.

Examples of a viral vector include, but is not limited to, a retrovirus, an adenovirus and an adeno-associated virus.

As used herein, the term "gene expression" or "expression of a target protein" is understood to mean the transcription of a DNA sequence, the translation of an mRNA transcript and the secretion of an Fc fusion protein product.

In the present invention, suitable host cells can be transformed or transfected with DNA and can be used to express and/or secrete target proteins. Preferred host cells for use in the present invention include immortalized hybridoma cells, NS/O myeloma cells, 293 cells, Chinese hamster ovary (CHO) cells, HELA cells and COS cells.

The transformed host cells are cultured by methods known in the art in a liquid medium containing assimilable sources of carbon (carbohydrates such as glucose or lactose), nitrogen (amino acids, peptides, proteins or their degradation products such as peptones, ammonium salts or the like), and inorganic salts (sulfates, phosphates and/or carbonates of sodium, potassium, magnesium and calcium). The medium additionally contains, for example, growth-promoting substances, such as trace elements, for example iron, zinc, manganese and the like.

Where it is desired to express a gene construct in yeast, a suitable selection gene for use in yeast is the trp1 gene present in the yeast plasmid YRp7 (Stinchcomb et al., *Nature*, 282:39, 1979; Kingsman et al., *Gene*, 7:141, 1979). The trp1 gene provides a selection marker for a mutant strain of yeast lacking the ability to grow in tryptophan, for example, ATCC 44076 or PEP4-1 (Jones, *Genetics*, 85:12, 1977). The presence of the trp1 lesion in the yeast host cell genome then provides an effective environment for detecting transformation by growth in the absence of tryptophan. Similarly, Leu2-deficient yeast strains (ATCC 20622 or 38626) are complemented by known plasmids bearing the Leu2 gene.

Alternatively, the DNA encoding the receptor antagonist can be cloned into vectors derived from viruses such as adenovirus, adeno-associated virus, herpesvirus, retrovirus or lentivirus. Gene expression is controlled by inducible or uninducible regulatory sequences.

Briefly, a suitable source of cells containing nucleic acid molecules that express the desired DNA, such as an antibody, antibody equivalent or VEGF receptor, is selected. Total RNA is prepared by standard procedures from a suitable source. The total RNA is used to direct cDNA synthesis. Standard methods for isolating RNA and synthesizing cDNA are provided in standard manuals of molecular biology such as, for example, those described above.

The cDNA may be amplified by known methods. For example, the cDNA may be used as a template for amplification by polymerase chain reaction (PCR) (Saiki et al., *Science*, 239:487, 1988; U.S. Pat. No. 4,683,195). The sequences of the oligonucleotide primers for the PCR amplification are derived from the known sequence to be amplified. The oligonucleotides are synthesized by methods known in the art (Caruthers, *Science*, 230:281, 1985).

A mixture of upstream and downstream oligonucleotides is used in the PCR amplification. The conditions are optimized for each particular primer pair according to standard procedures. The PCR product is analyzed, for example, by electrophoresis for cDNA having the correct size, corresponding to the sequence between the primers. Alternatively, the coding region may be amplified in two or more overlapping fragments. The overlapping fragments are designed to include a restriction site permitting the assembly of the intact cDNA from the fragments.

In order to isolate the entire protein-coding regions for the VEGF receptors, for example, the upstream PCR oligonucleotide primer is complementary to the sequence at the 5' end, preferably encompassing the ATG start codon and at least 5-10 nucleotides upstream of the start codon. The downstream PCR oligonucleotide primer is complementary to the sequence at the 3' end of the desired DNA sequence. The desired DNA sequence preferably encodes the entire extracellular portion of the VEGF receptor, and optionally encodes all or part of the transmembrane region, and/or all or part of the intracellular region, including the stop codon.

The DNA to be amplified, such as that encoding antibodies, antibody equivalents, or VEGF receptors, may also be replicated in a wide variety of cloning vectors in a wide variety of host cells. The host cell may be prokaryotic or eukaryotic.

The vector into which the DNA is spliced may comprise segments of chromosomal, non-chromosomal and synthetic DNA sequences. Some suitable prokaryotic cloning vectors include plasmids derived from *E. coli*, such as colE1, pCRI, pBR322, pMB9, pKSM, and RP4. Prokaryotic vectors also include derivatives of phage DNA such as M13 and other filamentous single-stranded DNA phages. A preferred vector for cloning nucleic acid encoding the VEGF receptor is the Baculovirus vector.

The vector containing the DNA to be expressed is transfected into a suitable host cell. The host cell is maintained in an appropriate culture medium, and subjected to conditions under which the cells and the vector replicate. The vector may be recovered from the cell. The DNA to be expressed may be recovered from the vector.

The DNA to be expressed, such as that encoding antibodies, antibody equivalents, or receptors, may be inserted into a suitable expression vector and expressed in a suitable prokaryotic or eukaryotic host cell.

For example, the DNA inserted into a host cell may encode the entire extracellular portion of the VEGF receptor, or a soluble fragment of the extracellular portion of the VEGF receptor. The extracellular portion of the VEGF receptor encoded by the DNA is optionally attached at either, or both, the 5' end or the 3' end to additional amino acid sequences. The additional amino acid sequences may be attached to the VEGF receptor extracellular region, such as the leader sequence, the transmembrane region and/or the intracellular region of the VEGF receptor. The additional amino acid sequences may also be sequences not attached to the VEGF receptor in nature. Preferably, such additional amino acid sequences serve a particular purpose, such as to improve expression levels, secretion, solubility, or immunogenicity.

Vectors for expressing proteins in bacteria, especially *E. coli*, are known (Dieckmann and Tzagoloff, *J. Biol. Chem.*, 260:1513, 1985). These vectors contain DNA sequences that encode anthranilate synthetase (TrpE) followed by a polylinker at the carboxy terminus. Other expression vector systems are based on beta-galactosidase (pEX); lambda PL; maltose binding protein (pMAL); and glutathione S-transferase (pGST) (*Gene*, 67:31, 1988; *Peptide Research*, 3:167, 1990).

Suitable vectors for expression in mammalian cells are also known. Such vectors include well-known derivatives of SV-40, adenovirus, retrovirus-derived DNA sequences and shuttle vectors derived from combination of functional mammalian vectors, such as those described above, and functional plasmids and phage DNA.

Additional vectors for expression of eukaryotic cells are known in the art (Southern, P. J. and Berg, P., *J. Mol. Appl. Genet.*, 1:327, 1982; Subramani et al, *Mol. Cell. Biol.*, 1:854, 1981; Kaufinann and Sharp, *J. Mol. Biol.*, 159:601, 1982; Kaufinann and Sharp, *Mol. Cell. Biol.*, 1982; Scahill et al., *PNAS*, 80:4654, 1983; Urlaub and Chasin, *PNAS*, 77:4216, 1980). The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences include the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters of SV40, and other sequences known to control the expression of genes of prokaryotic or eukaryotic cells and their viruses.

Vectors containing the control signals and DNA to be expressed, such as that encoding antibodies, antibody equivalents, or VEGF receptors, are inserted into a host cell for expression. Some useful expression host cells include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRCI, *Pseudomonas, Bacillus*, such as *Bacillus subtilis*, and *Streptomyces*. Suitable eukaryotic cells include yeast and other fungi, insect, animal cells, such as COS cells and CHO cells, human cells and plant cells in tissue culture.

Following expression in a host cell maintained in a suitable medium, the polypeptide or peptide to be expressed, such as antibodies, antibody equivalents, or VEGF receptors, may be isolated from the medium, and purified by methods known in the art. If the polypeptide or peptide is not secreted into the culture medium, the host cells are lysed prior to isolation and purification.

In addition, the antibodies of the invention may be prepared by immunizing a mammal with a soluble receptor. The soluble receptors themselves may be used as immunogens, or may be attached to a carrier protein or to other objects, such as beads, i.e., sepharose beads. After the mammal has produced antibodies, a mixture of antibody-producing cells, such as the splenocytes, is isolated. Monoclonal antibodies may be produced by isolating individual antibody-producing cells from the mixture and making the cells immortal by, for example, fusing them with tumor cells, such as myeloma cells. The resulting hybridomas are preserved in culture, and express monoclonal antibodies, which are harvested from the culture medium.

The antibodies may also be prepared from receptors bound to the surface of cells that express the specific receptor of interest. The cell to which the receptors are bound may be a cell that naturally expresses the receptor, such as a vascular endothelial cell for VEGFR. Alternatively, the cell to which the receptor is bound may be a cell into which the DNA encoding the receptor has been transfected, such as 3T3 cells, which have been transfected with VEGFR.

A receptor may be used as an immunogen to raise an antibody of the present invention. The receptor peptide may be obtained from natural sources, such as from cells that express the receptors. For example, the VEGF receptor peptide may be obtained from vascular endothelial cells. Alternatively, synthetic receptor peptides may be prepared using commercially available machines. In such an embodiment, the VEGF receptor amino acid sequence can be provided through the published literatures (Shibuya et al., *Oncogene,* 5:519, 1990; PCT/US92/01300; Terman et al., Oncogene, 6:1677, 1991; Matthews et al., *PNAS,* 88:9026, 1991).

As an alternative, DNA encoding a receptor, such as a cDNA or a fragment thereof, is cloned and expressed, and the resulting polypeptide is recovered and thus it may be used as an immunogen to raise an antibody of the present invention. For example, in order to prepare the VEGF receptors against which the antibodies are made, nucleic acid molecules that encode the VEGF receptors of the present invention, or portions thereof, especially the extracellular portions thereof, may be inserted into known vectors for expression in host cells using standard recombinant DNA techniques, such as those described below. Suitable sources of such nucleic acid molecules include cells that express VEGF receptors, i.e., vascular endothelial cells.

The antibody may be prepared in any mammal; suitable mammals other than human include, for example, a rabbit, rat, mouse, horse, goat, or primate. Mice are frequently used to prepare monoclonal antibodies. The antibody may be a member of one of the following immunoglobulin classes: IgG, IgM, IgA, IgD, or IgE, and the subclasses thereof, and preferably is an IgG1 antibody. The antibodies of the present invention and their functional equivalents may be or may combine members of any of the immunoglobulin classes.

Neutralization of VEGF Activation of VEGF Receptors

Neutralization of activation of a VEGF receptor in a sample of endothelial or non-endothelial cells, such as tumor cells, may be performed in vitro or in vivo. Neutralizing VEGF activation of a VEGF receptor in a sample of VEGF-receptor expressing cells comprises contacting the cells with the antibody of the present invention. The cells are contacted in vitro with the antibody, before, simultaneously with, or after, adding VEGF to the cell sample.

In vivo, the antibody of the present invention is contacted with a VEGF receptor by administration to a mammal. Methods of administration to a mammal include, for example, oral, intravenous, intraperitoneal, subcutaneous, or intramuscular administration.

This in vivo neutralization method is useful for inhibiting angiogenesis in a mammal. Angiogenesis inhibition is a useful therapeutic method, such as for preventing or inhibiting angiogenesis associated with pathological conditions such as tumor growth. Accordingly, the the antibody of the present invention is an anti-angiogenic and anti-tumor immunotherapeutic agent.

As used herein the term "mammal" means any mammal. Some examples of mammals include pet animals, such as dogs and cats; farm animals, such as pigs, cattle, sheep, and goats; laboratory animals, such as mice and rats; primates, such as monkeys, apes, and chimpanzees; and humans.

VEGF receptors are found on some non-endothelial cells, such as tumor cells, indicating the unexpected presence of an autocrine and/or paracrine loop in these cells. The antagonists, e.g., the antibodies, of this invention are useful in neutralizing the activity of VEGF receptors on such cells, thereby blocking the autocrine and/or paracrine loop, and inhibiting tumor growth. The methods of inhibiting angiogenesis and of inhibiting pathological conditions such as tumor growth in a mammal comprise administering an effective amount of any one of the inventive antagonists, e.g., antibodies, including any of the functional equivalents thereof, systemically to a mammal, or directly to a tumor within the mammal. The mammal is preferably human. This method is effective for treating subjects with both solid tumors, preferably highly vascular tumors, and non-solid tumors.

The inhibition or reduction of tumor growth includes the prevention or inhibition of the progression of a tumor, including cancerous and noncancerous tumors. The progression of a tumor includes the invasiveness, metastasis, recurrence and increase in size of the tumor. The inhibition or reduction of tumor growth also includes the destruction of a tumor.

All types of tumors may be treated by the methods of the present invention. The tumors may be solid or non-solid.

Some examples of solid tumors that can be treated with the antagonists of the present invention include carcinomas, sarcomas, blastomas or gliomas. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kapos's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes.

Some examples of non-solid tumors include leukemias, multiple myelomas and lymphomas. Some examples of leukemias include acute myelocytic leukemia (AML), chronic myelocytic leukemia (CML), acute lymphocytic leukemia (ALL), chronic lymphocytic leukemia (CLL), erythrocytic leukemia or monocytic leukemia. Some examples of lymphomas include lymphomas associated with Hodgkin's disease and non-Hodgkin's disease.

Preventing or inhibiting angiogenesis is also useful to treat non-neoplastic pathologic conditions characterized by excessive angiogenesis, such as neovascular glaucoma, proliferative retinopathy including proliferative diabetic retinopathy, arthritis, macular degeneration, hemangiomas, angiofibromas, and psoriasis.

Using Inventive Antibodies to Isolate and Purify VEGF Receptor

The antagonists of the present invention may be used to isolate and purify the VEGF receptor using conventional methods such as affinity chromatography (Dean et al., Affinity Chromatography: A Practical Approach, IRL Press, Arlington, Va., 1985). Other methods well known in the art include magnetic separation with antibody-coated magnetic beads, "panning" with an antibody attached to a solid matrix, and flow cytometry (FACS).

The source of the VEGF receptor is typically vascular cells, and especially vascular endothelial cells, that express the VEGF receptor. Suitable sources of vascular endothelial cells are blood vessels, such as umbilical cord blood cells, especially, human umbilical cord vascular endothelial cells (HU-VEC).

The VEGF receptors may be used as a starting material to produce other materials, such as antigens for making additional monoclonal and polyclonal antibodies that recognize and bind to the VEGF receptor or other antigens on the surface of VEGF-expressing cells.

Using Inventive Antibodies to Isolate and Purify KDR Positive Tumor Cells

The antibodies of the present invention may be used to isolate and purify Flk-1 KDR (VEGFR-2) positive tumor cells, i.e., tumor cells expressing KDR, using conventional methods such as affinity chromatography (Dean, P. D. G. et al., Affinity Chromatography: A Practical Approach, IRL Press, Arlington, Va., 1985). Other methods well known in the art include magnetic separation with antibody-coated magnetic beads, cytotoxic agents, such as complement, conjugated to the antibody, "panning" with an antibody attached to a solid matrix, and flow cytometry (FACS).

Monitoring Levels of VEGF and VEGF Receptors In Vitro or In Vivo

The antibodies of the present invention may be used to monitor the levels of VEGF or VEGF receptors in vitro or in vivo in biological samples using standard assays and methods known in the art. Some examples of biological samples include bodily fluids, such as blood. Standard assays involve, for example, labeling the antibodies and conducting standard immunoassays, such as radioimmunoassays, as is well know in the art.

Standard recombinant DNA techniques useful in carrying out the present invention are described in the literature (Sambrook et al., "Molecular Cloning, "Second Edition, Cold Spring Harbor Laboratory Press, 1987; Ausubel et al, (Eds) "Current Protocols in Molecular Biology, "Green Publishing Associates/Wiley-Interscience, New York, 1990).

Administration

The receptor antibodies of the present invention can be administered for therapeutic treatments to a patient suffering from a tumor in an amount sufficient to prevent, inhibit, or reduce the progression of the tumor, e.g., the growth, invasiveness, metastases and/or recurrence of the tumor. An amount adequate to accomplish this purpose is defined as a therapeutically effective dose. Amounts effective for this use will depend upon the severity of the disease and the general state of the patient's own immune system. Dosing schedules will also vary depending on the disease state and status of the patient, and will typically range from a single bolus dosage or continuous infusion to multiple administrations per day (e.g., every 4-6 hours), or as indicated by the treating physician and the patient's condition. It should be noted, however, that the present invention is not limited to any particular dose.

The present invention can be used to treat any suitable tumor, including, for example, tumors of the breast, heart, lung, small intestine, colon, spleen, kidney, bladder, head and neck, ovary, prostate, brain, pancreas, skin, bone, bone marrow, blood, thymus, uterus, testicles, cervix or liver. Preferably, the methods of the present invention are used when the tumor is a tumor of the colon or when the tumor is a non-small cell lung carcinoma (NSCLC).

Furthermore, the tumors of the present invention preferably have aberrant expression or signaling of VEGFR. Enhanced signaling by VEGFR has been observed in many different human cancers. High levels of VEGFR-2 are expressed by endothelial cells that infiltrate gliomas (Plate et al., *Nature,* 359:845, 1992). VEGFR-2 levels are specifically upregulated by VEGF produced by human glioblastomas (Plate et al., *Cancer Res.,* 53:5822, 1993). The finding of high levels of VEGFR-2 expression in glioblastoma associated endothelial cells (GAEC) indicates that receptor activity is probably induced during tumor formation since VEGFR-2 transcripts are barely detectable in normal brain endothelial cells. This upregulation is confined to the vascular endothelial cells in close proximity to the tumor.

The present invention is useful for inhibition or reduction of tumor growth. By inhibition or reduction of tumor growth is meant prevention, inhibition, or reduction of the progression of the tumor, e. g, the growth, invasiveness, metastases and/or recurrence of the tumor. In addition, the present invention can also be useful in treating an angiogenic condition, such as atherosclerosis, arthritis, macular degeneration and psoriasis. The identification of those patients that have conditions for which the present invention is useful is well within the ability and knowledge of one skilled in the art.

In the present invention, any suitable method or route can be used to administer the VEGFR antibodies, for example, oral, intravenous, intraperitoneal, subcutaneous, or intramuscular administration. The dose of antagonist administered depends on numerous factors, including, for example, the type of antibodies, the type and severity of tumor to be treated and the route of administration of the antibodies. It should be emphasized, however, that the present invention is not limited to any particular method or route of administration.

In one alternative embodiment, the VEGFR antagonist and can be administered in combination with one or more antineoplastic agents (U.S. Pat. No. 6,217,866). Any suitable antineoplastic agent can be used, such as a chemotherapeutic agent or radiation. Examples of chemotherapeutic agents include, but are not limited to, cisplatin, doxorubicin, paclitaxel, irinotecan (CPT-11), topotecan or a combination thereof. When the antineoplastic agent is radiation, the source of the radiation can be either external (external beam radiation therapy-EBRT) or internal (brachytherapy-BT) to the patient being treated. The dose of antineoplastic agent administered depends on numerous factors, including, for example, the type of agent, the type and severity of tumor being treated and the route of administration of the agent. It should be emphasized, however, that the present invention is not limited to any particular dose.

In an additional alternative embodiment, the VEGFR antibody of the present invention can be administered in combination with one or more suitable adjuvants, such as, for example, cytokines (for example, IL-10 and IL-13) or other immune stimulators. See, for example, Larrivee et al., supra. It should be appreciated, however, that administration of only the VEGFR antagonist is sufficient to prevent, inhibit, or reduce the progression of the tumor in a therapeutically effective manner.

In addition, the VEGFR antibody can be administered as a ligand conjugate, which binds specifically to the receptor and delivers a toxic, lethal payload following ligand-toxin internalization. Conjugates between toxins and the receptors were designed with the aim of developing toxic agents specific for EGFR- or VEGFR-overexpressing tumor cells while minimizing nonspecific toxicity. For example, a conjugate composed of EGF and *Pseudomonas* endotoxin (PE) was shown to be toxic toward EGFR-expressing HeLa cells in vitro. Various agents, including thioridazine and adenovirus, can enhance cellular uptake of the conjugate, as well as increase the cytotoxicity of the conjugate.

It is understood that the VEGFR antibodies of the present invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions for the injection may, as is well known in the art, be formulated so as to provide quick, sustained or delayed release of the active ingredient after administration to the mammal.

The VEGFR antibodies of the present invention may be in a variety of forms. These include, for example, solid, semi-solid and liquid dosage forms, such as tablets, pills, powders, liquid solutions, dispersions or suspensions, liposomes, suppositories, injectable and infusible solutions. The preferred form depends on the intended mode of administration and therapeutic application.

Such antibodies can be prepared in a manner well known in the pharmaceutical art. In making the composition, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material, which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions, suspensions, sterile packaged powders, and a topical patch.

Radiation

The source of radiation, used in combination with a VEGF receptor antagonist, can be either external or internal to the patient being treated. When the source is external to the patient, the therapy is known as external beam radiation therapy (EBRT). When the source of radiation is internal to the patient, the treatment is called brachytherapy (BT).

The radiation is administered in accordance with well known standard techniques using standard equipment manufactured for this purpose, such as AECL Theratron and Varian Clinac. The dose of radiation depends on numerous factors as is well known in the art. Such factors include the organ being treated, the healthy organs in the path of the radiation that might inadvertently be adversely affected, the tolerance of the patient to radiation therapy, and the area of the body in need of treatment. The dose will typically be between 1 and 100 Gy, and more particularly between 2 and 80 Gy. Some doses that have been reported include 35 Gy to the spinal cord, 15 Gy to the kidneys, 20 Gy to the liver, and 65-80 Gy to the prostate. It should be emphasized, however, that the present invention is not limited to any particular dose. The dose will be determined by treating physician in accordance with particular factors in a given situation, including the factors mentioned above.

The distance between the source of the external radiation and the point of entry into the patient may be any distance that represents an acceptable balance between killing target cells and minimizing side effects. Typically, the source of the external radiation is between 70 cm and 100 cm from the point of entry into the patient.

Brachytherapy is generally carried out by placing the source of radiation in the patient. Typically, the source of radiation is placed approximately 0-3 cm from the tissue being treated. Known techniques include interstitial, intercavitary, and surface brachytherapy. The radioactive seeds can be implanted permanently or temporarily. Some typical radioactive atoms that have been used in permanent implants include iodine-125 and radon. Some typical radioactive atoms that have been used in temporary implants include radium, cesium-137, and iridium-192. Some additional radioactive atoms that have been used in brachytherapy include americium-241 and gold-198.

The dose of radiation for brachytherapy can be the same as that mentioned above for external beam radiation therapy. In addition to the factors mentioned above for determining the dose of external beam radiation therapy, the nature of the radioactive atom used is also taken into account in determining the dose of brachytherapy.

Chemotherapy

Chemotherapeutic agents include all chemical compounds that are effective in inhibiting tumor growth. The administration of chemotherapeutic agents can be accomplished in a variety of ways including systemically by the parenteral and enteral routes. In one embodiment, the VEGF receptor antagonist and the chemotherapeutic agent are administered as separate molecules. In another embodiment, the VEGF receptor antagonist is attached, for example, by conjugation, to a chemotherapeutic agent.

Examples of chemotherapeutic agents include alkylating agents, for example, nitrogen mustards, ethyleneimine compounds and alkyl sulphonates; antimetabolites, for example, folic acid, purine or pyrimidine antagonists; mitotic inhibitors, for example, vinca alkaloids and derivatives of podophyllotoxin; cytotoxic antibiotics; compounds that damage or interfere with DNA expression.

Additionally, chemotherapeutic agents include antibodies, biological molecules and small molecules, as described herein. Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNE), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol and combinations thereof.

The present invention also includes kits for inhibiting tumor growth comprising a therapeutically effective amount of an EGFR antagonist and a therapeutically effective amount of a VEGFR antagonist. The EGFR or VEGFR antagonist of the inventive kits can be any suitable antagonist, examples of which have been described above. Preferably, the EGFR antagonist of the kit comprises an antibody or functional equivalent thereof, specific for EGFR. Alternatively, and also preferably, the EGFR antagonist of the kit comprises a small molecule specific for EGFR. The VEGFR antagonist of the kit preferably comprises an antibody or functional equivalent thereof, specific for VEGFR. Alternatively, the VEGFR antagonist of the kit preferably comprises a small molecule specific for VEGFR. In addition, the kits of the present invention can further comprise an antineoplastic agent. Examples of suitable antineoplastic agents in the context of the present invention have been described herein. The kits of the present invention can further comprise an adjuvant, examples of which have also been described above.

Accordingly, the receptor antibodies of the present invention can be used in vivo and in vitro for investigative, diagnostic, prophylactic, or treatment methods, which are well known in the art. Of course, it is to be understood and expected that variations in the principles of invention herein disclosed can be made by one skilled in the art and it is intended that such modifications are to be included within the scope of the present invention.

EXAMPLES

Hereinafter, the present invention will be described in further detail. It is to be understood, however, that these examples are illustrative purpose only and are not to be construed to limit the scope of the present invention.

Example 1

Establishment of KDR-Fc Secreting Cell Line

The gene corresponding to the extracellular domains (ECDs) 1-3 of the KDR gene (accession no. AF063658 in GenBank) was amplified from a human placental cDNA library (Clonetech, USA). The amplification was carried out using the primers KDR 1F (SEQ ID NO: 21) and KDR 3R (SEQ ID NO: 22) having BamHI and NheI digestion sites respectively.

```
                                   SEQ ID NO: 21:
    5'-CGC GGATCC ATGGAG AGCAA-3'

SEQ ID NO: 22:
    5'-CCGCTAGC TTTTTCATGGACCCTGACA-3'
```

To produce a KDR(ECD1-3)-Fc chimeric protein, a pcDNA3-BACE-Fc vector (Korean Patent Publication 10-2005-0032177) composed of a BACE-Fc protein gene inserted into a pcDNA3 vector (Invitrogen, USA) was digested with BamHI and NheI, and then ligated with the PCR fragment digested with the same restriction enzymes. The Fc domain was amplified by PCR using the primers ThFc-F (SEQ ID NO: 23) and MycFc-R (SEQ ID NO: 24) so as to have a thrombin digestion site and a myc tag, and the amplified fragment was ligated with the vector using NheI and XhoI sites, thus constructing pcDNA3-KDR D123tFcm.

```
                                   SEQ ID NO: 23:
    5'-CCGCTAGCAGCGGCCTGGTGCCGCGCGGCAGCG

ACAAAACTCAC-3':

SEQ ID NO: 24:
    5'-GGCTCGAGTCACAGGTCTTCCTCAGAGATCA

GC TTCTGCTCTTACCCGGAGAC-3'
```

The pcDNA3-KDR D123tFcm consists of a base sequence encoding amino acid residues 1-327 comprising the secretion signal sequence and extracellular domain of human KDR, a base sequence encoding a thrombin recognition site (SS-GLVPRGS), a base sequence encoding 227 amino acids corresponding to the Fc domain of human immunoglobulin G (hIgG), and a base sequence (EQKLISEEDL) encoding the myc tag (FIG. 1).

For epitope mapping of antibodies, KDR (ECD1-2)-Fc (amino acid residues 1-222) and KDR(ECD2-3)-Fc (amino acid residues 1-327 (Δ24-116)) were prepared. To clone KDR (ECD1-2), the prepared sequence was amplified by PCR using a primer KDR 1F (5'-CGC GGATCC ATGGAG AGCAA: SEQ ID NO: 25) and a primer KDR 12R (5'-CTA GCTAGC CCTAT ACCCT ACAAC GACA-3': SEQ ID NO: 26), and then the PCR amplified fragment was inserted into pcDNA3-KDR D123tFcm digested with BamHI and NheI, thus preparing pcDNA3-KDR D12tFcm. To clone KDR (ECD2-3), a PCR fragment of the primer KDR 1F and the primer KDR 23SR (SEQ ID NO: 26) and a PCR fragment of the primer KDR 23SF (SEQ ID NO: 27) and the primer KDR 23R (SEQ ID NO: 28) were amplified by overlap PCR. The resulting PCR fragment was inserted into pcDNA3-KDR D123tFcm using BamHI and NheI sites, thus preparing pcDNA3-KDR D23tFcm (FIG. 2).

SEQ ID NO: 26:
5'-ACA TAACCC ACAG AGGCG GCCCGGG TCTCCA-3'

SEQ ID NO: 27:
5'-GACCCGGGCCGCCTCTGTGGGTTATGTTCAAGATTACAGA-3'

SEQ ID NO: 28:
5'-CTA GCTAGC TTTTTCA TGGACCCTGACA-3'

To produce a KDR(ECD)-Fc chimeric protein, the above-prepared pcDNA3-KDR D123tFcm vector was transfected into CHO-DG44 cells (Aprogen, Korea), and the cells were cultured in α-MEM(GibCo, USA), containing 10% dFBS (Gibco, USA) and 500 µg/ml G418 (geneticin; Sigma, USA). To optimize the expression of the KDR(ECD)-Fc chimeric protein, the cells were cultured in CHO-SFM2 medium (Gibco) in the presence of MTX (methotrexate, Sigma), while the MTX concentration was increased. As a result, it was confirmed that the protein was optimally expressed at 700 nM MTX.

The produced protein was purified using protein A affinity chromatography (protein A-Sepharose, GE healthcare) and size exclusion chromatography (Hiload superdex 200, GE healthcare) and stored in 10 mM phosphate buffer (pH 7.0) containing 150 mM NaCl. FIG. 3 shows the results of SDS-PAGE of KDR(ECD1-3)-Fc purified according to the above method.

Example 2

Preparation of Complete Human (naïve) Single Chain Antibody (ScFv) Phage Display Library Total RNA was obtained from five healthy bone-marrow donors using TRI reagents (Sigma), and based on the total RNA, mRNA was purified using an mRNA purification kit (oligotex mRNA preparation kit, Qiagen, USA). The mRNA was treated using an RT-PCR system (ThermoScript RT-PCR system, Gibco-BRL, USA) to obtain cDNA. To obtain a VH gene, each of a V gene fragment and a DJ fragment was amplified using the primers shown in Table 1, and each of the amplified DNA fragments was amplified by $2^{nd}$ PCR using primers (SEQ ID NOS: 29-61) having SfiI restriction enzyme sites at the 5' end and the 3' end.

TABLE 1

Primer sequence for amplifying VH and DJ gene fragments

| | | SEQ ID NO: |
|---|---|---|
| VH gene-forward | | |
| H05 | GARGTGCAGCTGGTGGAGTC | 29 |
| H06 | CAGSTGCAGCTGCAGGAGTC | 30 |
| H08 | CAGGTACAGCTGCAGCAGTC | 31 |
| H09 | CAGRTGCAGCTGGTGCAGTCTGGGG | 32 |
| H11 | GAGGTGCAGCTGGTGCAGTCTGGAGCA | 33 |
| H12 | CAGGTTCAGCTGGTGCAGTCTGGAG | 34 |
| H13 | CAGGTTCAGCTGGTGCAGTCTGGGG | 35 |
| H14 | CAGGTCCAGCTGGTACAGTCTGGGG | 36 |
| H15 | CAGGTCACCTTGAAGGAGTCTGGTCCTGT | 37 |
| H16 | CAGATCACCTTGAAGGAGTCTGGTCCTAC | 38 |
| H17 | CAGGTCACCTTGAGGGAGTCTGGTCCTGC | 39 |
| H25 | GAGGTGCAGCTGGTGGAGTCTGGGGGAGGTG | 40 |
| H32 | CAGGTGCAGCTACAGCAGTGGGGCG | 41 |
| VH gene-back | | |
| H210 | AATACACGGCCGTGTCCTCAGATC | 42 |
| H210L | AATACACGGCCGTGTCCTCAGATCTCAGGCTGCTCAGCTCCATGTAGGCTGAG | 43 |
| H211 | AGCTCCATGTAGGCTGTGTCT | 44 |
| H212 | AGCTCCATGTAGGCTGTGCTCATAGACC | 45 |
| H213 | AGCTCCATGTAGGCTGTGCTTGTGACA | 46 |
| H214 | AGCTCCATGTAGGCTGTGCTTATGGAG | 47 |
| H220 | AAGGACCACCTGCTTTTGGAGG | 48 |
| H230 | AATACACGGCCGTGTCCTCGGCTCTCAGACTGTTCATT | 49 |
| H240 | AATACACGGCCTGTCCACGGCGG | 50 |
| H250 | AATACATGGCGGTGTCCGAGGCCT | 51 |
| DJ gene-forward | | |
| CDR3-1 | GATCTGAGGACACGGCCGTGTATTACTGT | 52 |
| CDR3-2 | CCTCCAAAAGCCAGGTGGTCCTT | 53 |
| CDR3-3 | GAGCCGAGGACACGGCCGTGTATTACTGT | 54 |
| CDR3-4 | CCGCCGTGGACACGGCCGTGTATTACTGT | 55 |
| CDR3-5 | AGGCCTCGGACACCGCCATGTATTACTGT | 56 |
| DJ gene-back | | |
| JH-U1 | I CTGAGGAGACGGTGACC | 57 |
| V-DJ fusion | | |
| H48SfiI-for | GCGATGGCCCAGCCGGCCATGGCCCAGRTGCAGCTGGTRSAGTC | 58 |
| H49SfiI-for | GCGATGGCCCAGCCGGCCATGGCCCAGRTCACCTTGARGGAGTC | 59 |
| H50SfiI-for | GCGATGGCCCAGCCGGCCATGGCCCAGGTRCAGCTRCAGSAGT | 60 |
| H47SfiI-back | GGAATTCGGCCCCCGAGGCCTGARGAGACRGTGACC | 61 | cf.) R: A or G; S: C or G

To obtain a VL gene, $1^{st}$ PCR was performed using each of primers (Table 2) for lambda gene amplification and primers (Table 3) for kappa gene amplification, and each of the amplified fragments was subjected to 2nd PCR using primers (lambda: SEQ ID NOS. 76-81, and kappa: SEQ ID NOS. 106-108) having a BstXI digestion site at the 5' end and the 3' end.

TABLE 2

Primer sequence for amplifying Lambda gene fragment

| | | SEQ ID NO: |
|---|---|---|
| Vγ forward | | |
| L01 | CAGYCTGTGCTGACTCAG | 62 |
| L03 | CAGCCTGTGCTGACTCAAT | 63 |
| L06 | TCCTATGAGCTGACWCAG | 64 |
| L15 | CAGYCTGTGCTGACTCAGCCGT | 65 |
| L20 | CAGTCTGTGCTGACGCAGCCG | 66 |
| L23 | CAGTCTGCCCTGACTCAGCCTC | 67 |
| L24 | CAGTCTGCCCTGACTCAGCCTG | 68 |
| L25 | CAGRCTGTGGTGACYCAGGAGCCCTCAC | 69 |
| L26 | CAGRCTGTGGTGACYCAGGAGCCATCGT | 70 |
| L28 | TCCTATGAGCTGACWCAGCCACT | 71 |
| L34B | AATTTTATGCTGACTCAGCCC | 72 |
| Vγ back | | |
| L35 | CCTCCTCCACCTAGGACGGTGACCTTGGTCCCAGTT | 73 |
| L36 | CCTCCTCCACCTAGGACGGTCAGCTTGGTCCCTCCG | 74 |
| L37 | CCTCCTCCACCGAGGGCGGTCAGCTGGGTGCCTCCT | 75 |
| Vγ 2nd PCR (BstXI) | | |
| L34BstXI-for | GGTGGATCCAGCGGTGTGGGTTCCAATTTTATGCTGACTCAGCCC | 76 |
| L40BStXI-for | GGTGGATCCAGCGGTGTGGGTTCCCAGYCTGTGCTGACTCAGCC | 77 |
| L41BstXI-for | GGTGGATCCAGCGGTGTGGGTTCCCAGCCTGTGCTGACTCAATC | 78 |
| L42BstXI-for | GGTGGATCCAGCGGTGTGGGTTCCCAGTCTGCCCTGACTCAGCC | 79 |
| L43BstXI-for | GGTGGATCCAGCGGTGTGGGTTCCCAGRCTGTGGTGACYCAGGA | 80 |
| L44BstXI-for | GGTGGATCCAGCGGTGTGGGTTCCTCCTATGAGCTGACWCAG | 81 |
| L38BstXI-back | GAATTCCACGAGGCTGGCTCCTCCACCKAGGRCGGT | 82 | cf) K: G or T; R: A or G; Y: T or C; W: A or T

TABLE 3

Primer sequence for amplifying Kappa gene fragment

| | | SEQ ID NO: |
|---|---|---|
| Vκ forward | | |
| K12 | GACATCCAGATGACCCAGTCTCCATCCTCCC | 83 |
| K13 | GACATCCAGATGACCCAGTCTCCATCCTCA | 84 |
| K14 | GACATCCAGATGACCCAGTCTCCATCTTCYG | 85 |
| K15 | GACATCCAGATGACCCAGTCTCCTTCCA | 86 |
| K16 | AACATCCAGATGACCCAGTCTCCATCTGCCA | 87 |
| K17 | AACATCCAGATGACCCAGTCTCCATCCTT | 88 |
| K18 | GCCATCCAGTTGACCCAGTCTCCAT | 89 |
| K19 | GCCATCCGGATGACCCAGTCTCCATTCTCC | 90 |
| K20 | GTCATCTGGATGACCCAGTCTCCATCCTTA | 91 |
| K21 | GATATTGTGATGACCCAGACTCCACTCTCTCTGT | 92 |
| K22 | GATATTGTGATGACCCAGACTCCACTCTCCCTGC | 93 |
| K23 | GATATTGTGATGACCCAGACTCCACTCTCCTCA | 94 |
| K24 | GATRTTGTGATGACTCAGTCTCCACTCTC | 95 |
| K25 | GAAATTGTGTTGACRCAGTCTCCAG | 96 |
| K27 | GACATCGTGATGACCCAGTCTCCAG | 97 |
| VKA1 | GATGTTGTGATGACTCAGTCTCCACTCTCCCTGCCGTCACCCTTGGAC | 98 |
| VK10 | GAAATTGTGCTGACTCAGTCTCCAGACTTT | 99 |
| VK30 | GACATCCAGATGACCCAGTCTCCATCCTCCCTGTCTGCATCTGTAGGAG | 100 |
| Vκ back | | |
| K28 | TCCTCCACGTTTGATTTCCACCTTGGTCCCTTG | 101 |
| K29 | TCCTCCACGTTTGATCTCCAGCTTGGTCCCC | 102 |
| K30 | TCCTCCACGTTTGATATCCACTTTGGTCCCAG | 103 |
| K31 | TCCTCCACGTTTGATCTCCACCTTGGTCCCTCC | 104 |
| K32 | TCCTCCACGTTTAATCTCCAGTCGTGTCCCT | 105 |
| Vκ BstXI | | |
| K33BstXI-for | GGTGGATCCAGCGGTGTGGGTTCCGACATCCAGATGACCCAGTCTCC | 106 |
| K34BstXI-for | GGTGGATCCAGCGGTGTGGGTTCCGATATTGTGATGACCCAGWCTCC | 107 |
| K36BstXI-back | GAATTCCACGAGGCTGGCTCCTCCACGTTTGATHTCCA | 108 | cf) H: A, C or T; W: A or T

To introduce the VH gene fragment and the VL gene fragment into a phagemid vector, a pAK100 vector (Krebber, A. et al., *J. Immunol. Method.*, 201:35, 1997) was used. To introduce the VL gene fragment, three BstXI domains (236, 365 and 488) present in the lac repressor gene (laI) of the pAK100 vector were mutated using the Quikchange site-specific mutagenesis kit (Stratagene, USA). Using the modified pAK100 vector, to prepare a backbone vector for the construction of the ScFv library, the heavy chain V gene, amplified using the H05 primer (SEQ ID NO: 29) and the H230 primer (SEQ ID NO: 49), and the DJ gene fragment, amplified using the CDR3-3 primer (SEQ ID NO: 54) and the JH-U1 primer (SEQ ID NO: 57), were subjected to $2^{nd}$ PCR with H48SfiI (SEQ ID NO: 58)/H47SfiI (SEQ ID NO: 61), and the resulting heavy chain variable region was digested with SfiI and ligated into the modified pAK100 vector digested with the same enzyme. To introduce a light chain and a linker, the heavy chain region was amplified using primers (forward: SEQ ID NO: 109; and backward: SEQ ID NO: 110), and the light chain sequence of the human 4-1BB antibody (LB506) (Korean Patent Publication 2000-0034847) was amplified using each of primers (forward: SEQ ID NO: 111; and backward: SEQ ID NO: 112). The amplified fragments were inserted into the modified pAK100 vector having the heavy chain variable domain introduced therein, using XbaI/EcoRI, thus preparing an antibody library backbone vector.

SEQ ID NO: 109:
5'-CGAATTTCTAGATAACGA-3'

SEQ ID NO: 110:
5'-CCTCCGCCACTACCTCCTCCTCCGAGGCCCCCGAGGCCTGA-3'

SEQ ID NO: 111:
5'-GGTAGTGGCGGAGGAGGCTCCGGTGGA TCCAGCGGTGTGG
GTTCCGATATTGTG-3'

SEQ ID NO: 112:
5'-CTCGAATTCCCACGAGGCTGGCTCCTCCACGTTTGATTTC-3'

In order to introduce light chain variable regions, each of amplified light chain (κ, λ) variable regions was digested with BstXI and inserted into the antibody library backbone vector. The resulting plasmid was digested with a SfiI restriction enzyme and ligated with a heavy chain variable region-amplified PCR fragment previously digested with SfiI. The ligated plasmid was transfected into ElectroTen-Blue competent cells (Stratagene, USA). As a result, a ScFv phage library having a diversity of about $10^{11}$ was collected from the colony.

Example 3

Biopanning

The library stock constructed in Example 2 was grown to the log phase and rescued with the M13K07 helper phage (GE healthcare, USA). The resulting library was amplified in 2×YT medium (2×YT/C/K; containing 34 μg/ml of chloramphenicol and 70 μg/ml of kanamycin and supplemented with 1 mM IPTG) at 30° C. overnight. Phage stock was precipitated in 20% PEG6000/2.5M NaCl and resuspended in PBS. Resuspended phage stock was incubated in 2% skimmed milk/PBS solution containing 500 μg/ml of a human Fc protein at 37° C. for 1 hour in order to remove phages showing anti-human Fc.

The KDR (human VEGFR-2) used as an antigen was KDR (ECD1-3)-Fc comprising IgG-like domains 1, 2 and 3 of the extracellular domain of KDR. The KDR(ECD1-3)-Fc stable cell line prepared in Example 1 was cultured, and KDR (ECD1-3)-Fc was purified from the cultured cell line.

Maxisorb Star tubes (Nunc, Denmark) coated with KDR (ECD1-3)-Fc (10 μg/ml) were first blocked with 2% skimmed milk/PBS at room temperature for 2 hours, and then inoculated with $5.4 \times 10^{12}$ pfu of the phage stock at room temperature for 1 hour.

The tubes were washed 10 times with PBST (PBS containing 0.1% Tween 20), and then washed 10 times with PBS. The bound phage was eluted with 1 ml of 100 mM fresh triethylamine solution at room temperature for 10 minutes. The eluted phage was left to stand together with 10 ml of mid-log-phase XL1-Blue cells at 37° C. for 30 minutes, and then shake-cultured for 30 minutes. Then, the infected XL1-Blue cells were cultured in a 1% glucose-containing 2×YT/C plate at 30° C. overnight. Following the first panning, the second and third panning processes were performed by coating KDR (ECD1-3)-Fc into a 96-well plate (Nunc, USA) instead of the maxisorp tube. After the third panning was performed, the KDR neutralizing ability of the obtained phage was analyzed through VEGF competition assays.

Figure 4:
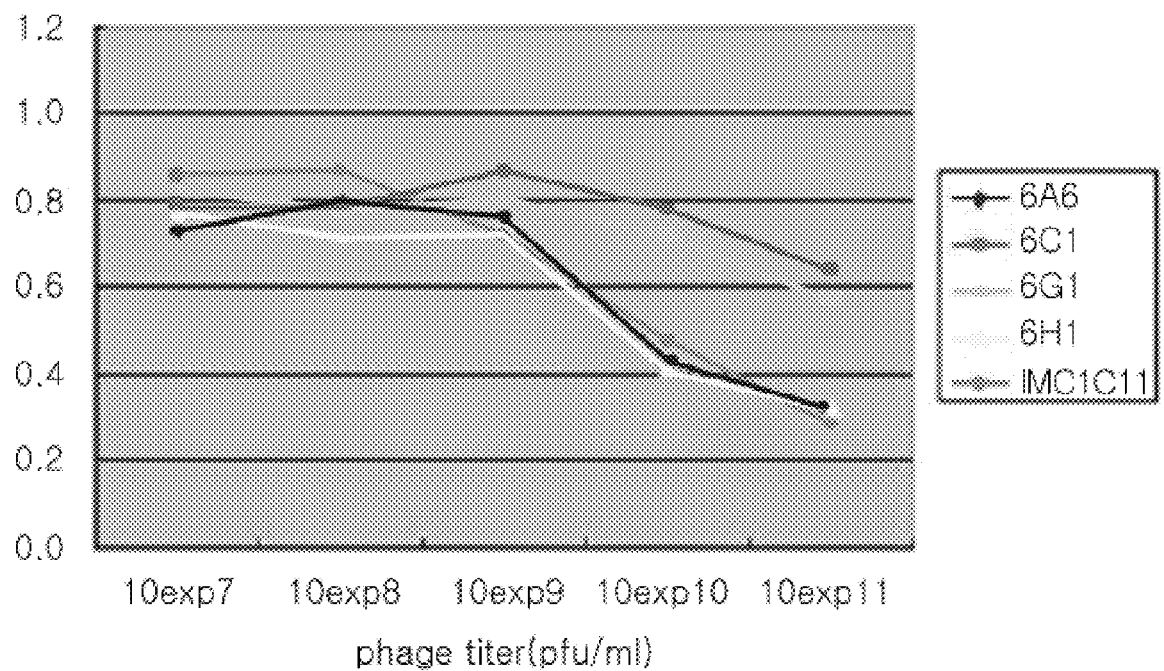
FIG. 4 shows the results of VEGF competition assays for anti-KDR phage and anti-KDR-SvFc according to the present invention.

For VEGF competition assays, a microplate coated with 200 ng of VEGF165 (R&D system) overnight was allowed to react with 2% skimmed milk/PBS at 37° C. for 2 hours. The microplate was washed with PBS, and then a mixture, obtained by reacting 10 ng of KDR (ECD1-3)-Fc with various amounts of phage at room temperature for 1 hour, was placed in each well of the plate and allowed to react at room temperature for 2 hours. The reaction solution was washed with PBS, allowed to react with a rabbit anti-KDR antibody (Reliatech, Germany) at 37° C. for 1 hour, and allowed to react with an HRP (horse radish peroxidase)-conjugated goat anti-rabbit antibody (Abcam, UK) at 37° C. for 1 hour. After the completion of the reaction, each well was color-developed with a TMB solution (Sigma), and then measured for absorbance at 450 nm (FIG. 4).

As a result, it was seen that 6A6, 6H1, 6G1 and 6C1 could all inhibit the binding of VEGF to KDR, and among them, 6A6 and 6H1 showed the highest ability to neutralize VEGF. Also, 6A6 and 6H1 were shown to have a binding affinity similar to that of a reconstructed 1C11 (hereinafter referred to as 1C11) phage obtained in Example 4. The DNA sequences, amino acid sequences and CDR sequences of 6A6 (TTAC-0001) ScFv are shown in FIG. 5.

Also, the base sequences and amino acid sequences of 6A6 (TTAC-0001) ScFv were expressed as heavy chain CDR 1 (SEQ ID NO: 113 and SEQ ID NO: 114), heavy chain CDR 2 (SEQ ID NO: 115 and SEQ ID NO: 116), heavy chain CDR 3 (SEQ ID NO: 117 and SEQ ID NO: 118), light chain CDR 1 (SEQ ID NO: 119 and SEQ ID NO: 120), light chain CDR 2 (SEQ ID NO: 121 and SEQ ID NO: 122), light chain CDR 3 (SEQ ID NO: 123 and SEQ ID NO: 124), heavy chain variable regions (SEQ ID NO: 125 and SEQ ID NO: 20), light chain variable regions (SEQ ID NO: 126 and SEQ ID NO: 1), IgG heavy chain regions (SEQ ID NO: 127 and SEQ ID NO: 128), and IgG light chain regions (SEQ ID NO: 129 and SEQ ID NO: 130).

Example 4

Construction of Reconstructed
IMC-1121(rIMC-1121) and IMC-1C11(rIMC-1C11)
Phage Vectors In order to obtain IMC-1C11 ScFv (PCT/US2001/10504) and IMC-1121 ScFv (PCT/US2002/006762) phage particles (Imclone) to be used as positive control groups, the ScFv region of each antibody was cloned into the pAK vector.

For IMC-1C11, a light chain variable gene was cloned using, as a template, a pTA-d9-07 clone (LG Life Sciences) obtained from a mouse naïve antibody library (LG Life Sciences). The clone was amplified by PCR using the LR and LF primers shown in Table 4, and the amplified light chain variable gene was digested with BstXI and ligated into a library backbone vector pretreated with BstXI. A heavy chain variable gene was amplified by PCR using a pTA-A5N2-10 clone (LG Life Sciences) as a template with the primers shown in Table 4. After each of the PCR reactions was performed using each of the primer pairs HF1-RI(A), HF2-HR2 (B), HF3-HR3(C) and HF4-HR4(D), and each of the amplified fragments was amplified by overlap PCR using A-B (HF1-HR2 primer set) and C-D (HF3-HR4 primer pair), and then amplified by overlap PCR using A-B-C-D (HF1-HR4 primer pair). Then, each of the amplified fragments was treated with SfiI and ligated with the 1C11 light chain gene-containing library backbone vector treated with SfiI. Table 4 shows the PelB signal sequence and DNA sequence to amber (TGA) codon of the phage vector (pAK-r1c11).

TABLE 4

| Name | Sequence | SEQ ID NO: |
|---|---|---|
| pTA-d9_07 light chain | GACATTGTTC TCATCCAGTC TCCAGCAATC ATGTCTGCAT CTCCAGGGGA GAAGGTCACC ATAACCTGCA GTGCCAGCTC AAGTGTAAGT TACATGCACT GGTTCCAGCA GAAGCCAGGC ACTTCTCCCA AACTCTGGAT TTATAGCACA TCCAACCTGG CTTCTGGAGT CCCTGCTCGC TTCAGTGGCA GTGGATCTGG GACCTCTTAC TCTCTCACAA TCAGCCGAAT GGAGGCTGAA GATGCTGCCA CTTATTACTG CCAGCAAAGG AGTAGTTACC CATTCACGTT CGGCTCGGGG ACAAAGTTGG AAATAAAA | 131 |
| pTA-A5N²-10 heavy chain | CAGGTTCAGC TCCAGCAGTC TGGGGCAGAG CTTGTGAGGT CAGGGGCCTC AGTCAAGTTG TCCTGCACAG CTTCTGGCTT CAACATTAAA GACTACTATA TGCACTGGGT GAAGCAGAGG CCTGAACAGG GCCTGGAGTG GATTGGATGG ATTGATCCTG CGAATGGTAA TACTAAATATGACCCGAAGT TCCAGGGCAA GGCCACTATA ACAGCAGACA CATCCTCCAA CACAGCCTAC CTGCAGCTCA GCAGCCTGAC ATCTGAGGAC ACTGCCGTCT ATTACTGTGC TAGATGGGAC TGGTACTTCG ATGTCTGGGG CGCAGGGACC ACGGTCACCG TTTCC | 132 |
| LF | CTGCAGAACC AGCGGTGTGG GTTCCGACAT CGAGCTCACT CAGTCTCCAT G | 133 |
| LR | CTGCAGAACC ACGAGGCTGG CTCCTCCACG TTTTATTTCC AGCTTGGTCC CCG | 134 |
| HF1 | CGGCCCAGCC GGCCATGGCC CAGGTCAAGC TGCAGCAGTC TGGGGCAGAG CTTGTGGGGT CAGGGGCC | 135 |
| HF2 | GGCTTCAACA TTAAAGACTT CTATATGCA | 136 |
| HF3 | GATTATGCCC CGAAGTTCCA GGGCAAGGCC ACCATGACTG CAGACTCATC CTCCA | 137 |
| HF4 | TACTGTAATG CATACTATGG TGACTACGAA GGCTACTGGG GCCAA | 138 |
| HR1 | GTCTTTAATG TTGAAGCCAG AAGTTGTGCA G | 139 |
| HR2 | ACTTCGGGGC ATAATCAGAA TCACCATTCT CAGGATCAAT CCATCCAATC | 140 |
| HR3 | GTATGCATTA CAGTAATAG | 141 |

TABLE 4-continued

| | LR and LF primer | |
|---|---|---|
| Name | Sequence | SEQ ID NO: |
| HR4 | CCGAGGCCCC CGAGGCCTGA GGAGACGGTG ACCGTGGTCC CTTGGCCCCA GTAGCCTTCG TA | 142 |
| r1C11-ScFv DNA | ATGAAATACC TATTGCCTAC GGCAGCCGCT GGATTGTTAT TACTCGCGGC CCAGCCGGCC ATGGCCCAGG TCAAGCTGCA GCAGTCTGGG GCAGAGCTTG TGGGGTCAGG GGCCTCAGTC AAATTGTCCT GCACAACTTC TGGCTTCAAC ATTAAAGACT TCTATATGCA CTGGGTGAAG CAGAGGCCTG AACAGGGCCT GGAGTGGATT GGATGGATTG TCCTGAGAA TGGTGATTCT GATTATGCCC CGAAGTTCCA GGGCAAGGCC ACCATGACTG CAGACTCATC CTCCAACACA GCCTACCTGC AGCTCAGCAG CCTGACATCT GAGGACACTG CCGTCTATTA CTGTAATGCA TACTATGGTG ACTACGAAGG CTACTGGGGC CAAGGGACCA CGGTCACCGT CTCCTCAGGC CTCGGGGCC TCGGAGGAGG AGGTAGTGGC GGAGGAGGCT CCGGTGGATC CAGCGGTGTG GGTTCCGACA TCGAGCTCAC TCAGTCTCCA GCAATCATGT CTGCATCTCC AGGGGAGAAG GTCACCATAA CCTGCAGTGC CAGCTCAAGT GTAAGTTACA TGCACTGGTT CCAGCAGAAG CCAGGCACTT CTCCCAAACT CTGGATTTAT AGCACATCCA ACCTGGATTA TGGAGTCCCT GCTCGCTTCA GTGGCAGTGG ATCTGGGACC TCTTACTCTC TCACAATCAG CCGAATGGAG GCTGAAGATG CTGCCACTTA TTACTGCCAG CAAAGGAGTA GTTACCCATT CACGTTCGGC TCGGGGACCA AGCTGGAAAT AAAACGTGGA GGAGCCAGCC TCGTGGAATT CGAGCAGAAG CTGATCTCTG AGGAAGACCT GTAG | 143 |

In order to obtain IMC-1121, 6G1 was used as a template to clone a light chain variable region. The 6G1 template was amplified by PCR using the primer pairs LF-KR1(A), LF1-LR2(B), LF2-LR3(C) and LF3-LR4(D), was amplified by overlap PCR using A-B (LF-LR2 primer set) and C-D (LF2-LR primer pair), and was then amplified by overlap PCR using A-B-C-D (LF-LR primer pair). The obtained PCR fragment was treated with BstXI and inserted into the library backbone vector (reconstructed IMC-1121; hereinafter referred to as IMC-1121). The primers used herein are shown in Table 5.

For the heavy chain variable region, the YGKL-136 clone having a sequence closest to IMC-1121 among the clone sequences obtained from the human na Ave scFv library (Example 2) was used as a template. The YGKL-136 clone was amplified by PCR using each of the primer pairs HF-HR1 (A), HF1-HR2(B) and HF2-HR(C), was subjected to A+B overlap PCR (HF-HR2 primer pair), and was then subjected to A+B and C overlap PCR (HF-HR primer pair). The produced PCR fragment was treated with SfiI and ligated into a light chain-containing library backbone vector.

TABLE 5

| LF and HF primer for cloning light chain variable region | | |
|---|---|---|
| Name | Sequence | SEQ ID NO: |
| YGKL-136 heavy chain | GAGGTGCAGC TGGTGGAGTC TGGGGGAGGC CTGGTCAAGC CTGGGGGGTC CCTGAGACTC TCCTGTGCAG CCTCTGGATT | 144 |

TABLE 5-continued

LF and HF primer for cloning light chain variable region

| Name | Sequence | SEQ ID NO: |
|---|---|---|
| (template) | CACCTTCAGT AGCTATAGCA TGAACTGGGT CCGCCAGGCT CCAGGGAAGG GGCTGGAGTG GGTCTCATCC ATTAGTAGTA GTAGTAGTTA CATACACTAC GCAGACTCAG TGAAGGGCCG ATTCACCATC TCCAGAGACA ACGCCAAGAA CTCACTGTAT CTGCAAATGA ACAGTCTGAG AGCCGAGGAC ACGGCCGTGT ATTACTGTGC GAGAGTCACA GATGCTTTTG ATATCTGGGG CCCCGGAACC CTGGTCACCG TCTCCTCA | |
| 6G1 light chain (template) | GACATCCAGA TGACCCAGTC TCCATCTTCC GTGTCTGCAT CTGTAGGAGA CAGAGTCACC ATCACTTGTC GGGCGAGTCA GGGTATTAGC AGCTATTTAG CTGGTATCA GCAGAAACCA GGGAAAGCCC CTAAGCTCCT GATCTATGCT GCATCCAATT TGCAAACAGG GGTCCCGCCA AGGTTCAGCG GCAGTGGATC CGGGACAAGT TTCACTCTCA CCCTCAATAA TGTGCAGCCT GAAGATTCTG CAACTTACTA TTGTCAACAG GCTGACAGTT TCCCTCTTTC GGCGGAGGGA CCAAAGTGGA AATCAAACGT GAGGAGCC | 145 |
| LF primer | CCCCAGCGGT GTGGGTTCCG ACA | 146 |
| LR1 primer | TGGTGACTCT GTCTCCTATA GATGCAGACA CGGATGAT | 147 |
| LF1 primer | TCTATAGGAG ACAGAGTCAC CA | 148 |
| LR2 primer | TACCAGCCTA ACCAGTTGTC AATACCCTGA CTCGCCCG | 149 |
| LF2 primer | TTGACAACTG GTTAGGCTGG TATCAGCAGA AACCAGGG AAA | 150 |
| LR3 primer | ACCTTGATGG GACCCCTGTG TCCAAATTGG ATGCATCATA GATCAGGAGC TT | 151 |
| LR primer | CCCCACGAGG CTGGCTCCTC CA | 152 |
| HF primer | CCGGCCCAGC CGGCCATGGC CGAGGTGCAG CTGGTGCAGT CTGGGGGAGG CCTGGTCA | 153 |
| HF1 primer | GTAGTAGTAG TAGTTACATA TACTACGCAG ACTCAGTGA | 154 |
| HF2 primer | TTACTGTGCG AGAGTCACAG ATGCTTTTGA TATCTGGGGC CAAGGGACAA | 155 |
| HR1 primer | TCACTGAGTC TGCGTAGTAT ATGTAACTAC TACTACT | 156 |
| HR2 primer | CTGTGACTCT CGCACAGTAA TACA | 157 |
| HR primer | CCGGCCCCCG AGGCCTGAGG AGACGGTGAC CATTGTCCCT TGGCCCCAG | 158 |
| r1121-ScFv DNA | ATGAAATACC TATTGCCTAC GGCAGCCGCT GGATTGTTAT TACTCGCGGC CCAGCCGGCC ATGGCCGAGG TGCAGCTGGT GCAGTCTGGG GGAGGCCTGG TCAAGCCTGG GGGGTCCCTG | 159 |

TABLE 5-continued

LF and HF primer for cloning light chain variable region

| Name | Sequence | SEQ ID NO: |
|---|---|---|
| | AGACTCTCCT GTGCAGCCTC TGGATTCACC TTCAGTAGCT | |
| | ATAGCATGAA CTGGGTCCGC CAGGCTCCAG GGAAGGGGCT | |
| | GGAGTGGGTC TCATCCATTA GTAGTAGTAG TAGTTACATA | |
| | TACTACGCAG ACTCAGTGAA GGGCCGATTC ACCATCTCCA | |
| | GAGACAACGC CAAGAACTCA CTGTATCTGC AAATGAACAG | |
| | TCTGAGAGCC GAGGACACGG CCGTGTATTA CTGTGCGAGA | |
| | GTCACAGATG CTTTTGATAT CTGGGGCCAA GGGACAATGG | |
| | TCACCGTCTC CTCAGGCCTC GGGGGCCTCG GAGGAGGAGG | |
| | TAGTGGCGGA GGAGGCTCCG GTGGATCCAG CGGTGTGGGT | |
| | TCCGACATCC AGATGACCCA GTCTCCATCT TCCGTGTCTG | |
| | CATCTATAGG AGACAGAGTC ACCATCACTT GTCGGGCGAG | |
| | TCAGGGTATT GACAACTGGT TAGGCTGGTA TCAGCAGAAA | |
| | CCTGGGAAAG CCCCTAAACT CCTGATCTAC GATGCATCCA | |
| | ATTTGGACAC AGGGGTCCCA TCAAGGTTCA GTGGAAGTGG | |
| | ATCTGGGACA TATTTTACTC TCACCATCAG TAGCCTGCAA | |
| | GCTGAAGATT TTGCAGTTTA TTTCTGTCAA CAGGCTAAAG | |
| | CTTTTCCTCC CACTTTCGGC GGAGGGACCA AGGTGGACAT | |
| | CAAACGTGGA GGAGCCAGCC TCGTGGAATT CGAGCAGAAG | |
| | CTGATCTCTG AGGAAGACCT GTGA | |

Example 5

Production and Purification of Soluble ScFv

To prepare soluble 6A6 ScFv, pAK-6A6, having a pelB sequence and an ScFv sequence, was digested with EcoRI and XbaI to obtain a fragment, having the pelB sequence and the ScFv sequence. The fragment was inserted into the pET21b vector (Novagen, USA) using the same restriction enzymes. To add an myc tag to the vector inserted with the fragment having the pelB sequence and the ScFv sequence, the pET21b vector, inserted with the pelB sequence and the ScFv sequence, as a template, was amplified by PCR using primers (mycFor: SEQ ID NO: 160, and mycRev: SEQ ID NO: 161), and the PCR fragment was ligatged into the vector having the pelB sequence and the ScFv sequence, using EcoRI and XhoI, thus constructing pET21b-KDR 6A6.

```
                                    SEQ ID NO: 160:
5'-GAGCCAGCCTCGTGGAATTCGAACAAAAA-3'

SEQ ID NO: 161:
5'-TGCTCGAGAT TCAGATCCTC TTCTGAGATG

AGTTTTTGTT GAATTCCACG AGGCT-3'
```

For kinetic measurement, a V5 tag sequence (GKPIPN-PLLGLDST) was inserted in an XhoI site downstream of the myc tag in the following manner. The resulting sequence was amplified by PCR using primers (V5-For: SEQ ID NO: 162, and V5-Rev: SEQ ID NO: 163) amplifying the EcoRI and V5 tag sequence-containing XhoI digestion sites of the pET21b-KDR 6A6, and the amplified fragment was digested with EcoRI and XhoI and ligated into the pET21b-KDR 6A6 digested with the same restriction enzymes, thus constructing pETV-KDR 6A6. The constructed pETV-KDR 6A6 was transformed into *E. coli* BL21(DE3).

```
                                    SEQ ID NO: 162:
5'-CCAGCCTCGTGGAATTC GAAC-3'

SEQ ID NO: 163:
5'-CCGCTCGAG GGTGGAGTC CAGACCTAATAG

AGGGTT TGGGATCGG CTTTCCATTCAGATC CTCTTCTGA-3'
```

The *E. coli* BL21(DE3) cells transformed with the pETV-KDR 6A6 were cultured to express the soluble ScFv protein and centrifuged, and a periplasmic fraction was collected from the cells using 50 mM Tris (pH 8.0) solution containing 20% sucrose and 200 μg/ml of a lysozyme and protease inhibitor cocktail (Roche, Swiss). The obtained fraction was purified using Ni-NTI affinity chromatography (Hisprep, GE healthcare, USA) and ion exchange chromatography (Q-sepharose, SP-sepharose, GE healthcare, USA), thus obtaining an ScFv protein.

Figure 6:
FIG. 6 shows SDS-PAGE results for purified 6A6 ScFv.

For 6A6, the Hisprep column was equilibrated using a solution containing 20 mM imidazole, 0.4M NaCl and 1×PBS, and the periplasmic fraction was placed in the column and eluted with 300 mM imidazole-containing solution (300 mM imidazole, 0.4M NaCl/1×PBS). The eluted protein was dialyzed with 50 mM imidazole (pH 6.7) solution, and then eluted using cation exchange chromatography while increasing the concentration of NaCl to 0.5M. The eluted protein was concentrated (centriprep YM10, milipore, USA), and then dialyzed and stored in PBS solution. FIG. 6 shows the results of SDS-PAGE of the purified 6A6 ScFv.

Example 6

VEGF Competition Assays with VEGF

Figure 7:
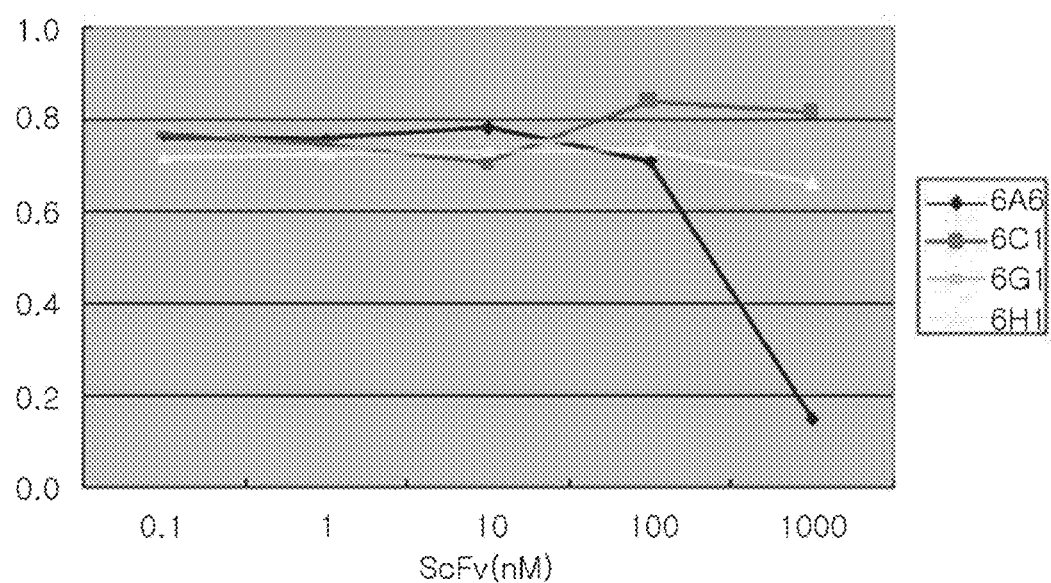
FIG. 7 shows the results of VEGF competition assays using anti-KDR-ScFv.

In order to examine whether the isolated ScFv can inhibit the binding of KDR to VEGF, competition assays were performed. For this purpose, 20 ng of VEGF165 was coated into a 96-well microtiter plate at room temperature overnight, and then allowed to react with 2% skimmed milk/PBS at 37° C. for 2 hours. After the completion of the reaction, the plate was washed with PBS, and then mixture solutions, obtained by allowing 100 ng of Fc-digested KDR(ECD1-3) to react with various amounts of ScFv at room temperature for 1 hour, were placed in the microtiter plate and allowed to react at room temperature for 2 hours. After the completion of the reaction, the plate was washed with PBS, and then an anti-KDR mouse antibody (5 μg/ml, Reliatech, Germany) was added thereto and allowed to react at 37° C. for 1 hour. Then, a 1:5000 dilution of an HRP-conjugated goat anti-mouse antibody (Abcam, UK) was added thereto and allowed to react for 1 hours, and then TMB solution was added thereto and allowed to react. Then, the cells in each well of the plate were measured for absorbance at 450 nm and 650 nm. FIG. 7 shows the results of VEGF competitive assays with the anti-KDR-ScFv purified in Example 5. As shown in FIG. 7, it can be seen that only 6A6-ScFv shows a potent ability to neutralize KDR.

Example 7

Epitope Mapping with Anti-KDR ScFv Antibody

In order to examine which anti-KDR ScFv antibodies bind to which domain of extracellular domains 1-3 of KDR, 3 μg/ml of each of the KDR(ECD1-2), KDR(ECD2-3) and KDR(ECD 1-3)-Fc prepared according to the method of Example 1 was coated into a 96-well plate by reaction at 37° C. for 2 hours. After the completion of the reaction, the plate was washed with PBS, and then the portion of the plate, which has not been coated with the KDR protein, was blocked with 2% skimmed milk/PBS. Then, the plate was washed again with PBS, and then 330 nM anti-KDR ScFv antibody was added thereto and allowed to react at 37° C. for 1 hour and 30 minutes. After the completion of the reaction, the plate was washed again with PBS, and then a 1:500 dilution of an HRP-conjugated rabbit anti-6×His antibody (Abcam, UK) was added thereto and allowed to react at 37° C. for 1 hour. Then, the cells in each well were color-developed with TMB solution and measured for absorbance at 450 nm.

Figure 8:
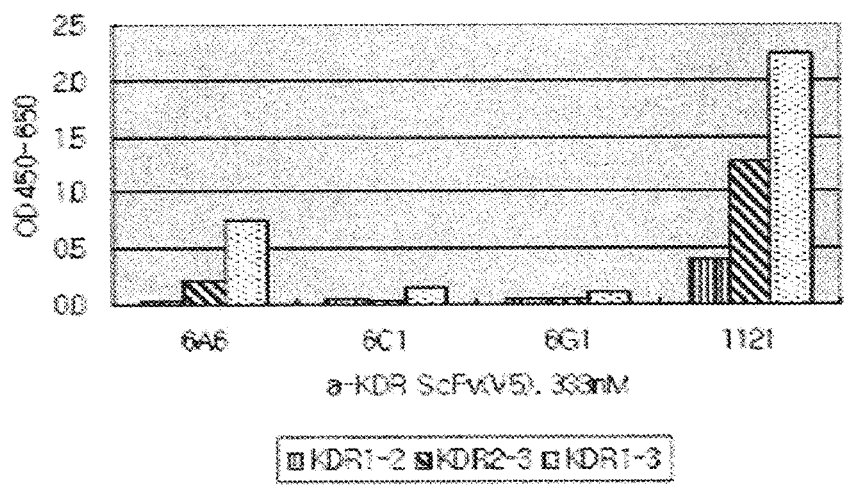
FIG. 8 shows the results of epitope mapping of anti-KDR-ScFv according to the present invention.

As a result, it could be seen that 6A6 was bound to the extracellular domain 3 of KDR in the same manner as IMC-1121 (FIG. 8). However, 6G1 and 6C1 were more strongly bound to the domain 1, even though the absorbance was low.

Example 8

Expression and Purification of IgG

Figure 9:
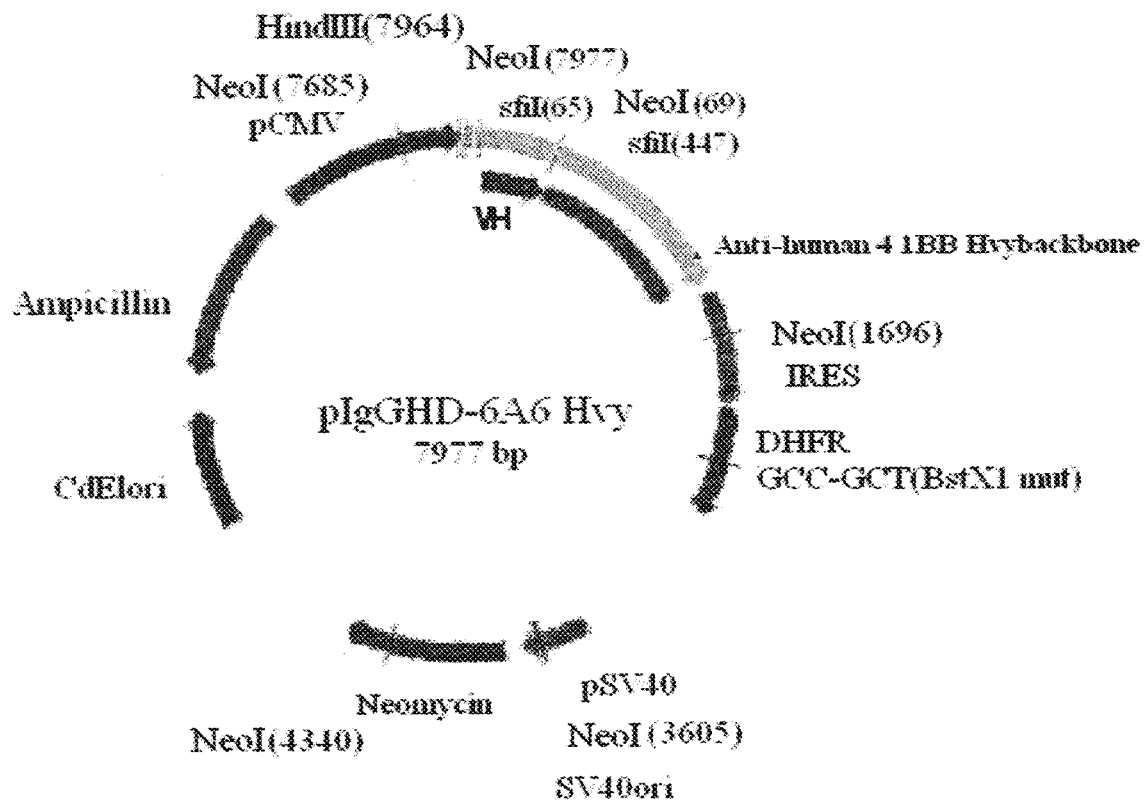
FIG. 9 shows a cleavage map of pIGHD-6A6Hvy that is a vector containing the invariable region and heavy chain region of 6A6 IgG.

For expression in the form of whole IgG, heavy chain and light chain expression vectors, each comprising a whole constant region, were prepared. For the heavy chain expression vector, a pIgGHD vector (Aprogen, Korea) having a heavy chain backbone of human 4-1 bb was treated with SfiI, and then ligated with a fragment, obtained by treating the heavy chain variable region of pAK-ScFv with SfiI, thus constructing an expression vector pIgGHD-6A6Hvy, comprising a whole constant region and a heavy chain region (FIG. 9).

Figure 10:
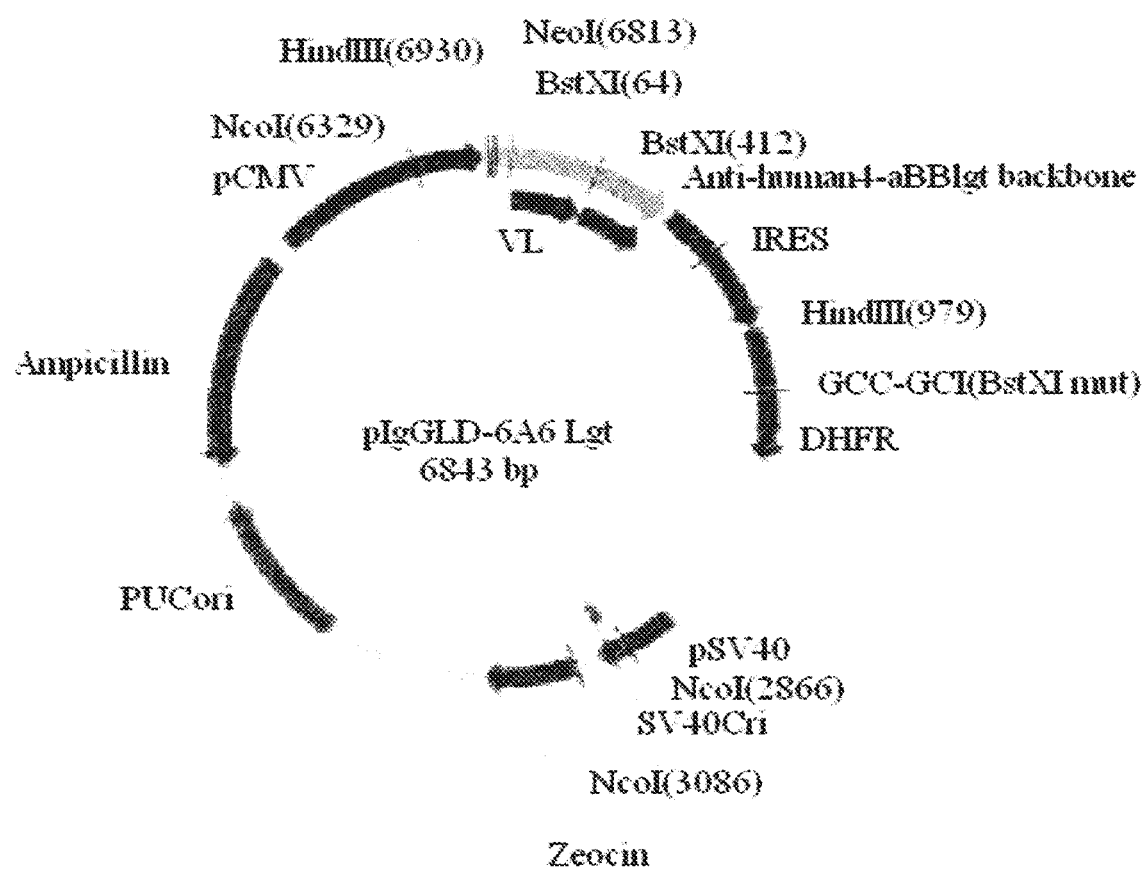
FIG. 10 shows a cleavage map of pIgGLD-6A6Lgt that is a vector containing the constant region and light chain region of IgG.

For the light chain expression vector, a pIgGLD vector (Aprogen, Korea) having a light chain backbone of human 4-1 bb was treated with BstXI, and then ligated with a fragment, obtained by treating the light chain variable region of pAK-ScFv with BstXI, thus constructing an expression vector pIgGLD-6A6Lgt, comprising a whole constant region and a light chain region (FIG. 10). In the case of IMC-1C11 and 1121, IgG expression vectors were constructed in the same manner as described above.

For the expression of IgG, the same amount of the light chain expression vector (pIgGHD-6A6Hvy for the 6A6 clone) and the heavy chain expression vector (pIgGLD-6A6Lgt for the 6A6 clone) were co-transfected into CHO DG44 cells (Aprogen, Korea). The co-transfected cells were cultured in α-MEM medium containing 10% dFBS and 500 μg/ml of G418, and then a clone having the highest protein expression level was selected, while MTX was added thereto at a concentration ranging from 10 nM to 700 nM.

Figure 11:
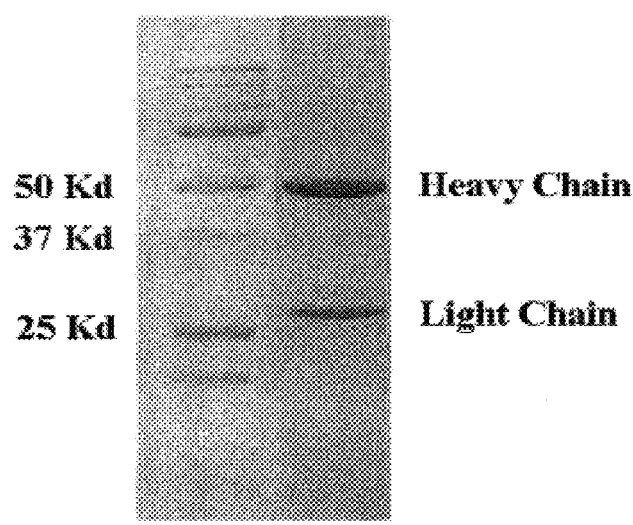
FIG. 11 shows the results of SDS-PAGE of purified 6A6 IgG.

For the expression of antibodies, the cells were cultured in CHO-SF2 medium, containing 700 nM MTX, at 37° C., and the culture was collected. 6A6-IgG was purified from the combined supernatant by affinity chromatography using a protein A column (GE healthcare, USA) according to the manufacturer's protocol. The supernatant was poured into the protein A column equilibrated with a solution containing 20 mM sodium phosphate (pH 7.0) and 100 mM NaCl and was washed with a solution containing 20 mM sodium phosphate (pH 7.0), 1 mM EDTA and 500 mM NaCl. Then, the protein was eluted with a 0.1 M glycine-HCl (pH 3.3) solution containing 100 mM NaCl. The eluted protein was neutralized with 1 M Tris. The eluted protein was mixed with 5 mM sodium phosphate buffer (pH 6.0) at a ratio of 1:1, and then poured into a prepacked SP-Sepharose column (GE healthcare) equilibrated with 5 mM sodium phosphate (pH 6.0) containing 50 mM NaCl. The protein bound to the column was eluted with a sodium phosphate buffer (pH 7.0) containing 50 mM NaCl and was poured into a prepacked Q-sepharose column (GE healthcare) equilibrated with an elution buffer, and unbound protein was collected. The collected protein was concentrated with 30 Kd vivaspin 20 (Sartorius) and dialyzed with PBS. FIG. 11 shows the results of SDS-PAGE of the 6A6 IgG protein purified according to the above-described method.

Example 9

Competition Assays of Anti-KDR IgG with Various VEGFs

Figure 12:
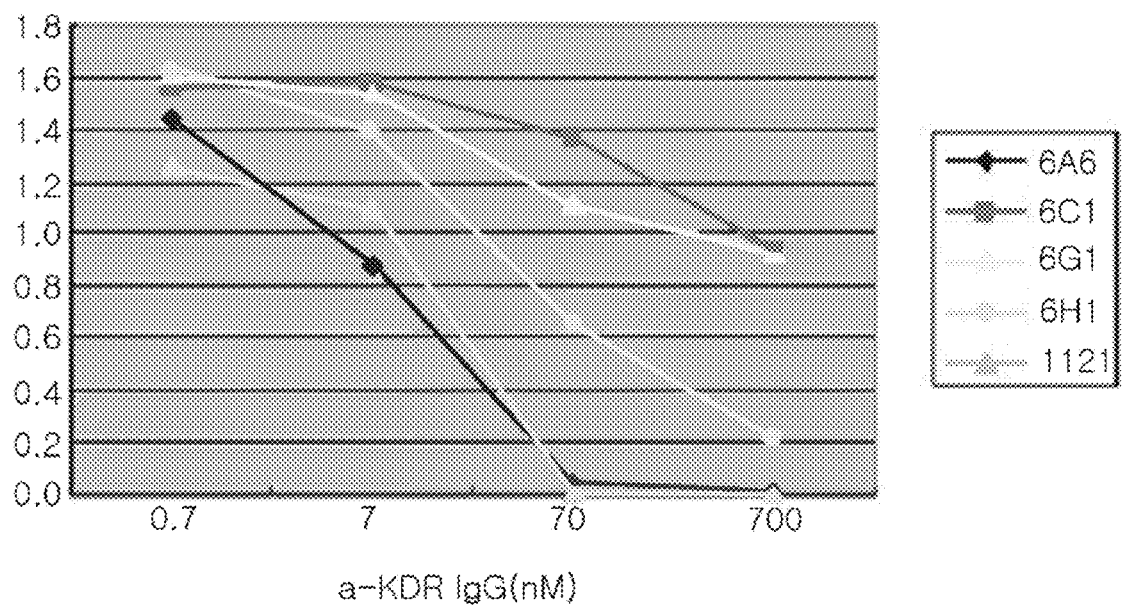
FIG. 12 shows the results of VEGF competition assays using anti-KDR 6A6 IgG.

Competition assays of anti-KDR IgG with VEGF were carried out in the same manner as the VEGF competition assays of KDR ScFv, conducted in Example 6 using VEGF165. As a result, 6A6 IgG among anti-IgGs showed the highest ability to neutralize KDR, similar to the results of the competition assays conducted with ScFv, and it showed KDR neutralizing ability similar to that of the IMC-1121 anti-KDR IgG reconstructed on the basis of the amino acid sequence (FIG. 12).

Figure 13:
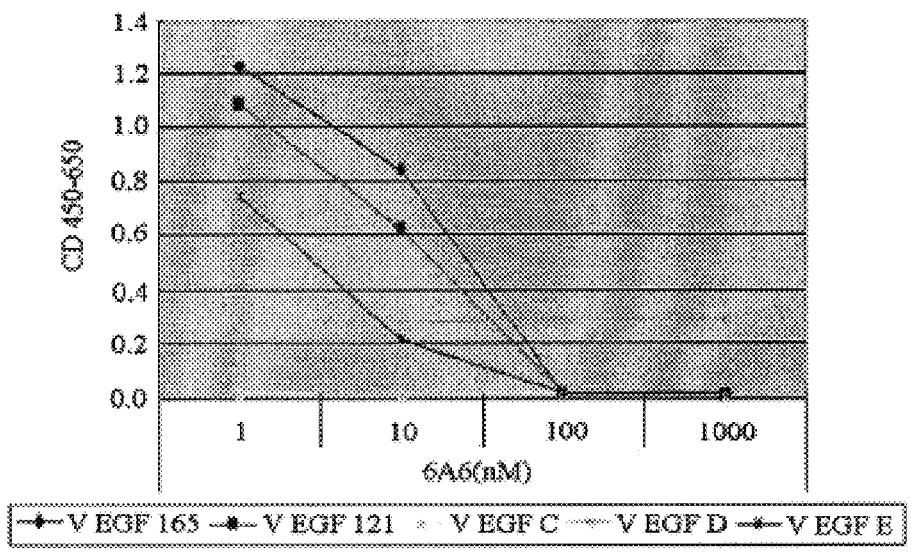
FIG. 13 shows the results of competition assays of anti-KDR 6A6 IgG with VEGF families.

Also, in order to examine the binding and competition of 6A6 IgG with isotypes and VEGF families other than VEGF165, 200 ng of each of VEGF121, VEGF165, VEGF-C, VEGF-D and VEGF-E was coated into a 96-well plate, and then competition assays were carried out in the same manner as in Example 6. As a result, 6A6 IgG showed VEGF neutralizing ability by binding to VEGF121, VEGF165 and VEGF-E, which belong to VEGF-A, and it did not bind to VEGF-C and VEGF-D (FIG. 13).

Example 10

Analysis of Binding Affinity of Anti-KDR ScFv and IgG

The binding affinity of the antibodies to KDR (VEGFR-2) was measured with BIAcore (GE healthcare). In the case of ScFv, KDR(ECD1-3)-Fc was immobilized onto a CM5 chip (GE healthcare, Sweden) according to the manufacturer's manual, and in the case of V5-tagged ScFv, a V5 antibody (Abchem, UK) was immobilized onto the chip. The V5-tagged ScFv was bound to the CM5 chip having the V5 antibody immobilized thereon, and then Fc-free KDR (ECD1-3) was allowed to run on the chip surface, thus obtaining sensorgrams. In the case of IgG, as in the case of the ScFv having no V5, KDR(ECD1-3)-Fc was immobilized onto the CM5 chip, and then various amounts of the antibody was allowed to run on the chip surface, thus obtaining sensorgrams. Based on the sensorgram obtained at each concentration, the kinetic constants $k_{on}$ and $k_{off}$ were measured, and $K_d$ was calculated from the ratio of the kinetic constants $k_{off}/k_{on}$ (Table 6).

As a result, it was confirmed that, among various ScFvs, ScFv having a high binding affinity for KDR was 6A6. Also, when 6A6 was converted in the form of IgG, the Kd value thereof was about 2-fold lower than that of IMC-1121. This suggests that 6A6 IgG was more strongly bound to KDR compared to IMC-1121.

TABLE 6

$K_d$ (M) value of anti-KDR ScFv, IgG

| | | | IgG | | |
|---|---|---|---|---|---|
| | ScFv | ScFv-V5 | $k_{on}$ (1/Ms) | $k_{off}$ (1/s) | $K_d$ (M) |
| 6A6 | 1.11E−08 | 6.93E−09 | 3.17E+05 | 7.3E−05 | 2.3E−10 |
| 6H1 | N/A | N/A | 5.02E+04 | 7.20E−03 | 1.43E−07 |
| 6G1 | 4.11E−07 | 3.31E−08 | 9.06E+04 | 5.48E−03 | 6.05E−08 |
| 6C1 | 4.31E−08 | N/A | 1.38E+05 | 9.58E−03 | 6.95E−08 |
| IMC-1121b | N/A | N/A | 2.27E+05 | 8.75E−05 | 3.85E−10 |

*N/A (not applicable)

Example 11

Analysis of KDR Neutralizing Ability of Anti-KDR-IgG in HUVEC Cells Using FACS Analysis Primary-cultured HUVEC cells were cultured in serum-free medium overnight to induce the overexpression of KDR, and then the cells were harvested, washed three times with PBS. The washed cells were allowed to react with 6A6 or IMC-1C11 IgG (10 μg/ml) at 4° C. for 1 hour, and then allowed to react with an FITC-labeled rabbit anti-human IgG antibody (Abchem, UK) for 60 minutes. After completion of the reaction, the cells were washed and analyzed with a flow cytometer (FACS; model EPICS9, Coulter Corp., USA).

Figure 14:
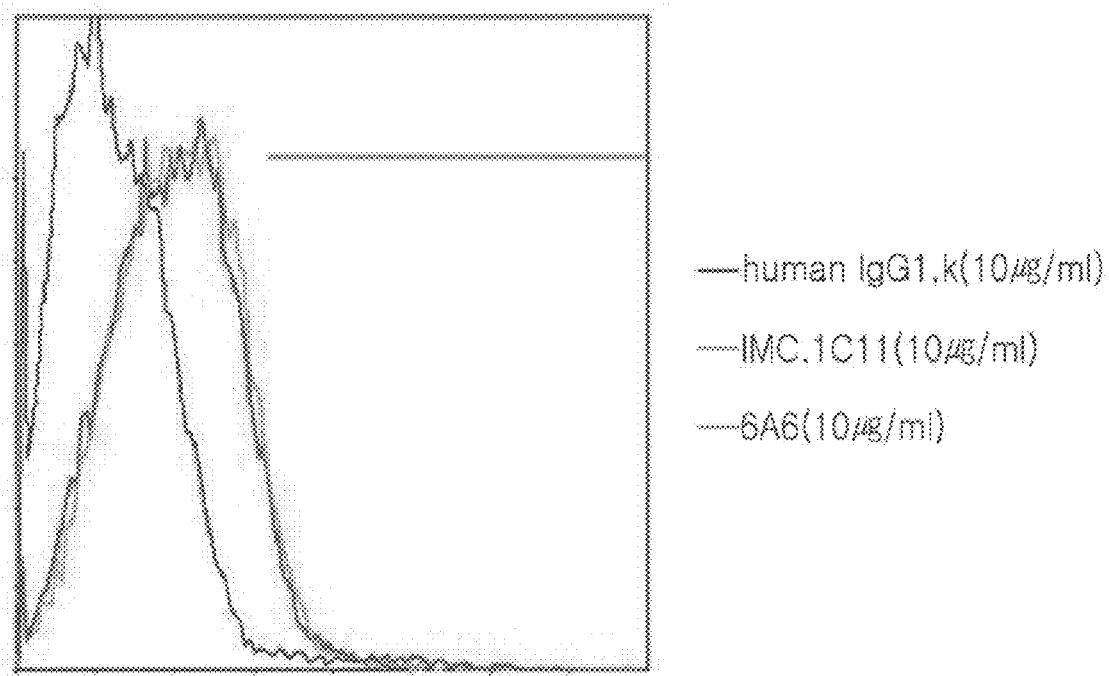
FIG. 14 shows the results of FACS analysis for the binding affinity of the inventive anti-KDR IgG antibody to HUVEC cells.

As a result, as shown in FIG. 14, IMC-1C11 and 6A6 recognized the KDR of HUVEC cells at the same level.

Also, in order to examine competitive inhibitory ability against VEGF, HUVEC cells were cultured in a serum-free condition overnight to induce the expression of KDR, and then the cells were harvested and washed three times with PBS. The washed cells were allowed to react with 20 ng/ml of VEGF at room temperature for 30 minutes. After the completion of the reaction, the cells were allowed to react with 6A6-IgG and IMC-1C11 IgG at 4° C. for 1 hour, and then allowed to react with an FITC-labeled rabbit anti-human IgG antibody at 4° C. for 30 minutes.

Figure 15:
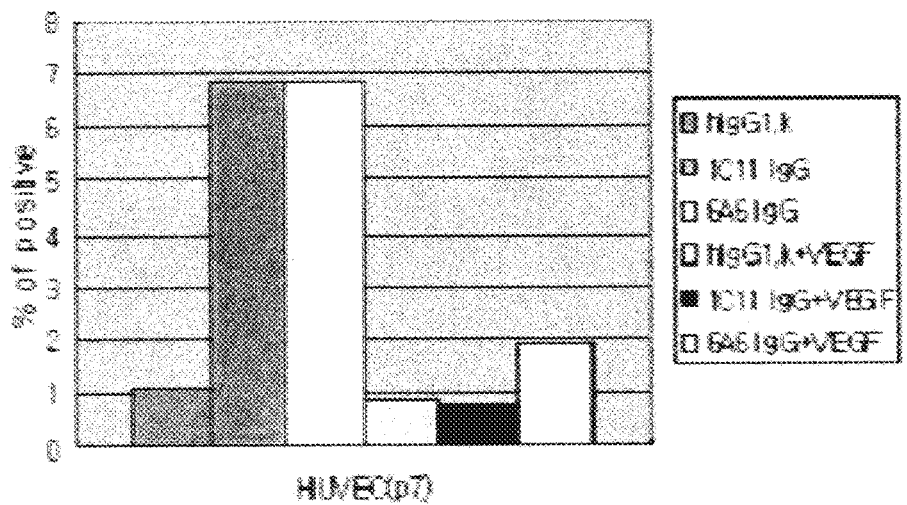
FIG. 15 shows FACS assay results for the competition of the inventive anti-KDR IgG antibody with VEGF165 in HUVEC cells.

As a result, as shown in FIG. 15, it was observed that the two antibodies all showed a signal of binding to VEGF165, indicating that 6A6-IgG was competitively bound to VEGF. Also, in the VEGF competition assays, 6A6-IgG and IMC-1C11 IgG showed the same level of KDR-neutralizing ability, but the KDR neutralizing ability in actual living cells was about two-fold higher for 6A6-IgG than for IMC-1C11 IgG.

Example 12

Analysis of KDR Neutralizing Ability of Anti KDR-IgG in K562 Cells

Figure 16:
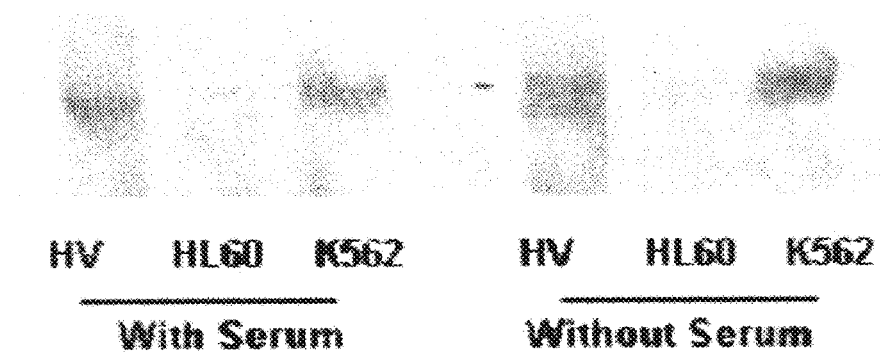
FIG. 16 shows the results of Western blot analysis for the expression of KDR in K562 cells (ATCC CCL-243).

In order to examine the KDR binding affinity of the antibodies in KDR expressing cells lines other than HUVEC cells, the expression of KDR in the leukemia cell line K562 (ATCC CCL-243) was analyzed. FIG. 16 shows the results of Western blot analysis for the expression of KDR in K562 (ATCC CCL-243) cells. As shown in FIG. 16, K562 and HUVEC cells expressed KDR regardless of the presence or absence of serum. Thus, the K562 cells (ATCC CCL-243) were treated in the same manner as the HUVEC cells of Example 11 and analyzed by FACS in order to examine whether KDR-IgG could bind to the K562 cells.

Figure 17:
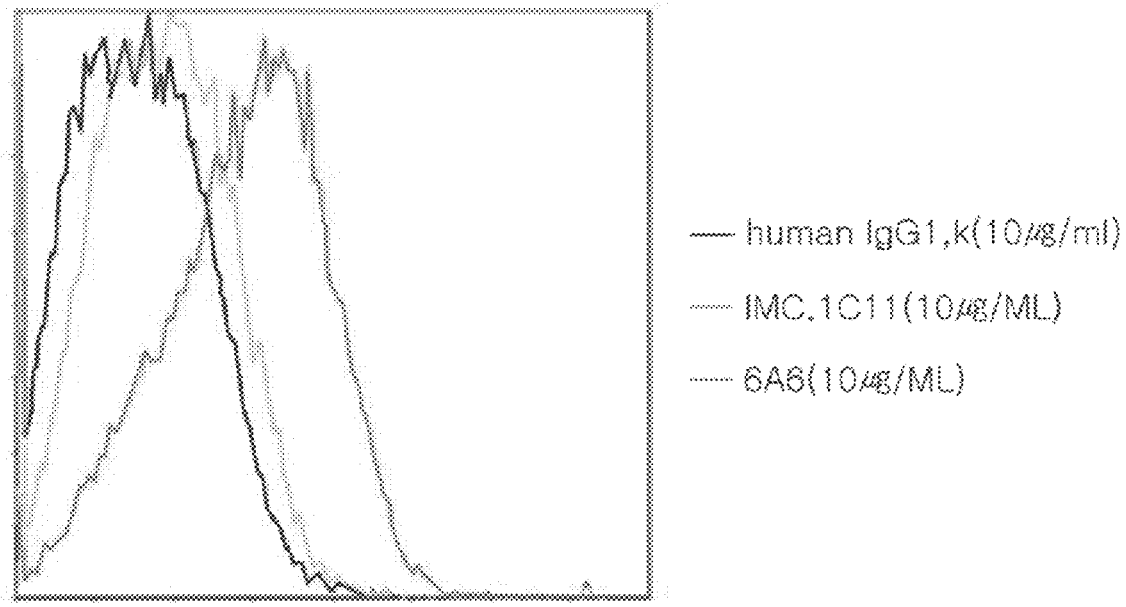
FIG. 17 shows the binding affinity of the inventive anti-KDR IgG antibody to the K562 cell line.
Figure 18:
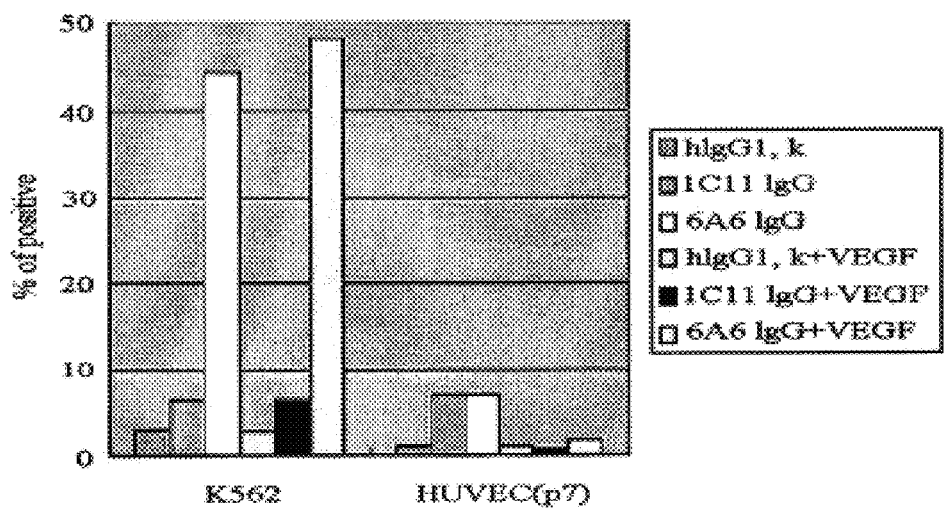
FIG. 18 shows FACS assay results for the competition of the inventive anti-KDR IgG antibody with VEGF in the K562 cell line.
Figure 19:
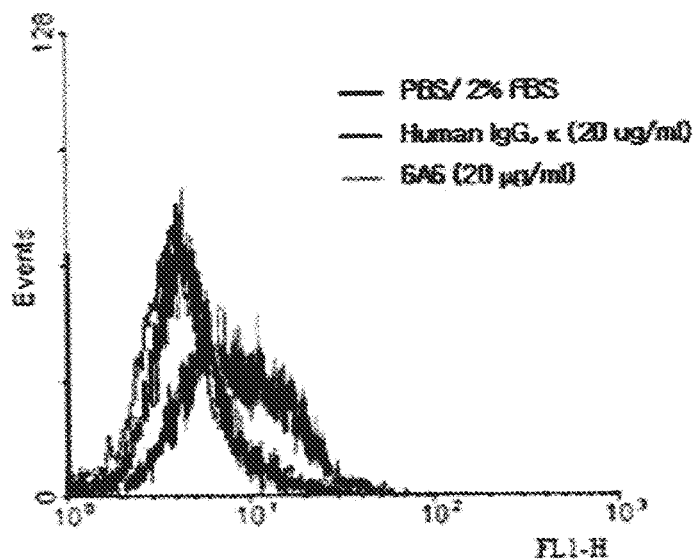
FIG. 19 shows FACS analysis results for the binding affinity of an anti-KDR antibody to a Gleevec-resistant cell line.

As a result, as shown in FIG. 17, only 6A6-IgG was bound to the K562 cells at a significant level, unlike the HUVEC cells. The results of FACS assays through VEGF competition are shown in FIG. 18. As shown in FIG. 18, the K562 cells did not show a great change in the rate of positive cells, unlike the HUVEC cells. Although the reason is unclear, this is thought to be because the 6A6 antibody strongly binds to KDR expressed on the surface of the K562 cells or regulates the growth of the cells using the autocrine loop mechanism of VEGF/KDR(VEGFR-2), and thus if VEGF is externally treated, the expression of KDR in the K562 cells is induced, so that an increased amount of the KDR protein is expressed on the cell surface, and the 6A6-IgG signal is increased compared to before the VEGF is externally treated. Also, as shown in FIG. 19, it was seen that 6A6-IgG could bind the KDR of gleevec-resistant K562 cells (The Catholic University of Korea).

Example 13

Analysis of Inhibition of HUVEC Cell Proliferation by 6A6 Antibody

Figure 20:
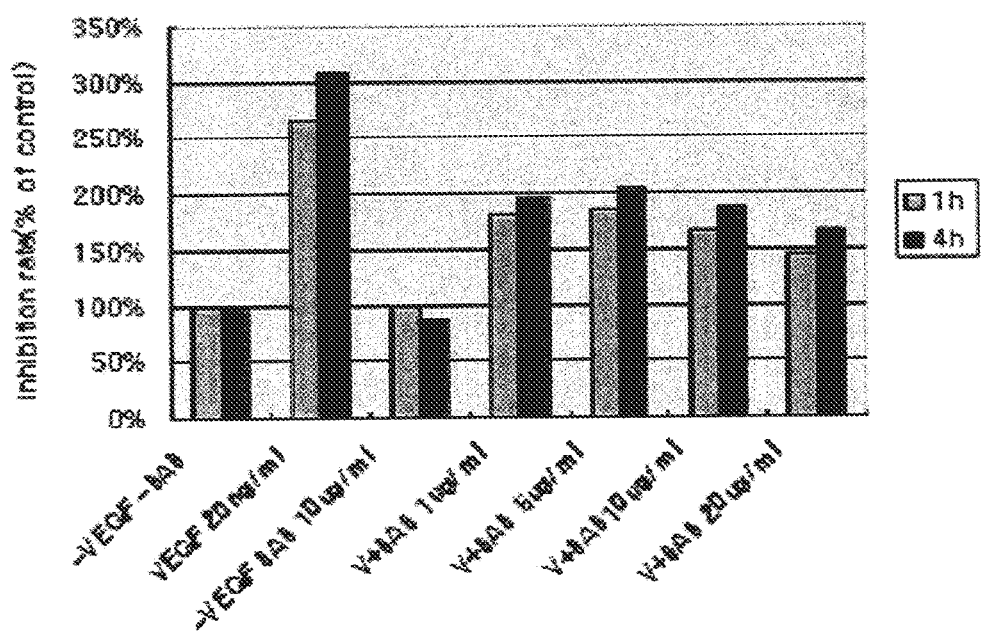
FIG. 20 shows analysis results for the cell proliferation inhibition of the anti-KDR-IgG according to the present invention.

The inhibition of HUVEC cell proliferation by anti-KDR-IgG was analyzed using WST-1 reagent (Roche, Swiss). HUVEC cells were dispensed into each well of a gelatin-coated, 24-well culture plate at a concentration of $2 \times 10^4$ cells/well and cultured for 18 hours. Then, the cells were further cultured in serum-free M199 medium (Sigma-aldrich, USA) for 4 hours, and then 20 ng/ml of VEGF and various concentrations of 6A6 were added thereto. Then, the WST-1 reagent was added thereto according to the manufacturer's manual, and after 1 hour and 4 hours, the cells were measured for absorbance at 450 nm and 690 nm (FIG. 20).

As a result, when the HUVEC cells were treated with VEGF, the proliferation thereof was increased by about three times, but when the 6A6 antibody was added to the HUVEC cells, the proliferation of the cells was reduced in a concentration-dependent manner.

Example 14

Analysis of Effect of 6A6 Antibody on Inhibition of KDR and ERK Phosphorylation

Sufficiently grown HUVEC cells were cultured in 1% FBS-containing M199 medium for 6 hours, and then treated with VEGF and 6A6, IMC-1121 and 6C1 antibodies at various concentrations for 10 minutes. Then, the cells were lysed with 1 ml of lysis buffer (20 mM Tris-HCl, pH 8.0, 2 mM EDTA, 137 mM NaCl, 1 mM $Na_3VO_4$, 1 mM PMSF, 10% glycerol, 1% Triton X-100) and centrifuged, and the supernatant was treated with 1 µg/ml of an anti-KDR/Flk-1 antibody (Santa cruz Biotechnology, USA) at 4° C. for 3 hours. The treated supernatant was incubated on protein-A agarose beads (Sigma-aldrich, USA) for 1 hour, and the immunoprecipitated protein was electrophoresed on SDS-PAGE, and then analyzed by Western blot (FIG. 21A).

As a result, it was observed that, when the cells were treated with VEGF, the phosphorylation of KDR was increased as expected, but the cells were treated with 6A6 or IMC-1121, the phosphorylation of KDR by VEGF was inhibited. Also, the 6C1 antibody had no effect on the neutralization of VEGF.

According to the above-described method, a test was carried out to examine whether the phosphorylation of the kinase ERK known to receive the signal of KDR would be inhibited. As a result, it was confirmed that 6A6 and IMC-1121 inhibited the phosphorylation of ERK, but 6C1 did not substantially inhibit the phosphorylation of ERK as expected (FIG. 21B).

Example 15

Figure 22:
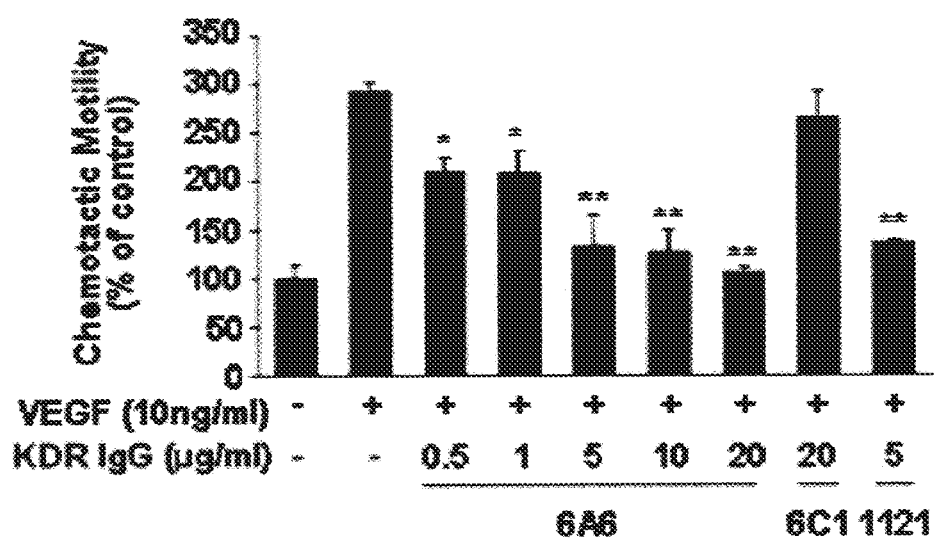
FIG. 22 shows the ability of an IgG-type KDR antibody to inhibit the migration of endothelial cells by VEGF.

Analysis of Inhibitory Effect of Anti-KDR-6A6 IgG on the Chemotaxis of Endothelial Cells Induced by VEGF In order to examine the inhibitory effect of 6A6-IgG on the migration of HUVEC cells induced by VEGF, a transwell (Corning costar, USA) having a 6.5-mm-diameter polycarbonate filter (8 µM pore size) was used. The surface of the lower layer of the filter was coated with 10 µg of gelatin, and fresh M199 medium (containing 1% FBS) and VEGF were placed in the lower layer well of the filter. HUVEC cells were diluted in M199 medium (containing 1% FBS) at a concentration of $1\times10^6$/ml, various concentrations of the anti-KDR antibodies were added thereto and allowed to react at room temperature for 30 minutes. 100 µl of the reaction solution was placed in the upper layer well and allowed to react at 37° C. for 4 hours. Then, the cells were stained with hematoxylin and eosin. Non-migrated cells were removed with cotton, and cells migrated into the lower layer well were observed with a microscope to measure the number of the migrated cells. As a result, it was observed that the migration of HUVEC cells induced by VEGF was inhibited by 6A6 in a concentration-dependent manner (FIG. 22).

Example 16

Analysis of Inhibitory Effect of Anti-KDR-6A6 IgG on Endothelial Cell Tube Formation Induced by VEGF In order to examine whether the 6A6 antibody inhibits HUVEC tube formation induced by VEGF, 250 µl of growth factor-reduced matrigel (Collaborative biomedical products, USA) was placed in each well of a 16-mm-diameter tissue culture plate and polymerized at 37° C. for 30 minutes. HUVEC cells were suspended in M199 medium (containing 1% FBS), and various amounts of the antibody was mixed and allowed to react with the cells. After 30 minutes, the cells were plated on the matrigel at a concentration of $2\times10^5$ cells/well, 10 ng/ml of VEGF was added thereto, and the cells were cultured for 20 hours. The cultured cells were observed with a microscope and imaged with an Image-Pro plus (Media cybernetics, USA). As a result, it was observed that HUVEC tube formation induced by VEGF was inhibited by 6A6-IgG (FIG. 23).

Example 17

Inhibition of VEGF-KDR Internalization by Binding of 6A6 Antibody to KDR on Cell Surface HUVEC cells were placed on a gelatin-coated cover slip at a concentration of $2\times10^4$ cells/well, after 24 hours, the cells were washed twice with M199 medium and cultured in M199 medium (containing 1% FBS) for 6 hours. The HUVEC cells were allowed to react with various concentrations of the antibody for 30 minutes and allowed to react with 10 ng/ml of VEGF for 10 minutes. After the completion of the reaction, the cells were immobilized and infiltrated with methanol or 2% formaldehyde for 10 minutes and washed with PBS. Then, the cells were blocked with 0.1% Triton X-100 and 2% BSA/PBS for 30 minutes, and the cells were allowed to react with a mouse KDR antibody for 1 hour, and then allowed to react with an FITC-labeled anti-mouse antibody at room temperature for 45 minutes. The cover slip was mounted with SloFade (Molecular Probe) and observed with a confocal microscope (Zeiss, Germany) at 488 nm (excitation wavelength).

Figure 24:
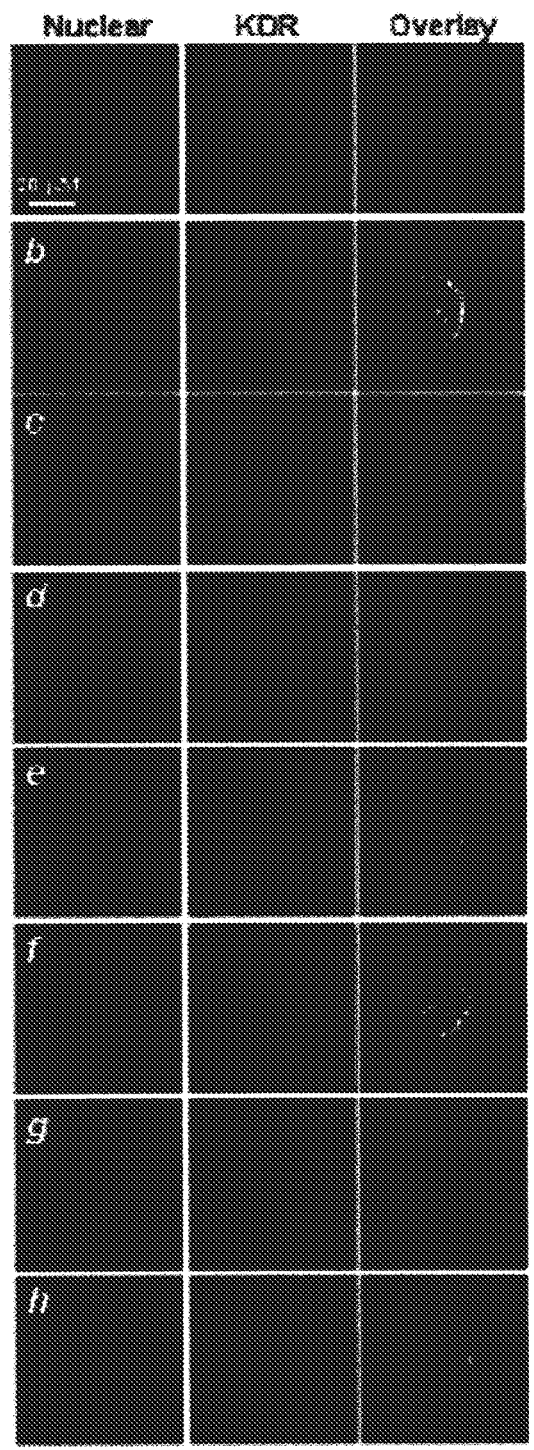
FIG. 24 shows the inhibition of VEGF-KDR internalization through the binding between the IgG-type KDR antibody and cell surface KDR.

As a result, as shown in FIG. 24, it was observed that the 6A6 antibody inhibited the infiltration of KDR into cells, and 6G1 did not substantially inhibit the infiltration of KDR into cells.

Example 18

Ex Vivo Analysis of Inhibitory Effect of Anti-KDR-IgG on Angiogenesis

In order to examine whether 6A6-IgG inhibits aortic ring vessel sprouting induced by VEGF, an aortic ring assay was performed. First, arteries were separated from 6-week-old rats (Sprague Dawley), and then cut to a size of about 0.5 mm. The cut artery was placed on 120 µl of a matrigel-coated, 48-well plate and covered with 50 µl of matrigel. VEGF (10 ng/ml) and each of 6A6-IgG, 6C1-IgG and 1121-IgG were mixed with human endothelial serum-free medium (Invitrogen) to a final volume of 200 µl, and the mixture was placed in each well of the plate. After 6 days, the cells were immobilized and stained with Diff-Quick (Baxter Diagnostics). Data were rated on a scale of 0 (least positive) to 5 (most positive), and six independent tests were performed. FIG.

25A shows a vessel sprouting image, and FIG. 25B shows the statistical results of scores for vessel sprouting. The 6A6 antibody inhibited vessel sprouting induced by VEGF, but the 6C1 antibody did not show the inhibitory ability. The above-described ex vivo rat aortic ring assay results have a very important meaning in addition to the simple fact that 6A6 inhibits angiogenesis induced by VEGF. That is, the results revealed that 6A6 could bind to Flk-1 to neutralize the human KDR homologue Flk-1 expressed in rats, although it was prepared for the purpose of neutralizing human KDR. In other words, it can be seen that the 6A6 antibody has cross-reactivity between humans and rats.

Example 19

Effect of 6A6 on Inhibition of In Vivo Angiogenesis Induced by VEGF (In Vivo Mouse Matrigel Plug Assay)

Following the rat aortic ring assay, a mouse matrigel plug assay was performed in order to examine whether the human KDR neutralizing antibody 6A6 can inhibit angiogenesis induced by VEGF in vivo in mice. For this purpose, 6-8-week-old C57/BL6 mice were subcutaneously injected with 0.6 ml of matrigel, containing 200 μg of the antibody, 100 ng of VEGF and 10 units of heparin. After 7 days, the matrigel plug was taken out by surgery, and the image thereof was photographed (FIG. 26A). Then, the plug was rapidly frozen with liquid nitrogen in the presence of an OCT (optimum cutting temperature) compound and cut to a thickness of 8-12 μm. The cut plug was fixed with 4% neutral buffered paraformaldehyde, and the density of the microvessels was measured with an anti-CD31 antibody (FIG. 26B). It was observed that the 6A6 antibody could inhibit blood vessel formation induced by VEGF in vivo in mice. Like the rat ex vivo experiment, it was confirmed again that the 6A6 antibody could neutralize the mouse KDR homologue Flk-1 and had cross-reactivity between humans and mice. Among therapeutic antibodies, a KDR antibody having cross-reactivity between humans and mice has not yet been reported. When the species cross-reactivity of the 6A6 antibody is used, the in vivo effect of the antibody can be confirmed using mice or rats.

Example 20

Anti-Cancer Effect of 6A6 Antibody in Colon Cancer Xenograft Animal Model

The anticancer effect of the 6A6 antibody in colon cancer xenograft animal models was analyzed using T cell-, B cell- and NK cell-deleted NOD/SCID IL-2R null mice (female, 11-week-old, weighed 25 g, The Jackson Laboratories, USA) known to have an advantage that the cells more easily receive human cancer cells, compared to NOD/SCID mice.

As human cancer cells, human colon cancer cells known as HCT116 (ATCC, USA) were used, and the injection of the tumor cells was performed by injecting the cells subcutaneously into the left side of the mice at a concentration of $2 \times 10^5$ cells (serum-free DMEM)/10 μl at day 0.

The 6A6 antibody was injected intravenously into the mice from day 1 (24 hours from day 0 at which the tumor cells were injected) three times a week. The mice were divided into three groups, each consisting of 5 animals. The group 1 was a PBS-injected group (control group), the group 2 was injected with 100 μg/ea (=4 mg/kg) of the 6A6 antibody, and the group 3 was injected with 200 μg/ea (=8 mg/kg) of the 6A6 antibody. The size of a tumor occurring in the mice was measured according to the following equation on alternate days for 26 days:

Tumor volume=½×(length×area×height).

Figure 27:
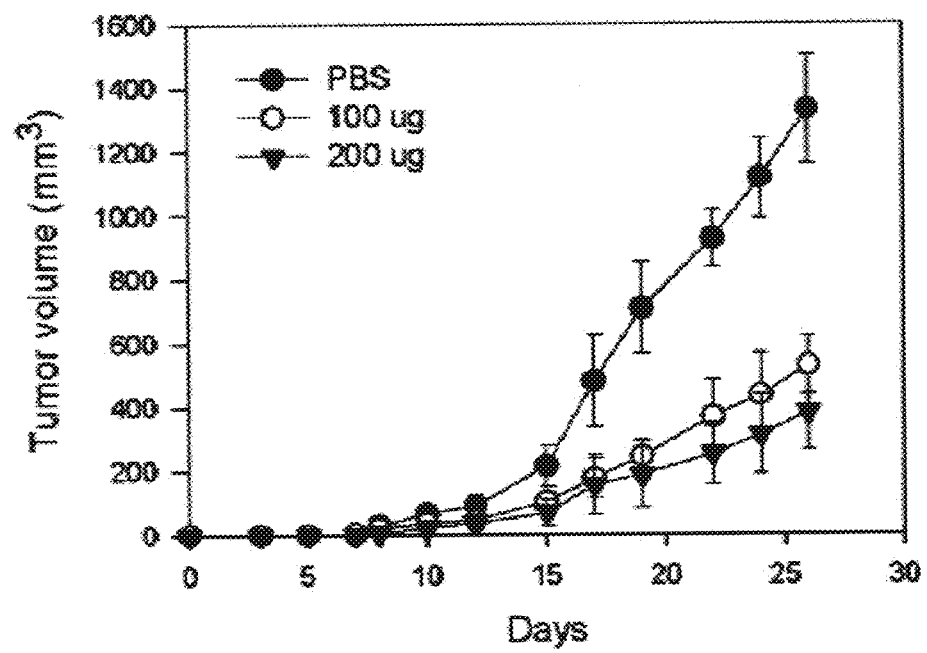
FIG. 27 shows analysis results for the inhibitory effect of a 6A6 antibody on tumor growth in the HCT116 cell line in a colon cancer mouse xenograft model.
Figure 28:
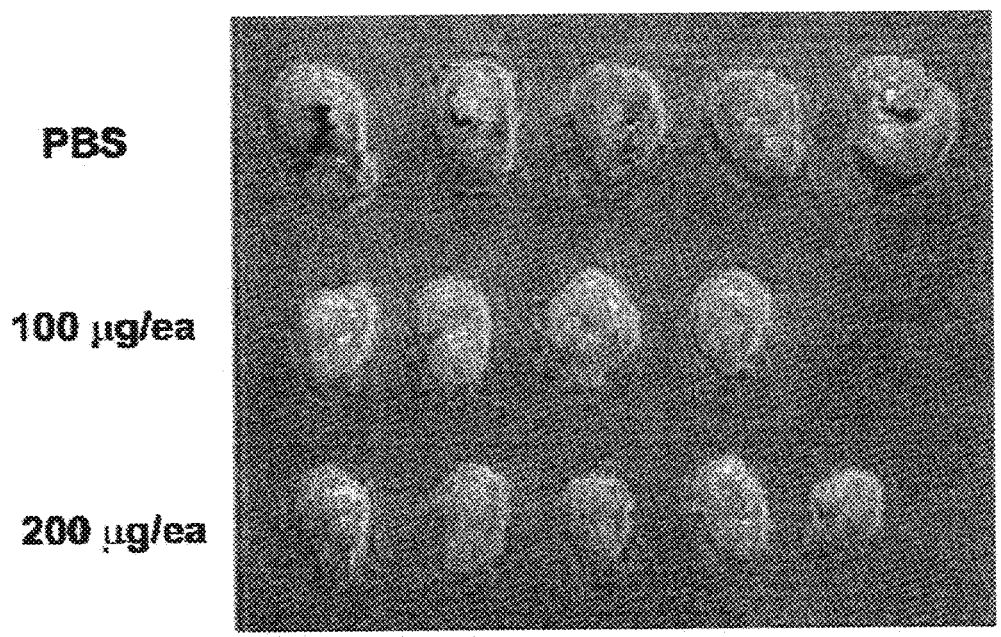
FIG. 28 is a photograph of tumors excised after treatment with the 6A6 antibody in the colon cancer mouse xenograft model.

At day 30, the mice were sacrificed, and the weight of a tumor was measured. As a result, it was observed that the tumor size was dose-dependently reduced in the groups administered with the 6A6 antibody, compared to the control group injected with PBS (FIG. 27 and FIG. 28).

Example 21

Anti-Cancer Effect of 6A6 Antibody in Lung Cancer Xenograft Animal Models

Human lung cancer A549 cells (ATCC, USA) were injected subcutaneously into nude mice (Japan SLC, Japan) at a concentration of $7 \times 10^7$ cells to form tumors. 10 days after the injection of the cancer cells, the tumors could be visually observed, and then the 6A6 antibody was injected intraperitoneally into the mice three times a week.

Figure 29:
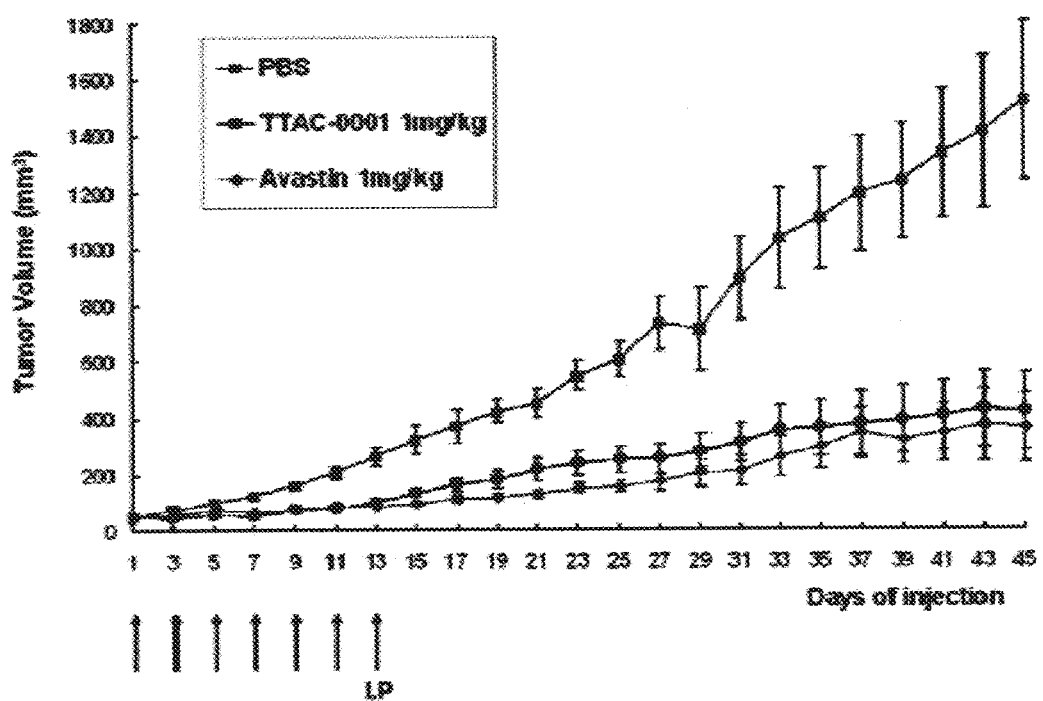
FIG. 29 shows analysis results for the inhibitory effect of the 6A6 antibody on tumor growth in the A549 cell line in a lung cancer mouse xenograft model.

The mice were divided into three groups, each consisting of five animals. The group 1 was a PBS-injected group (control group), the group 2 was injected with 1 mg/kg of the 6A6 antibody, and the group 3 was injected with 1 mg/kg of Avastin (Genentech, USA). As a result, as can be seen in FIG. 29, the growth of the tumor was inhibited in the group injected with the 6A6 antibody and the positive control group injected with Avastin, compared to the control group injected with PBS.

Example 22

In Vivo Tumor Targeting of Radioactive Iodine-Labeled 6A6 Antibody

Figure 30:
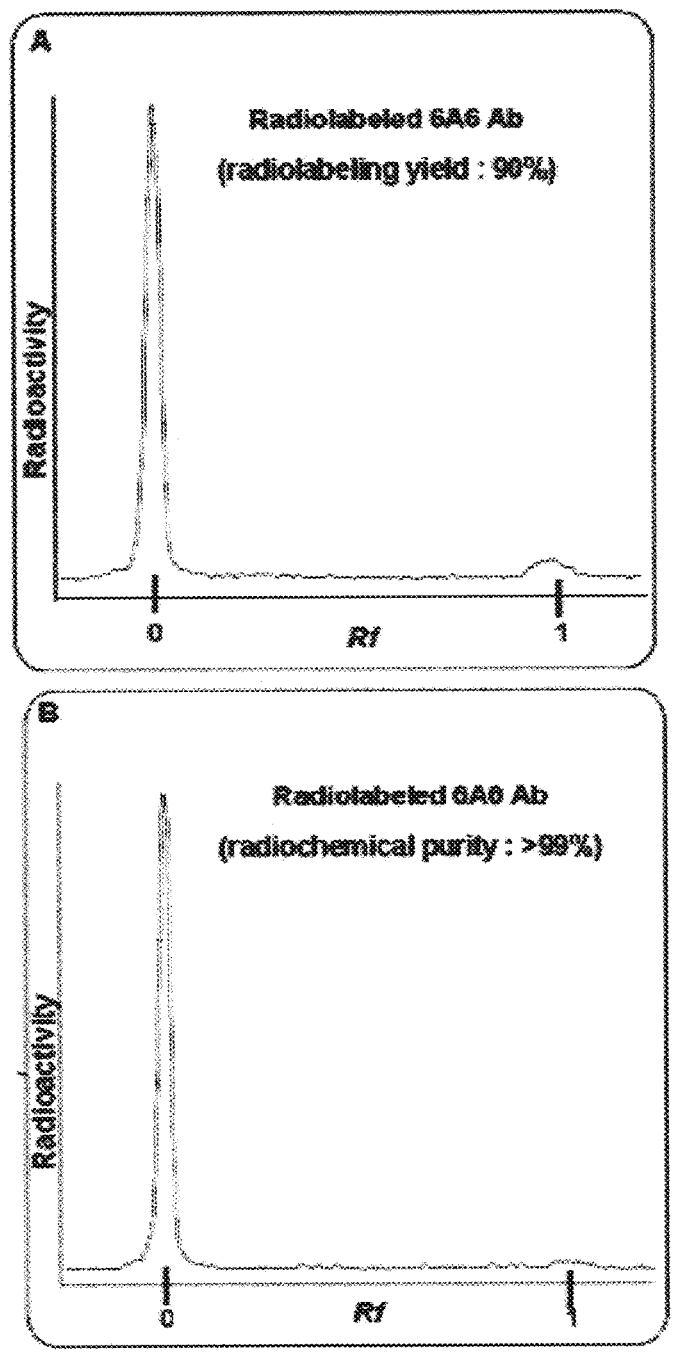
FIG. 30 shows the results of labeling of the IgG-type 6A6 antibody with radioactive isotope iodine.

The tumor targeting of the 6A6 antibody was analyzed using the binding affinity of the antibody to CML (chronic myelogenous leukemia) K562 cells. The antibody was labeled with radioactive iodine-125 using an iodobead method to label more than 90% of the antibody with iodine (FIG. 30A), and an anti-KDR (6A6) antibody labeled with radioactive iodine having a purity of more than 98% was prepared (FIG. 30B). A CML tumor model was prepared by injecting K562 cells subcutaneously into Balb/c nude mice, and when the tumor size reached 1 cm at 21-28 days after the injection of the K562 cells, the iodine-125-labeled antibody (100 μg) was injected into the tail vein of the K562 tumor model nude mice. 2 hour and 24 hours after the injection of the antibody, gamma-camera images of animals having tumors formed therein were obtained. It was observed that the introduction of the antibody into the tumors showed similar patterns at 2 hours and 24 hours, and the background radioactivity was reduced after 24 hours. It was observed that the antibody was localized to the tumor, suggesting that KDR was expressed on the K562 tumor. Thus, due to the therapeutic effect of the antibody itself by localization, as well as due to an increase in the therapeutic effect caused by beta-rays emitted from the radioactive isotope, the antibody can possibly be used as a radioimmunotherapy agent (FIG. 31).

Example 23

Affinity Maturation of 6A6-IgG Using Light Chain Shuffling

Figure 32:
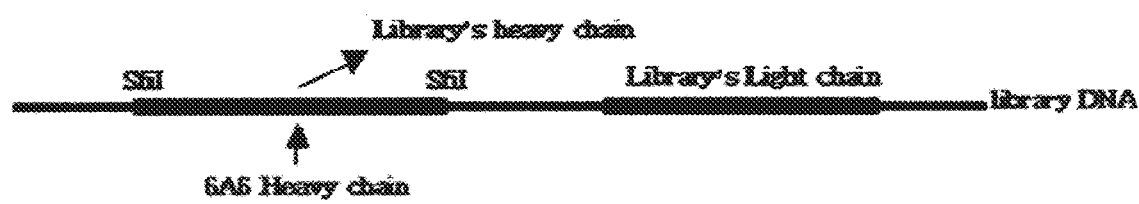
FIG. 32 is a schematic diagram showing the preparation of light-chain shuffling.

In order to identify antibodies having an affinity higher than that of 6A6, a heavy chain was removed from the DNA of the complete human antibody library, prepared in Example 2, using restriction enzyme SfiI. Into the site from which the heavy chain has been removed, a heavy chain of pAK-6A6 treated with SfiI restriction enzyme was inserted. The resulting DNA was transformed into ETB (Electro Ten blue) cells (Stratagene, USA), and the cells were cultured in SOB medium for 1 hour. Then, the cells were spread on a 2×YT (Cm) square plate, and the next day, the colony was collected and stored at −70° C. As a result, a 6A6 light chain shuffling library having a diversity of 4×10$^6$ was constructed (FIG. 32).

In order to examine whether the light chain shuffling of the library has been successfully achieved, 48 clones were randomly selected, and the light chain sequences thereof were analyzed. As a result, there was no overlap in the light chain sequences of the 48 clones.

From the library, clones having a binding affinity higher than that of 6A6 were screened in the same manner as in Example 3 through a biopanning process using a phage display.

18 candidates were finally obtained through the following procedures.

Figure 33:
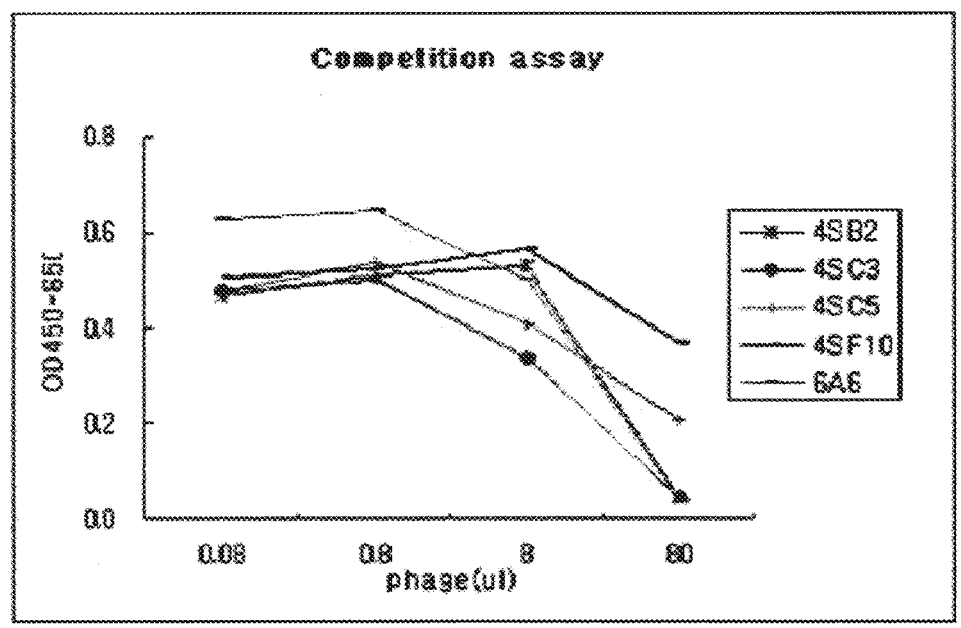
FIG. 33 shows the results of VEGF competition assays of anti-KDR antibodies obtained through light chain shuffling.

(1) In order to prevent 6A6 from being selected again during the biopanning process, the DNA of the 6A6 light chain shuffling library was treated with a restriction enzyme SpeI having a recognition site at the CDR3 of 6A6. After the DNA was transformed into ETB cells, a sub-library was constructed based on the cultured cells, and the KDR affinity of the sub-library was analyzed in ELISA. Among candidates resulting from the fourth panning, 94 candidates were selected and subjected to KDR binding assays in the same manner as in Example 5. Among candidates showing positive responses, 4 candidates were randomly selected, and the DNA sequences thereof were determined. Also, the candidates were subjected to VEGF competition assays using the respective phages (FIG. 33). As a result, 4SD5, 4SC3 and 4SC5, which had KDR neutralizing ability similar to equal to that of the positive control group 6A6, were selected.

(2) In a washing step in the biopanning process, KE3, KE6, 2KG8, 3KE11, 3KF11, 3KG3 and K3F1 were selected through competition with soluble KDR. The biopanning process used herein was as follows.

Maxisorp Star tubes (Nunc, Denmark) were coated with 4 ml of KDR (5 µg/ml) and blocked with 2% skimmed milk/PBS at 37° C. for 2 hours. Then, 500 µl of the 6A6 light chain shuffling library phage suspended in 2% skimmed milk was allowed to bind to the KDR, and then allowed to react in 0.1% PBS-T (tween20) for 1 hour. Then, the tubes were washed 10 times with 0.1% PBST and washed 10 times with PBS buffer. Then, 4 ml of soluble KDR (25 µg/ml/PBS) was added and allowed to bind thereto for 30 minutes, and the tubes were treated with 100 mM triethylamine for 10 minutes to elute the phage. The eluted phage was neutralized with 500 µl of 1M Tris-Cl (pH7.5) and transformed into *E. coli* XL1-Blue cells for 50 minutes, and then the cells were cultured.

Figure 34:
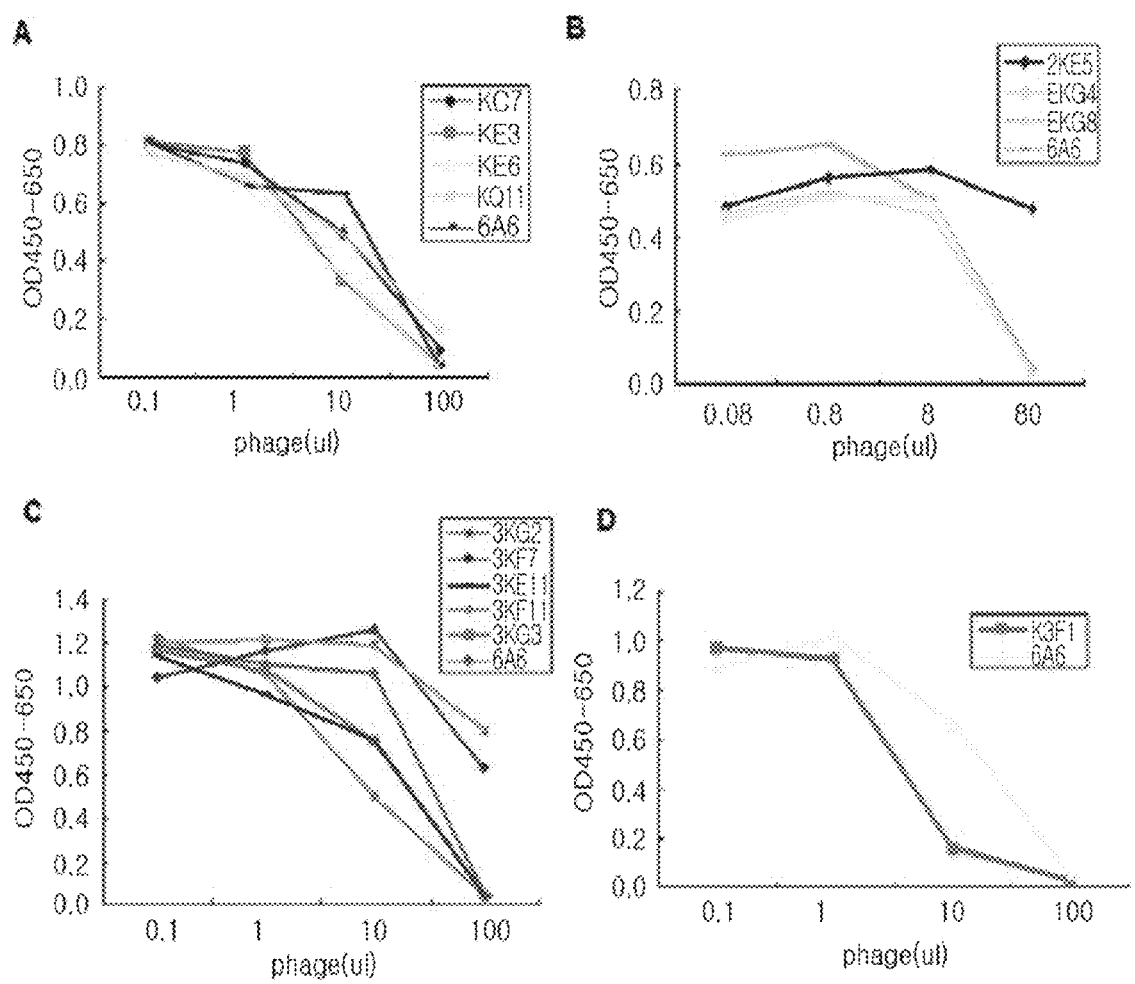
FIG. 34 shows the results of VEGF competition assays of anti-KDR antibodies obtained through light chain shuffling.

The antibodies selected in each of the three panning steps were subjected to VEGF competition assays in a ScFv-phage particle state. Among four candidate antibodies obtained through the first panning, KE3 and KE6, having high VEGF competitive power compared to those of the other candidate antibodies, were selected, and KC7 and KQ11 were excluded (FIG. 34A). Among three candidate antibodies obtained through the second panning, 2KE5 having low VEGF competitive power was excluded, and the remaining 2KG4 and 2KG8, having VEGF competitive power similar to that of 6A6, were selected. The 2KG4 showed the same sequence as 3KG3, an antibody selected later, and thus it was substituted with 3KG3 (FIG. 34B).

Among five candidate antibodies obtained through the third panning, 3KG2 and 3KF7, having low competitive power, were excluded, and only 3KE11, 3KF11 and 3KG3 were selected (FIG. 34C). Similarly, K3F1 obtained through the third panning was selected, and K3F1 showed a significantly high VEGF competitive power compared to that of 6A6 (FIG. 34D).

(3) In a step of allowing phage to bind to the antigen KDR in the biopanning process, IMC-1121 IgG obtained in Example 8 was also added and, as a result, 1E4, 3IG11, 3IG12, 31E1, 3IH2, I2F2, I3A12 and I3F2 clones were selected. The biopanning process used herein was as follows.

Maxisorp Star tubes (Nunc, Denmark) were coated with 4 ml of KDR (5 m/ml) and blocked with 2% skimmed milk/PBS at 37° C. for 2 hours. Then, 500 µl of the 6A6 light chain shuffling library phage suspended in 2% skimmed milk containing 21 µg/ml of IMC-1121 IgG (0.14 µM) was allowed to bind thereto for 1 hour, and then allowed to react in 0.1% PBST for 1 hour. Then, the tubes were washed 10 times with 0.1% PBST and washed with 10 times with PBS buffer. Then, 4 ml of soluble KDR (25 µg/ml/PBS) was added to the tubes and allowed to bind for 30 minutes, and then treated with 100 mM triethylamine for 10 minutes to elute the phage. The eluted phage was neutralized with 500 µl of 1M Tris-Cl (pH 7.5), and then transformed into *E. coli* XL1-Blue cells for 50 minutes, and the cells were cultured.

The antibodies selected in each of the three panning steps were subjected to VEGF competition assays in a ScFv-phage particle state. Among three candidate antibodies obtained through the first panning, only 1E4 having VEGF competitive power similar to that of 6A6 was selected (FIG. 35A). 1E4 was analyzed for the DNA sequence thereof and, as a result, 28 amino acids in 1E4 were different from those in 6A6. In addition, 6A6 had 108 light chain amino acids, whereas 1E4 had 107 amino acids, indicating that one amino acid was deleted in the CDR3 of 6A6.

FIG. 35B shows the results of VEGF competition assays of three candidate antibodies obtained through the third panning. In DNA sequencing, 3IG8 had a light chain sequence completely different from that of 6A6, and in the results of FACS, 3IG8 did not bind to living cells, indicating that it was not converted in the form of IgG. 31G11, 3IG12, 31E1 and 3IH2 were selected, and 3IA7 was excluded, because it had a stop codon in the light chain sequence. FIG. 35C shows the results of VEGF competition assays of candidate antibodies obtained through the second panning and the third panning. 3IA12, I3F2 and I2F2 were all selected.

The light chain DNA sequences of the 18 selected clones are shown in SEQ ID NO: 164 to SEQ ID NO: 181, and amino acid sequences deduced from the DNA sequences are shown in SEQ ID NO: 2 to SEQ ID NO: 19. Regions substituted compared to the light chain amino acid of 6A6 (TTAC-0001) are shown in Table 7. Also, the clones were renamed "TTAC-0002 to TTAC-0019" (Table 8).

TABLE 7

| Mutation site of 18 selected clones | |
|---|---|
| Clone name | Mutation site |
| KE3 (TTAC-0002) | S13A, R23G, L27I, D29S, V30Q, N31S |
| KE6 (TTAC-0003) | S13A, R19G, R23G, N26D, L27I, D29S, V30K, N31S, R38K, M47I, A51S |
| IE4 (TTAC-0004) | N1S, F2Y, M3E, V12S, S13A, R19T, R23E, D25K, L27I, D29S, V30K, N31S, R38K, V46L, M47I, A51Q, G56A, G67D, T69M, G76R, E78A, D91G, R92N, T93G, S94K, E95V, T99G, V103L |
| SD5 (TTAC-0005) | S13A, T100A |

TABLE 7-continued

Mutation site of 18 selected clones

| Clone name | Mutation site |
|---|---|
| 2KG8 (TTAC-0006) | S13A |
| 3KE11 (TTAC-0007) | T71I |
| 3KF11 (TTAC-0008) | P8S |
| 3KG3 (TTAC-0009) | P8H |
| 3IG11 (TTAC-0010) | V46I |
| 3IG12 (TTAC-0011) | R23M |
| 3IE1 (TTAC-0012) | P8S, S13P, P39R, Y96F |
| 3IH2 (TTAC-0013) | V12L, K16Q |
| K3F1 (TTAC-0014) | S13A, K16Q |
| I2F2 (TTAC-0015) | S9A |
| I3A12 (TTAC-0016) | E59K |
| I3F2 (TTAC-0017) | M47I |
| 4SC3 (TTAC-0018) | S94N |
| 4SC5 (TTAC-0019) | N1Q, M3V, S13A, R23G, D25N, L27I, D29S, V30K, N31S, R38K, M47I, A51S, S66F, G76R, R92S, T93S, S94R, E95D |

TABLE 8

New name of antibodies developed

| Name of antibodies developed | New name |
|---|---|
| 6A6 | TTAC-0001 |
| KE3 | TTAC-0002 |
| KE6 | TTAC-0003 |
| IE4 | TTAC-0004 |
| SD5 | TTAC-0005 |
| 2KG8 | TTAC-0006 |
| 3KE11 | TTAC-0007 |
| 3KF11 | TTAC-0008 |
| 3KG3 | TTAC-0009 |
| 3IG11 | TTAC-0010 |
| 3IG12 | TTAC-0011 |
| 3IE1 | TTAC-0012 |
| 3IH2 | TTAC-0013 |
| K3F1 | TTAC-0014 |
| I2F2 | TTAC-0015 |
| I3A12 | TTAC-0016 |
| I3F2 | TTAC-0017 |
| 4SC3 | TTAC-0018 |
| 4SC5 | TTAC-0019 |

INDUSTRIAL APPLICABILITY

As described in detail above, the present invention provides a fully human antibody, which has an excellent ability to neutralize VEGF receptor in cells and in vivo, and a composition for inhibiting angiogenesis and a composition for treating cancer, which contain said antibody. The inventive 6A6 antibody neutralizing vascular endothelial growth factor receptor shows excellent neutralizing ability in living cells, compared to that of a commercially available antibody against vascular endothelial growth factor receptor, and shows the ability to neutralize vascular endothelial growth factor receptor not only in humans, but also in mice and rats. Thus, the 6A6 antibody will be useful in anticancer studies and will be highly effective in cancer treatment.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:
1. A single chain variable fragment (ScFv) molecule comprising:
   a light chain variable region comprising the amino acid sequence of any one of SEQ ID NOS: 2 to 6, 10 and 11, and
   a heavy chain variable region comprising the amino acid sequence of SEQ ID NO: 20,
   wherein the ScFv molecule functions to neutralize vascular endothelial growth factor receptor.
2. A composition for inhibiting angiogenesis comprising the ScFv molecule of claim 1.

3. A composition for treating cancer comprising the ScFv molecule of claim 1.

4. An IgG antibody comprising:
a light chain variable region comprising the an amino acid sequence of any one of SEQ ID NOS: 2 to 6, 10 and 11, and
a heavy chain variable region comprising the an amino acid sequence of SEQ ID NO: 20,
wherein the antibody functions to neutralize vascular endothelial growth factor receptor.

5. A composition for inhibiting angiogenesis comprising the IgG antibody of claim 4.

6. A composition for treating cancer comprising the IgG antibody of claim 4.

* * * * *